(12) United States Patent
Kang et al.

(10) Patent No.: US 9,102,942 B2
(45) Date of Patent: Aug. 11, 2015

(54) PHARMACEUTICAL COMPOSITION FOR INHIBITING ABNORMAL PROLIFERATION OF CELLS

(75) Inventors: Sang Won Kang, Seoul (KR); Soo Young Lee, Seoul (KR)

(73) Assignee: Ewha University—Industry Collaboration Foundation (KR)

( * ) Notice: Subject to any disclaimer, the term of this patent is extended or adjusted under 35 U.S.C. 154(b) by 0 days.

(21) Appl. No.: 13/577,231

(22) PCT Filed: Feb. 7, 2011

(86) PCT No.: PCT/KR2011/000768
§ 371 (c)(1),
(2), (4) Date: Aug. 3, 2012

(87) PCT Pub. No.: WO2011/096756
PCT Pub. Date: Aug. 11, 2011

(65) Prior Publication Data
US 2012/0308568 A1   Dec. 6, 2012

(30) Foreign Application Priority Data
Feb. 4, 2010  (KR) .................. 10-2010-0010623

(51) Int. Cl.
*C12N 15/11*   (2006.01)
*A61K 39/00*   (2006.01)
*C12N 15/113*  (2010.01)

(52) U.S. Cl.
CPC ............ *C12N 15/1135* (2013.01); *A61K 39/00* (2013.01); *C12N 2310/11* (2013.01)

(58) Field of Classification Search
CPC ............... A61K 39/00; C12N 2310/11; C12N 2310/14; C12N 2310/16
See application file for complete search history.

(56) References Cited

U.S. PATENT DOCUMENTS

| | | | |
|---|---|---|---|
| 7,576,177 B2 * | 8/2009 | Karmon et al. ............... 530/350 |
| 2003/0100036 A1 * | 5/2003 | Vojdani ......................... 435/7.92 |
| 2004/0022777 A1 * | 2/2004 | Kolb et al. ..................... 424/94.1 |
| 2004/0127435 A1 * | 7/2004 | Carson et al. .................. 514/43 |
| 2009/0099080 A1 * | 4/2009 | Altieri et al. .................... 514/12 |
| 2012/0142588 A1 * | 6/2012 | Rozing et al. .................. 514/5.6 |

FOREIGN PATENT DOCUMENTS

| | | |
|---|---|---|
| KR | 100454554 A | 10/2004 |
| KR | 100565437 A | 3/2006 |
| KR | 1020080031474 A | 4/2008 |
| KR | 1020090048403 A | 5/2009 |
| WO | 97/01959 A1 | 1/1997 |
| WO | WO2005/012514 A1 * | 2/2005 |
| WO | 2009/036092 A2 | 3/2009 |

OTHER PUBLICATIONS

Itoh et al. (Eur. J. Biochem. 269, 5931-5938, 2002).*
Broemer et al., "Requirement of Hsp90 activity for IkappaB kinase (IKK) biosynthesis and for constitutive and inducible IKK and NF-kappaB activation," Oncogene 23:5378-5386, 2004.
Hayden et al., "Signaling to NF-kappaB," Genes & Development 18:2195-2224, 2004.
Karin et al., "Phosphorylation Meets Ubiquitination: The Control of NF-kappaB Activity," Annual Review of Immunology 18:621-663, 2000.
Park et al., "Heat Shock Protein 27 Association with the I kappaB Kinase Complex Regulates Tumor Necrosis Factor alpha-induced NF-kappaB," Journal of Biological Chemistry 278(37): 35272-35278, 2003.
Ran et al., "Hsp70 promotes TNF-mediated apoptosis by binding IKKgamma and impairing NF-kappaB survival signaling," Genes & Development 18:1466-1481, 2004.
Wang et al., "NF-kappaB Induces Expression of the Bcl-2 Homologue A1/Bfl-1 to Preferentially Suppress Chemotherapy-Induced Apoptosis," Molecular and Cellular Biology 19(9): 5923-5929, Sep. 1999.
Wong et al., "Manganous Superoxide Dismutase Is Essential for Cellular Resistance to Cytotoxicity of Tumor Necrosis Factor," Cell 58: 923-931, Sep. 8, 1989.
Korean Patent Abstracts for Korean Publication No. 1020050014573, published Feb. 7, 2005, one page.
Korean Patent Abstracts for Korean Publication No. 1020080031474, published Apr. 8, 2008, one page.
Korean Patent Abstracts for Korean Publication No. 1020090048403, published May 13, 2009, one page.

* cited by examiner

*Primary Examiner* — Brian Whiteman
(74) *Attorney, Agent, or Firm* — Cooley LLP

(57) ABSTRACT

The present invention relates to a pharmaceutical composition for preventing or treating diseases related to abnormal proliferation of cells, comprising a cytoplasmic heat shock protein (Hsp)60 kDa inhibitor as an active ingredient, and to a screening method and a kit using the composition. According to the present invention, substances which inhibit expression of cytoplasmic Hsp 60 genes or inhibit activity of cytoplasmic Hsp 60 or inhibit binding between cytoplasmic Hsp 60 and IKK protein prevent interaction between cytoplasmic Hsp 60 and IKK complexes to make NF-κB path inactive, and thus induce apoptosis. Therefore, the substances can be valuably used in preventing or treating diseases related to abnormal proliferation of cells, such as cancer, inflammatory diseases or hyperproliferative vascular diseases.

15 Claims, 57 Drawing Sheets

PHARMACEUTICAL COMPOSITION FOR INHIBITING ABNORMAL PROLIFERATION OF CELLS

CROSS-REFERENCES TO RELATED APPLICATIONS

This application is a U.S. national phase application of International PCT Patent Application No. PCT/KR2011/000768, which was filed on Feb. 7, 2011, which claims priority to Korean Patent Application No. 10-2010-0010623, filed Feb. 4, 2010. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_016_01US_ST25.txt. The text file is 9 KB, was created on Aug. 2, 2012, and is being submitted electronically via EFS-Web.

BACKGROUND OF THE INVENTION

1. Field of the Invention

The present invention relates to a pharmaceutical composition for the prevention or treatment of diseases associated with abnormal cell proliferation, comprising a cytosolic Hsp60 inhibitor, and a method and kit for screening a therapeutic agent for diseases associated with abnormal cell proliferation using cytosolic Hsp60.

2. Description of the Related Art

Mammalian cells express a number of survival genes that play the roles in inhibiting caspase activation, removing harmful oxygen radicals, defending mitochondrial function, and checking cell cycle. Among the transcription factors responsible for the induction of the survival genes, nuclear factor-Kb(NF-κB) is a key element that orchestrates the complex cell survival response. In particular, the NF-κB-dependent survival genes include antiapoptotic genes, such as c-IAPs and c-FLIP, and mitochondrial safeguard genes, such as manganese-superoxide dismutase(MnSOD) and Bcl-2 family members.

A central kinase in the NF-κB activation pathway is the inhibitor of κB kinase (IκB kinase or IKK) that phosphorylates the IκB protein in amino-terminal serine residues, leading to its ubiquitinylation and proteosomal degradation and to the consequent liberation of NF-κB proteins [Karin M et al., Annu Rev Immunol 18:621-663 (2000)]. The extracellular stimuli to activate NF-κB pathway converge to IKK [Hayden M S et al., Genes Dev 18: 2195-2224 (2004)]. Therefore, numerous efforts have been made to delineate the regulation of IKK activation.

Specifically, that the IKK activation is regulated by dependent upon phosphorylation has already been known. The phosphorylation of two serine residues (Ser177/Ser181 in human IKKβ) in activated T-loop is essential for the activation thereof, while the autophosphorylation of C-terminal serine cluster turns off the activation. Many kinases have been implicated as being involved in the activation phosphorylation: NF-κB inducing kinase (NIK), mitogen-activated protein kinase/ERK kinase kinases 1 (MEKK1), MEKK2/3, hematopoietic progenitor kinase-1 (HPK1), mixed-lineage kinase 3(MLK 3), and TGF-β activated kinase 1(TAK1). However, except for in the case of TAK1, it is unclear how the upstream kinases activate the IKK complex.

Further, the ubiquitin-dependent regulation of IKK activation has been studied for many years. Recently, the regulatory subunit IKKγ (or NEMO) of IKK complex has been shown to be ubiquitinated, as well as to recognize Lys63-linked polyubiquination chain on RIP 1 (receptor-interaction protein 1).

Further, the regulation of IKK activation via the interacting proteins has already been known. The best examples are heat shock proteins. For example, Cdc37 and Hsp90 have been reported to act as additional components of the IKK complex that stabilize the complex [Chen G et al., Mol Cell 9:401-410 (2002)]. Hsp27 has been shown to interact with IKKβ in a TNF-α-dependent manner [Park K J et al., J. Biol. Chem. 278:35272-35278 (2003)]. Hsp70 also interacts with IKKγ but interferes with the IKK activation [Ran R et al. Genes Dev 18:1466-1481 (2004)]. In addition, the association between protein phosphatase 2Cβ (PP2Cβ) and the IKK complex has already been demonstrated, and ELKs have also been identified as a new regulatory subunit of IKK complex that mediates the recruitment of IκB to the complex. However, there is no indication of a mitochondrial protein involved in the IKK/NF-κB activation.

Meanwhile, the molecular chaperones Heat Shock Protein 90 (Hsp90), Rsp60, and Heat Shock 70 kDa Protein 9 (HSPA9/mortalin) are found at increased levels in mitochondria of tumor cells, and "mitochondrial-targeted" chaperone inhibitors are known to be used for the treatment of disorders associated with unwanted cell proliferation [WO09/036,092].

The present inventors have made many efforts to understand the mechanism of NF-κB activation. As a result, they identified that Ksp60, which functions as a Heat Shock Protein in the mitochondria, directly interacts with IKKα/β in the cytoplasm and then promotes the phosphorylation-dependent activation of the kinase, and subsequently increased transcriptional activity of NF-κB induced survival genes to reduce the intracellular reactive oxygen species (ROS) level, leading to an increase in cell survival against apoptosis-inducing stress. Accordingly, they found that abnormal cell proliferation-associated diseases can be treated by inhibiting cytosolic Hsp60 expression and/or activation, thereby completing the present invention.

SUMMARY OF THE INVENTION

An object of the present invention is to provide a pharmaceutical composition for the prevention or treatment of diseases associated with abnormal cell proliferation.

Another object of the present invention is to provide a method and kit for screening a therapeutic agent for diseases associated with abnormal cell proliferation.

The diseases associated with abnormal cell proliferation may be cancer, inflammatory diseases, or hyperproliferative vascular disorders.

Other objects and advantages of the present invention will be more clearly understood from the following detailed description, the claims, and the accompanying drawings.

BRIEF DESCRIPTION OF THE DRAWINGS

FIG. 1 shows a silver-stained polyacrylamide gel resolving the affinity-purified IKK complex. FIG. 2 is MS/MS spectra of [M+2H]$^{2+}$ ions of the peptides derived from the protein band corresponding to Hsp60. FIG. 3 is the result of immunoblot (IB) analyses of IKK subunits and Hsp60 in the affinity-purified IKK complex. FIG. 4 shows interaction of Hsp60 with IKK complex. IKK complex was immunoprecipitated (IP) from HeLa cell lysates (500 μg total proteins for each) with IKKα, IKKβ and IKKγ-specific antibodies. The IKKα/β/γ subunits, Hsp60, and Hsp90 were immunoblotted. WCL represents whole cell lysate. FIG. 5 shows TNF-α-independent interaction of Hsp60 and IKK complex. FIG. 6 is the result of co-immunoprecipitation of Hsp60 and IKK complex in cytosolic fraction. Upper panel, post-nuclear supernatant (PNS), cytosol (Cyto), and mitochondria (Mito) fractions from HeLa cells were immunoblotted. COX4 and tubulin were used as mitochondrial and cytosolic markers, respectively. Lower panel, Hsp60 was immune-precipitated from the cytosolic fraction using either control goat IgG or anti-Hsp60 antibodies (K-19 and N-20). Representative blots are shown (n=3).

FIG. 8 shows direct binding of Ksp60 and IKK subunits. The 293 T cells were co-transfected with HspGOc (HA tag) and each of IKK subunit proteins (Flag tag) for 24 hours. FIG. 9 shows in vitro association of Hsp60 with IKKα and IKKβ. GST-fused Hsp60 proteins bound to the glutathione sepharose beads was incubated with the lysates of Sf9 insect cells expressing $His_6$-tagged IKK proteins. Ksp60 and IKKs were detected by immune-blotting for GST and HA tags, respectively, FIG. 10 shows a schematic diagram showing deletion mutants of Hsp60. The putative phosphorylation sites of kinases, including (1) PKA/PKG and (2) PKC, are indicated. FIGS. 11 and 12 show interaction of Hsp60 wild-type (WT) and deletion mutants with ectopically-expressed IKKα in 293 T cells (FIG. 11) or to endogenous IKK complex in IKKα or HeLa cells (FIG. 12). Representative blots and images are shown (n=3). Abbreviations: G, control vector; n.s., nonspecific.

FIG. 15 shows TNF-α-induced MAP kinase activation in HeLa cells transfected with either mock or GDNs. The activation was analyzed by using phospho-specific antibodies. The phosphoblots were re-probed with whole protein antibodies for equal loading. FIG. 16 shows activation of various transcription factors in mock- or ODN-transfected HeLa cells. AP-1 and NF-AT transcriptional activation were induced by epidermal growth factor (EGF, 100 ng/mL). CRE transcriptional activation was induced by forskolin (1 μM). FIG. 17 shows TNF-α-induced NF-κB transcriptional activation in 293 T and A549 cells transfected with either mock or ODNs. In FIGS. 16 and 17, relative luciferase activity was measured using an enhanced luciferase assay kit (Promega) and normalized to the β-galactosidase activity. Data are means±S.D. of four independent experiments (In FIG. 17, *P<0.001 and **P<0.05 versus stimulated S-ODN-transfected cells).

FIG. 18 shows ablation of cytosolic Hsp60 by antisense ODNs. The cytosolic and mitochondrial fractions prepared from: mock or ODN-transfected HeLa cells were: immunoblotted: S, sense ODN; AS-1 and AS-2, antisense ODNs. The mitochondrial fraction was loaded at a volume of one-fifth of the corresponding cytosolic fraction. In particular, Prx III, which is an antioxidant enzyme present in the mitochondrial matrix, was used as a mitochondrial marker to watch the nonspecific mitochondrial rupture. FIG. 19 shows Half-life of ectopically-expressed Hsp60c protein (HA tag) after inhibition of protein synthesis with cycloheximide. The intensity of HA band was measured and normalized by the amount of IKKα band. Data in the graph are means±S.D. of two independent experiments and fitted in SigmaPlot 8.0 software. FIG. 20 shows proteasome-dependent turnover of cytosolic Hsp60c protein. HeLa cells were pretreated with or without MG132 (5 μM) for 30 minutes before cycloheximide treatment. FIG. 21 shows TNF-α-induced IKK and JNK1 activation in mock or ODN-transfected cells. The in vitro kinase activity (KA) was averaged with the values from two independent experiments, and it is represented as a fold increase of the activity versus the unstimulated and mock-transfected cells (lane 1). FIG. 22 shows NF-κB transcriptional activation in mock or ODN-transfected cells. The increasing concentration of AS-ODN (100 nM or 200 nM) was tested. FIG. 23 shows NF-κB transcriptional activation in mock or ODN-transfected cells. The relative luciferase activity was normalized to the β-galactosidase activity and data are means±S.D. of four independent experiments (*P<0.01, **P<0.005 versus stimulated S-ODN-transfected cells).

FIG. 24 shows fluorescence images showing transduction of Hsp60-neutralizing antibody (Hsp60N) into the cytoplasm of HeLa cells. Mitotracker Red (Molecular Probes, USA) and DAPI indicate mitochondria and nuclei, respectively. FIG. 25 shows the transduced Hsp60N antibody bound to endogenous Hsp60. After antibody transfection, the HeLa cell lysates were subjected to precipitation using Protein-A sepharose beads. The precipitated proteins were immunoblotted for Hsp60. FIG. 26 shows IKK and JNK1 activation in response to TNF-α in control IgG or Hsp60N antibody-transfected HeLa cells. The in vitro kinase activity (KA) was averaged with the values from two independent experiments, and it is represented as a fold increase of the activity versus the unstimulated and control IgG-transfected cells (lane 1). FIG. 27 shows TNF-α-induced NF-κB transcriptional activation in antibody-transfected cells (*P<0.01 versus stimulated IgG-transfected cells).

FIG. 28 shows incorporation of ectopically-expressed Hsp60c (HA tag) in IKK complex. FIG. 29 shows TNF-α-induced IKK activation in HeLa cells. FIG. 30 shows TNF-α-induced NF-κB activation in HeLa cells (n=4; *P<0.0001 versus unstimulated counterpart). FIG. 31 shows TNF-α-induced NF-κB activation in the transfected IKKp−/−3T3 cells (n=4; *P<0.0001 versus stimulated CGN-transfected cells; N.D. not detected).

FIG. 32 shows TNF-α- induced JNK activation in HeLa cells expressing Hsp60c (HA tag). FIGS. 33 to 35 show activation of various transcription factors in HeLa cells transfected with either control vector or Hsp60c (HA tag), AP-1 (FIG. 33) and NF-AT (FIG. 34) transcriptional activation were induced by epidermal growth factor (EGF, 100 ng/mL). CRE transcriptional activation (FIG. 35) was induced by forskolin (1 μM). The relative luciferase activity was measured using an enhanced luciferase assay kit (Promega) and normalized to the β-galactosidase activity. Data are means±S.D. of four independent experiments.

FIG. 36 shows association of Hsp60c wild-type (WT) and mutants with IKKα. The indicated proteins were co-expressed in 293 T cells, as shown in FIG. 8. FIGS. 37 and 38 show IKK (FIG. 37) and NF-κB transcriptional activation (FIG. 38) in cells expressing Hsp60c wild-type and chaperone-inactive mutants. The kinase and reporter activities were analyzed as described in FIGS. 13 to 17 (for reporter assay, P<0.0001 versus unstimulated counterpart; n=6). FIG. 39 shows in vitro kinase activity of IKK in the presence of recombinant Hsp60 protein. The IKK complex was immunoprecipitated from HeLa cell lysates and incubated with or without the indicated GST proteins (20 μg each) in the kinase reaction buffer for 10 minutes before the kinase reaction. FIG. 40 shows serine phosphorylation of IKKα/β in HeLa cells transfected with AS-1 ODN. Data in the graph are means±S.D. (n=3, *P<0.02, **P<0.001). FIG. 41 shows serine phosphorylation of IKKα/β in Hsp60c-expressing HeLa cells. A representative blot is shown (n=3).

FIG. 42 shows the result of RNase protection assay for induction of anti-apoptotic genes in ODN-transfected cells. The autoradiogram shown is a representative of three independent experiments. FIGS. 43 and 44 show QPCR for induction of endogenous NF-κB target genes in ODN-transfected cells (FIG. 43) and antibody-transfected cells (FIG. 44) (n=3, *P<0.01, **P<0.001). FIG. 45 snows TNF-α-mediated production of cellular ROS in ODN-transfected cells. The representative images are shown. Data are means±S.D. of fold increase versus untreated mock cells of the relative DCF fluorescence (n=4, *P<0.05, **P<0.001). FIG. 46 shows JNK and p38 MAPK activation in ODN-transfected cells. Blots are representative blots of three independent experiments. FIG. 47 snows ASK-1 activation in ODN-transfected cells. The kinase activity (KA) was averaged with the values from two independent experiments, and presented as a fold increase of the activity versus the unstimulated and mock-transfected cells (lane 1). FIG. 48 shows TNF-α-induced cell death in mock or ODN-transfected HeLa cells. Data are means±S.D. (n=3, *P<0.01). FIG. 49 shows TNF-α-induced cell death of colon carcinoma cells transfected with ODNs. The level of Hsp60 in subcellular fractions is shown (Upper panel). Data in the graph are means±S.D. (n=3, *P<0.05, **P<0.01). Cell death was analyzed by FACS after staining with, annexin V-fluorescein isothiocynate and propidium iodide.

FIG. 50 shows schematic representation of transgenic vector containing HA-tagged human Hsp60c. FIG. 51 shows identification of two transgenic mouse lines (T4 and T11). Genomic PCR was performed using two different sets of PCR primers, both of which were specific to Hsp60 transgene. The transgenic vector (V) and C57BL/6j (B6) mouse genomic DNA were used as positive and negative control, respectively.

FIG. 52 shows expression of Hsp60c protein in various tissues of transgenic mice. The tissue homogenates were immunoblotted using anti-HA antibody. FIG. 53 shows IKK activation in the liver of control B6 mice or HA-Hsp60c-expressing transgenic mice (T4 and T11) intravenously injected with TNF-α. FIGS. 54 and 55 show DEN-induced cell death in the liver of control and transgenic mice primed with or without TNF-α, as measured by TUNEL assay. The representative images (FIG. 54) are shown. The quantified data in the graph (FIG. 55) are means±S.D. of the number of TUNEL-positive cells per unit area (n=3, *P<0.01 versus paired stimulated one).

In FIGS. 58 and 59, ODN-pretreated BMMs were treated with RANKL (FIG. 58) or TNF-α (FIG. 59) in the presence of M-CSF for 5 days. The TRAP-positive multinucleated osteoclasts were counted as described in Experimental Procedures. Data are means±S.D. of triple experiments of one of two independent experiment sets, and two independent experiment sets snowed similar results (in FIGS. 58 and 59, *P<0.02 and *P<0.001 versus stimulated sense-ODN-transfected cells, respectively), Representative results are shown. In FIG. 60, BMMs were transfected with control or Hsp60c-expresing retrovirus for 2 days. Expression of the indicated proteins was analyzed by immunoblotting. In FIG. 61, BMMs were transfected with indicated retrovirus, and then treated with RANKL in the presence of M-CSF, as described in Experimental Procedures, Data are means±S.D. of triple experiments of one of two independent experiment sets, and two independent experiment, sets showed similar results (*P<0.02 versus control retrovirus-transfected cells), Representative results are shown.

FIG. 62 is a photograph showing the transfection of FITC-conjugated AS-ODN (AS-1) into injured carotid artery. The arrowheads indicate FITC green fluorescence in the neointima. Elastic fibers in the vessel wail generate self-fluorescence. FIG. 63 shows changes in the neointimal thickness of the balloon injured carotid artery transfected with mock or ODNs, as indicated. As described in Experimental Materials and Procedures, carotid arteries were excised and visualized by HE staining. Abbreviations: L, lumen; M, media; Av, adventitia. Arrows indicate neointima. Data of the lower graph represent a percentage of the neointimal thickness to the media area (means±S.D.; n=5; P<0.01). Representative results are shown. FIG. 64 shows apoptotic cell death of smooth muscle cells in the neointima of the injured carotid artery. Carotid arteries were excised, and stained for α-smooth muscle actin and TUNEL. Sections for the detection of cell nuclei were counter-stained with DAPI. Data of the lower graph represent a percentage of the neointimal thickness to the media area (means±S.D.; n=6; P<0.0001). Representative results are shown.

DETAILED DESCRIPTION OF THE PREFERRED EMBODIMENTS

Figure 1:
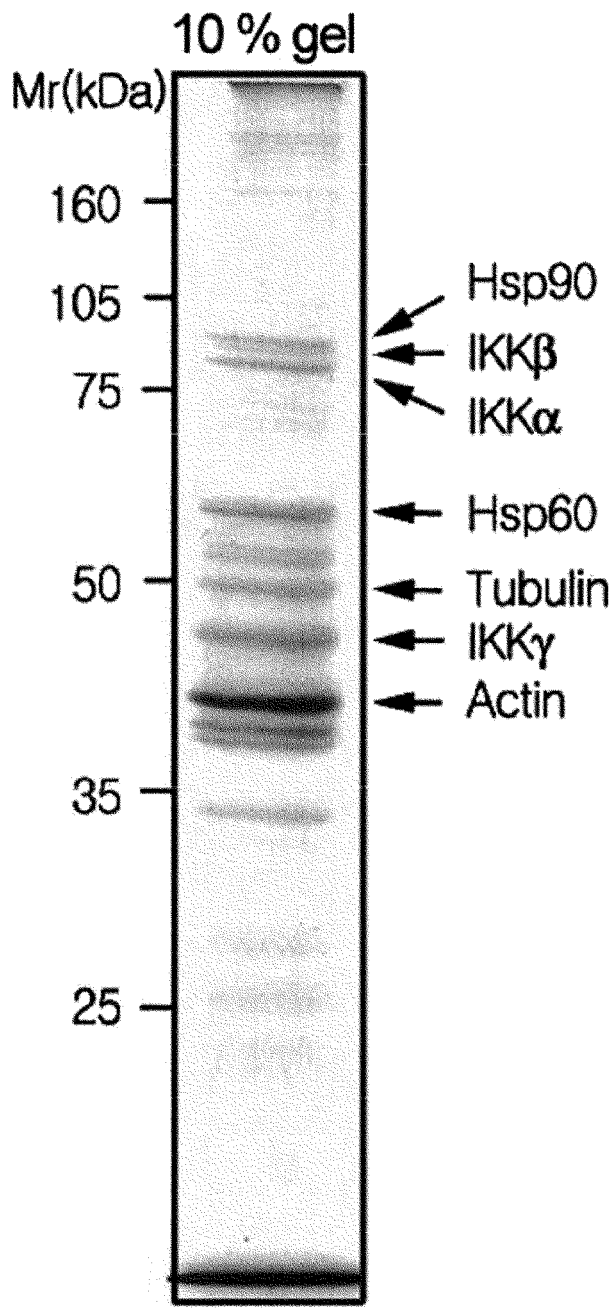
FIGS. 1 to 6 are the results of identification of Hsp60 in IKK complex.

In one aspect of the present invention, the present invention provides a pharmaceutical composition for the prevention or treatment of diseases associated with abnormal cell proliferation, comprising a cytosolic Hsp60 (heat shock protein 60 kDa) inhibitor as an active ingredient.

In general, heat shock protein 60 (Hsp60) is the mitochondrial chaperonin that is involved in refolding of proteins imported from the cytoplasm into the mitochondrial matrix. That is, Hsp60 serves as a chaperonin to help folding of linear amino acid chains into a tertiary structure.

The present inventors demonstrated the novel pro-survival function of cytosolic Hsp60, in which Hsp60 directly interacted with IKKα/β in cytoplasm, independent of its chaperone activity, and then promoted the phosphorylation-dependent activation of the kinase, and subsequently increased transcript ional activity of NF-κB induced survival genes to reduce the intracellular reactive oxygen species (ROS) level, leading to an increase in cell survival against apoptosis-inducing stress. The present inventors have identified that only cytosolic Hsp60 promotes cell survival, while most of the mitochondrial heat shock proteins induce cell death in the cytosol.

The present invention demonstrated for the first time the functions of mitochondria-derived cytosolic Hsp60 protein involved in IKK/NF-κB activation. According to the present invention, cytosolic Hsp60 interacts with IKK complex to be directly involved in the regulation of IKK activation. Subsequent activation of NF-κB pathway activates cell survival response. In the specific embodiment of the present invention, the present inventors demonstrated that in smooth muscle cells, hepatocytes, and osteoclasts, the cytosolic Hsp60 serves as a survival guidance controlling mitochondrial derived ROS through NF-κB target gene expression by directly interacting and regulating IKK activation known to be related to cell survival signaling. Therefore, the present invention provides a pharmaceutical composition for the treatment of diseases associated with abnormal cell proliferation by using a cytosolic Hsp60 inhibitor that inhibits the interaction between Hsp60 and IKK or reduces the cytosolic Hsp60 level. In the present invention, a cytosolic Hsp60 inhibitor is used to control Hsp60's cytosolic level without affecting its mitochondrial level, because a lack of is known to induce functional impairment of mitochondria. Thus the cytosolic Hsp60 inhibitor of the present invention does not affect the mitochondrial level, and it selectively affects cytosolic Hsp60 in the abnormally proliferating cells without affecting normal cells, thereby selectively inducing cell death of abnormally proliferating cells without cytotoxicity in normal cells.

In the preferred embodiment of the present invention, the cytosolic Hsp60 of the present invention interacts with IKK complex, and more preferably, binds with IKKα or IKKβ.

In the preferred embodiment of the present invention, the cytosolic Hsp60 of the present invention promotes serine phosphorylation (Ser178/181) in the T-loop of IKKα/β, leading to activation of IKK complex.

In the preferred embodiment of the present invention, the cytosolic Hsp60 of the present invention activates NF-κB pathway, which induces expression of the NF-κB-dependent survival genes to increase cell survival rate against apoptosis-inducing stress. More preferably, the stress is induced by TNF-α or diethylnitrosamine (DEN).

In the preferred embodiment of the present invention, inhibition of the cytosolic Hsp60 of the present invention causes the increase in the cellular ROS by stress (e.g. TNF-α, DEN), which in turn triggers the sustained activation of c-Jun N-terminal kinase (JNK)/p38 via Apoptosis signal-regulating kinase 1 (ASK-1) and finally induces the cell death.

As used herein, the term "inhibition of the cytosolic Hsp60" encompasses all of the inhibition of cytosolic Hsp60 gene expression and the inhibition of cytosolic Hsp60 protein activity, and preferably inhibition of the cytosolic Hsp60 protein activity, that is, the interaction between cytosolic Hsp60 protein and IKK. More preferably, inhibition of the cytosolic Hsp60 is to inhibit interaction with IKK complex to cause a reduction in serine phosphorylation (Ser178/181) in the T-loop of IKKα/β, which inhibits activation of IKK complex to inhibit or reduce NF-κB signaling. According to the preferred embodiment of the present invention, a cytosolic Hsp60-specific antisense oligodeoxynucleotide-1 (AS-1 ODN, SEQ ID NO. 3) was used to suppress expression of cytosolic Hsp60 protein, and Hsp60 neutralizing antibody (Hsp60N) was used to inhibit interaction of cytosolic Hsp60 protein with IKK complex. As a result, IKK activation and NF-κB transcriptional activation were reduced, and JNK1 was activated (FIGS. 18 to 27).

According to the present invention, inhibition of the cytosolic Hsp60 inhibits IKK complex-mediated NF-κB pathway, and more preferably, IKKα or IKKβ-mediated NF-κB pathway. According to the preferred embodiment of the present invention, inhibition of the cytosolic Hsp60 of the present invention induces inhibition or reduction of intracellular NF-κB signaling so as to reduce expression or activation of downstream signal molecules. This inhibition or reduction of NF-κB signaling inhibits expression of genes involved in mitochondrial protection, thereby reducing cell survival rate.

According to the preferred embodiment of the present invention, the cytosolic Hsp60 of the present invention reduces the mitochondrial derived ROS level via expression of NF-κB-dependent survival genes. In the specific embodiment of the present invention, ablation of cytosolic Hsp60 results in the increase of cellular ROS, which in turn triggers the sustained activation of JNK/p38 via ASK-1 and finally induces the cell death, in response to TNF-α.

As described above, inhibition of the cytosolic Hsp60 of the present invention inhibits IKK/NF-κB activation, leading to a reduction in cell survival rate. This inhibition of IKK/NF-κB activation reduces expression of NF-κB-dependent survival genes, thereby exhibiting various pharmaceutical activities. More particularly, inhibition of the cytosolic Hsp60 of the present invention affects IKK activation to inhibit NF-κB signaling, which reduces expression of survival genes such as MnSOD and Bfl-1/A1 and increases cellular ROS level, resulting in cell death. Since Bfl-1/A-1 functions as a tBid and Bak antagonist [Wang C Y et al., Mol Cell Biol 19:5923-5929 (1999)] and MnSOD eliminates the superoxide anion inside mitochondria [Wong G H et al., Cell 58:923-931 (1989)], these two genes are ultimately critical for controlling mitochondrial-derived ROS.

The cytosolic Hsp60 inhibitor included as an active ingredient in the composition of the present invention includes antisense oligonucleotides, siRNA oligonucleotides, antibodies, single-chain variable fragments, peptides, aptamers, low-molecular weight compounds, and natural extracts, but is not limited thereto.

Preferably, the inhibitor of cytosolic Hsp60 protein expression is an Hsp60 mRNA- specific antisense oligonucleotide or siRNA oligonucleotide, more preferably, an antisense oligonucleotide, and most preferably, an antisense oligodeoxynucleotide (ODNs).

As used herein, the term "antisense oligonucleotide" refers to DNA, RNA or its derivatives that include oligonucleotide sequences complementary to the sequences of a specific mRNA, and they bind to the complementary sequences in mRNA and interfere with its translation to protein. The Hsp60-specific antisense sequence means DNA or RNA sequences that is complementary and binds to Hsp60 mRNA, that are able to inhibit translation, cytosolic translocation, maturation or other biological functions of Hsp60 mRNA. Preferably, constructed is an antisense oligodeoxynucleotide (AS-ODN) complementary to human Hsp 60 open reading frame (ORF) sequence (SEQ ID NO. 1 or SEQ ID NO. 2). More preferably, a sequence surrounding the start codon of ORF is targeted, and if necessary, sequences with high Tm values targeting all regions in ORE may be included for construction. In the specific embodiment of the present invention, an antisense oligonucleotide complementary to the region spanning from, start, codon to the 3' end of ORE was designed and used. The antisense oligonucleotide is 6 to 100 nucleotides, preferably 8 to 60 nucleotides, more preferably 10 to 40 nucleotides, much more preferably 10 to 25 nucleotides, and most preferably 12 to 20 nucleotides in length. AS-1 ODN (SEQ ID NO. 3) used in the specific embodiment of the present invention targets mitochondrial targeting signal (MTS)-encoding region of Hsp60 mRNA transcript. AS-2 ODN (SEQ ID NO, 4) used in the specific embodiment of the present invention targets the region (+95-+110 from start codon) near the 5' end, but after MTS sequence of Hsp60 ORF, in order to exclude off-target effect. In order to examine whether the objects of the present invention can be achieved by antisense oligonucleotides targeting all regions in ORF, antisense oligodeoxynucleotides of SEQ ID NO. 5 (AS-3 ODN), SEQ ID NO. 6 (AS-4 ODN) and SEQ ID NO. 7 (AS-5 ODN) specific to the downstream sequences of the AS-2 ODN target sequence were constructed and used.

Since the antisense oligodeoxynucleotide is a moderate translational blocker, it did not elicit the reduction of total Hsp60 level. However, Hsp60 once located in the cytosol exhibited short half-life and the faster turnover compared to the mitochondrial one. Consequently, the cytosolic Hsp60 level is reduced by treatment of the antisense oligonucleotide of the present invention.

The antisense oligonucleotide may have at least one modification in its base, sugar or backbone for its higher efficacy (De Mesmaeker et al., Curr Opin Struct Biol., 5(3): 343-55 (1995)). The oligonucleotide backbone may be modified by phosphorothioate, phosphotriester, methyl phosphonate, short chain alkyl, cycloalkyl, short chain heteroatomic or heterocyclic intersugar linkages. The antisense oligonucleotide may also include one or more substituted sugar moieties. The antisense oligonucleotide may include one or more modified bases, for example, hypoxanthine, 6-methyladenine, 5-me pyrimidines (particularly, 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. The antisense oligonucleotide of the present invention is also chemically linked to one or more moieties or conjugates which enhance the activity and cellular uptake of the antisense oligonucleotide. Such moieties include, but are not limited to, lipophilic moieties such as a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety. Methods for preparing such oligonucleotides including the lipophilic moieties are known in the art (U.S. Pat. Nos. 5,138,045, 5,218,105 and 5,459,255). The modified oligonucleotides described above enhance stability against nuclease degradation and increase affinity of the antisense oligonucleotide toward its target mRNA.

The antisense oligonucleotide is conventionally synthesized in vitro and then transmitted to cells, or is intracellularly produced. In vitro synthesis of antisense oligonucleotide involves RNA polymerase I. In vivo synthesis of antisense RNA is exemplified by transcription of antisense RNA using a vector having origin of recognition region, MCS in opposite orientation. The antisense RNA preferably includes a translation stop codon for inhibiting translation to peptide.

The antisense oligonucleotide to be used in the present invention can be designed with reference to human Hsp60 mRNA sequences known in the art. As described above, the antisense oligonucleotide of the present invention can be designed with a sequence complementary to coding sequence (CDS) of human Hsp60 mRNA, a sequence complementary to the start codon and its surrounding sequence, a sequence complementary to 5'-UTR and a sequence complementary to 3'-UTR. In the specific embodiment of the present invention, an antisense oligonucleotide complementary to the region spanning from start codon to the 3' end of ORF was designed and used. Detailed description of the design and synthesis of the antisense oligonucleotide of the present invention is disclosed in the literature [Weiss, B. (ed.): Antisense Oligodeoxynucleotides and Antisense RNA: Novel Pharmacological and Therapeutic Agents, CRC Press, Boca Raton, Fla., 1997; Weiss, B., et al., Cell. Mol. Life. Sci., 55:334-358 (1999)], which is incorporated herein by reference.

As used herein, the term "siRNA" refers to an oligonucleotide molecule capable of mediating RNA interference or gene silencing (see WO 00/44895, WO 01/36646, WO 99/32619, WO 01/29058, WO 99/07409 and WO 00/44914). Since siRNA can suppress the expression of the target gene, it provides an effective way of gene knockdown or genetic therapy. First discovered in plants, worms, fruit flies and parasites, siRNA has been recently developed and used for studies of mammal cells.

When siRNA molecule is used in the present invention, it may have a structure in which its sense strand, that is, a sequence corresponding to the Hsp60 mRNA sequence and its antisense strand, that is, a sequence complementary to the Hsp60 mRNA sequence form a double strand. Alternatively, it may have a single-stranded structure having self-complementary sense and antisense strands.

The siRNA is not limited to those in which double-stranded RNA moieties constitute complete pairs, but includes the unpaired moieties such as mismatch (corresponding bases are not complementary), bulge (no base in one chain), etc. Preferably, siRNA complementary to a sequence surrounding the start codon of the human Hsp60 ORF is constructed. The total length of the siRNA may be 10 to 100 bases, preferably 15 to 80 bases, and more preferably 20 to 70 bases.

The end of the siRNA may be either blunt or cohesive as long as it is capable of suppressing the expression of the Hsp60 gene via RNA interference (RNAi). The cohesive end may be either 3'-or 5'-end.

In the present invention, the siRNA molecule may have a short nucleotide sequence (e.g., approximately 5-15 nucleotides) inserted between the self-complementary sense: strands and antisense strands. In this case, the siRNA molecule formed from the expression of the nucleotide sequence forms a hairpin structure via intramolecular hybridization, resulting in a stem-and-loop structure overall. The stem-andloop structure is processed in vitro or in vivo to give an activated siRNA molecule capable of mediating RNAi.

In the present invention, the cytosolic Hsp60 inhibitor, in particular, the activity inhibitor is preferably an antibody, a single-chain variable fragment, a peptide, a low-molecular weight compound, or a natural extract which specifically binds to Hsp60.

The antibody used in the present invention, which specifically binds to Hsp60 protein to inhibit its activity, is a polyclonal or monoclonal antibody. Antibodies against Ksp60 protein may be prepared by a method typically known in the art, for example, a fusion method (Kohler et al., European Journal of Immunology, 6:511-519 (1976)), a recombinant DNA method (U.S. Pat. No. 4,816,56) or a phage antibody library technique (Clackson et al, Nature, 352:624-628(1991) and Marks et al., J. Mol. Biol., 222:58, 1-597(1991)). The general procedures for antibody production are described in detail in [Harlow, E. et al., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, NY, 1991], the teachings of which are incorporated herein by reference in their entity. For example, the preparation of hybridoma cells for monoclonal antibody production may be done by fusion of an immortal cell line and the antibody-producing lymphocytes, which can be achieved easily by techniques well known in the art. Polyclonal antibodies may be prepared by injecting Hsp60 protein antigen to a suitable animal, collecting antiserum from the animal, and isolating antibodies employing a known affinity technique. In one embodiment of the present invention, binding of cytosolic Hsp60 to IKK was inhibited by using polyclonal neutralizing antibodies that specifically bind to Hsp60 protein to form cytosolic Hsp60 aggregates.

In the present invention, the antibody may include a single-chain variable fragment (scFv). The single-chain variable fragment may consist of "light chain variable region (VL)-linker-heavy chain variable region (VH)". The linker means an amino acid sequence having a predetermined length, which functions to artificially link the variable regions of heavy and light chains.

As used herein, the term "peptide" means a linear or circular, preferably linear molecule formed by linkage between amino acid residues via peptide bond. The peptide of the present invention may be prepared by chemical synthesis method known in the art, particularly solid-phase synthesis techniques (Merrifield, J. Amer. Chem., Soc. 85: 2149-2154 (1963); Stewart, et al., Solid Phase Peptide Synthesis, 2nd. ed., Pierce Chem. Co.: Rockford, 111(1984)). The peptide that specifically binds to Hsp60 to inhibit Hsp60 activity may be obtained by the typical method known in the art, for example, a phage: display method (Smith G P, Science 228 (4705):1315-1317 (1985); Smith G P, Petrenko V A, Chem. Rev. 97 (2): 391-410 (1997)). The peptide may be a peptide having 4-40, preferably 5-30, more preferably 5-20, and most preferably 8-15 amino acid residues. The peptide may be linear or circular.

Stability of the peptide of the present invention may be further enhanced by modification of amino acid residues, According to the preferred embodiment of the present invention, the stability of the peptide is increased by modification at any amino acid residue, preferably the N-terminal with Gly residue(s), acetyl group, fluorenyl methoxy carbonyl group, formyl group, palmitoyl group, myristyl croup, stearyl group or polyethylene glycol (PEG), and most preferably Gly residue is).

In the case where Gly residue (s) is further bound to the N-terminal of the peptide of the present invention, the number of the Gly residue is in a range of 1-8, preferably 2-6, more preferably 2-4 and most preferably 3.

As used herein, the term "aptamer" refers to an oligonucleotide molecule having a binding affinity for a particular target molecule. The aptamer can also inhibit the activity of a particular target molecule by binding to the particular target molecule. The aptamer of the present invention may be an RNA, a DNA, a modified oligonucleotide or a mixture thereof. The aptamer may be also in a linear or circular form. The length of the aptamer of the present invention is not particularly limited, and may be usually approximately 15 to approximately 200 nucleotides, and may be, for example, approximately 100 nucleotides or less, preferably approximately 30 nucleotides or less, more preferably approximately 60 nucleotides or less, and most preferably approximately 45 nucleotides or less. The length of the aptamer of the present invention may be, for example, approximately 18, 20 or 25 nucleotides or longer. If the total number of nucleotides is smaller, chemical synthesis, chemical modification, and mass-production will be easier, and there is a major advantage in terms of cost, stability in the body is high, and toxicity is low.

The aptamer of the present invention may be prepared by utilizing the SELEX method or an improved version thereof [e.g., Ellington et al., Nature, 346, 818-822(1990); Tuerk et al., Science, 249, 505-510(1990)], The SELEX method is a method by which an oligonucleotide that binds specifically to a target substance is selected from 10-14 oligonucleotide pools having different nucleotide sequences. The oligonucleotide used in the present invention has a structure in which a random sequence of about 40 residues is sandwiched by primer sequences. This oligonucleotide pools are allowed to associate with a target substance, and only the oligonucleotide that has bound to the target substance is recovered using a filter or the like and is amplified by RT-PCR, and this is used as the template for the next round. By repeating this operation about 10 times, an aptamer that binds specifically to the target substance can be acquired. In the SELEX method, by increasing the number of rounds or using a competing substance, an aptamer exhibiting a stronger binding force for the target substance is concentrated and selected. Hence, by adjusting the number of rounds of SELEX, and/or changing the competitive condition, aptamers with different binding forces, aptamers with different binding modes, and aptamers with the same binding force and binding mode but different base sequences can be obtained in some cases. The SELEX method includes a process of amplification by PCR; by causing a mutation using manganese ions or the like in the process, it is possible to perform SELEX with higher diversity.

Further, aptamers may be selected against complex targets, that, is, live cells and tissues, using the cell-SELEX technique in addition to the prior SELEX technique (Guo et al., Int. J. Moi. Sci., 9(4): 668, (2008)). The cell-SELEX technique has an advantage in that it allows the development of aptamers for diseased cells even when surface marker targets are unknown. In addition, the cell-SELEX technique is more advantageous over the prior SELEX technique, because target proteins cannot show their original properties in their isolated state, and thus target proteins which are in a physiological state allow a more functional approach during a selection process.

Meanwhile, the aptamer binds to the target substance in a wide variety of binding modes, such as ionic bonds based on the negative charge of the phosphate group, hydrophobic bonds and hydrogen bonds based on ribose, and hydrogen bonds and stacking bonds based on oligonucleotide bases. In particular, ionic bonds based on the negative charge of the phosphate group, which are present in the same number as the number of constituent nucleotides, are strong, and bind to lysine and arginine being present on the surface of the positive charge of protein. For this reason, oligonucleotides not involved in the direct binding to the target substance can be substituted. In particular, because the region of stem structure has already formed base pairs and faces the inside of the double helical structure, oligonucleotide bases are unlikely to bind directly to the target substance. Therefore, even when a base pair is replaced with another base pair, the activity of the aptamer often does not decrease. In structures, in which no base pairs are formed, such as loop structures, provided that the oligonucleotide base is not involved in the direct binding to the target molecule, base substitution is possible. For example, it may be a nucleotide in which a hydroxyl group is substituted by any atom or group at the 2' position of ribose. As examples of any such atom or group, a nucleotide substituted by a hydrogen atom, a fluorine atom or an —O—alkyl group (e.g., —O—$CH_3$), an —O-acyl group (e.g., —O—CHO), or an amino group (e.g., —$NH_2$) can be mentioned. The aptamer, unless the functional group involved in the direct binding to the target molecule is substituted or deleted, often retains the activity thereof.

Further, aptamers are easily alterable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. An aptamer with the predicted new sequence can be chemically synthesized with ease, and it can be determined whether or not the aptamer retains the activity using an existing assay system.

The aptamer of the present invention may be one in which a sugar residue (e.g., ribose) of each nucleotide has been modified to increase the binding activity, stability, drug deliverability and the like. As examples of the site to be modified in a sugar residue, one having the oxygen atom at the 2'-position, 3'-position and/or 4'-position of the sugar residue replaced with another atom or the like may be mentioned. As examples of the modification, fluoration, O-alkylation (e.g., O-methylation, O-ethylation), O-arylation, S-alkylation (e.g., S-methylation, S-ethylation), S-arylation, and amination (e.g., —NH) may be mentioned. Such alterations in the sugar residue may be performed by a method known in the art (e.g., see Sproat et al., Nucle. Acid. Res. 19, 733-738, (1991); Cotton et al., Nucl. Acid, Res. 19, 2629-2635, (1991); Hobbs et al., Biochemistry 12, 5138-5145, (1973)).

The aptamer of the present invention may also have an oligonucleotide base (e.g., purine or pyrimidine) altered (e.g., chemical substitution) to increase the binding activity or the like. As examples of such alterations, 5-position pyrimidine alteration, 6- and/or 8-position purine alteration, alteration with an extracyclic amine, substitution with 4-thiouridine, and substitution with 5-bromo or 5-iodo-uracil can be mentioned.

The phosphate group contained in the aptamer of the present invention may be altered to confer resistance to nuclease and hydrolysis. For example, the P(O)O group may be substituted with P(O)S (thioate), P(S)S (dithioate), P(O)$NR_2$ (amidate), P(O)R, R(O)OR', CO or Chb (formacetal) or 3'-amine (—NH—$CH_2$—$CH_2$—) [wherein each unit of R or R' is independently H or a substituted or unsubstituted alkyl (e.g., methyl, ethyl)]. The joining group is, for example, —O—, —N— or —S—, and nucleotides can bind to an adjoining nucleotide via these joining groups.

The alterations may also include alterations such as capping at 3' and 5'. An alteration may be further performed by adding to an end a polyethyleneglycol, an amino acid, a peptide, an inverted dT, an oligonucleotide, a nucleoside, myristoyl, lithocolic-oleyl, docosanyl, lauroyl, stearoyl, palmitoyl, oleoyl, linoleoyl, other lipid, steroid, cholesterol, caffeine, vitamin, a pigment, a fluorescent substance, an anti-cancer agent, a toxin, an enzyme, a radioactive substance, biotin or the like. For such alterations, for example, please refer to U.S. Pat. Nos. 5,660,985 and 5,756,703.

In addition, aptamers are attached to the surface of liposomes or nanoparticles, thereby selectively delivering anti-cancer agents, toxins, tumor suppressor genes, siRNA or the like encapsulated in the liposomes or nanoparticles to target cells.

The low-molecular weight compound or natural extract that inhibits Hsp60 activity can be easily obtained by the following screening method.

Most preferably, the active ingredient used in the composition of the present invention is an antisense oligonucleotide targeting Hsp60. Detailed description of the antisense oligonucleotide is the same as described above.

When the antisense oligonucleotide is used for the treatment of the target disease, the antisense oligonucleotide must be transported into cells. The method of transporting the antisense oligonucleotide may be performed by various methods known in the art. For example, antisense oligonucleotides are encapsulated in liposomes and transported into cells using various substances known in the art. In addition, antisense oligonucleotides may be linked to suitable cell penetration peptide (CPPs) and transported into cells. CPPs may include a variety of CPPs known in the art, and for example, penetratin peptide, Tat peptide of HIV-1, transportan peptide, Buforin II peptide, model amphipathic peptide (MAP), k-FGF peptide, prion peptide, pVEC peptide, pep-1 peptide, SynB1 peptide, pep-7 peptide, HN-1 peptide, arginine polymer-containing peptide, Antennapedia or penetratin (Antp) peptide, Mph-1 peptide, VP22 peptide of HSV-1, and HP4 peptide of herring protamine, but are not limited thereto.

According to the preferred embodiment of the present invention, the composition of the present invention is a pharmaceutical composition including (a) a pharmaceutically effective amount of the above described cytosolic Hsp60 inhibitor of the present invention; and (b) a pharmaceutically acceptable carrier.

As used herein, the term "pharmaceutically effective amount" refers to an amount of the above described inhibitor which is sufficient for the inhibition of cytosolic Hsp60 expression or activity.

When the composition of the present invention is prepared as a pharmaceutical composition, it includes a pharmaceutically acceptable carrier. The pharmaceutically acceptable carriers included in the pharmaceutical composition of the present invention are those generally used in pharmaceutical formulations, and may include lactose, dextrose, sucrose, sorbitol, mannitol, starch, acacia gum, calcium phosphate, alginate, gelatin, calcium silicate, micro-crystalline cellulose, polyvinyl pyrrolidone, cellulose, water, syrup, methyl cellulose, methylhydroxybenzoate, propylhydroxybenzoate, talc, magnesium stearate and mineral oil, but are not limited thereto. In addition to the above ingredients, the pharmaceutical composition of the present invention may further include a lubricant, a wetting agent, a sweetener, a fragrance, an emulsifier, a suspending agent, a preservative or the like. Suitable pharmaceutical acceptable carriers and formulation thereof are described in detail in Remington's Pharmaceutical Sciences (19th ed., 1995).

According to another aspect, the present invention relates to a method for treating diseases associated with abnormal cell proliferation, comprising the step of administering to a subject the pharmaceutical composition including the cytosolic Hsp60 inhibitor or the active ingredient thereof. The administration may be oral or parenteral administration, and the parenteral administration may include intravenous, subcutaneous, intramuscular, intraperitoneal, percutaneous, mucosal, and ocular routes.

Adequate dose of the pharmaceutical composition of the present invention may be determined according to various factors, including formulation methods, administration modes, patient's age, weight, sex, pathological conditions and diet, administration periods, administration routes, excretion rates and reaction sensitivity. Preferably, the dose of the pharmaceutical composition of the present invention is 0.001-1000 mg/kg body weight in the case of adult patients.

The pharmaceutical composition of the present invention may be formulated by using pharmaceutically acceptable carriers and/or excipients so that it may be provided as a unit dosage form or may be packed in a multi-dose container in a manner generally known to those skilled in the art. Such dosage forms include a solution, a suspension, a syrup, or an emulsion in oil or aqueous media, or an elixir, powder, flour, granule, tablet, or capsule formulation, and may further include a dispersant or stabiliser.

As used herein, the term 'diseases associated with abnormal cell proliferation' means diseases caused by abnormal cell proliferation, and are exemplified by cancer, inflammatory diseases, hyperproliferative vascular disorders or the like.

According to the preferred embodiment of the present invention, the 'cancer' of the present invention refers to a malignant tumor caused by unlimited cell proliferation in the tissue, and the cancer that can be prevented or treated by using the composition of the present invention include brain cancer, neuroendocrine carcinoma, gastric cancer, lung cancer, breast cancer, ovarian cancer, liver cancer, bronchial cancer, nasopharyngeal cancer, laryngeal cancer, pancreatic cancer, renal cancer, bladder cancer, adrenal gland cancer, rectal cancer, colon cancer, cervical cancer, prostate cancer, bone cancer, skin cancer, thyroid cancer, parathyroid cancer, and ureteral cancer, but is not limited thereto.

According to the preferred embodiment of the present invention, the 'inflammatory diseases' of the present invention encompass all diseases that cause inflammation, and inflammation occurs when immunologically competent cells are activated in response to foreign organisms or antigenic proteins. The inflammatory process can be either beneficial, as when it causes invading organisms to be phagocytosed or neutralized, but it also can be deleterious, as in the case of arthritis, when it leads to the destruction of bone and cartilage and the resulting limitation of joint function. The inflammatory response is usually triggered by a trauma or antigens, such as viral, bacterial, protozoal, or fungal antigens.

The inflammatory diseases that can be prevented or treated according to the present invention include: inflammation-induced bone diseases, degenerative arthritis, diabetes, inflammatory myositis, arteriosclerosis, stroke, hepatocirrhosis, encephalitis, celiac disease, cholelithiasis, nephrolith, sinusitis, rhinitis, conjunctivitis, asthma, dermatitis, inflammatory bowel disease, inflammatory collagen vascular diseases, glomerulonephritis, inflammatory skin diseases, and sarcoidosis, but are not limited thereto. More preferably, the inflammatory diseases of the present invention may include a) rheumatoid inflammatory diseases such as degenerative arthritis, systemic lupus erythematosus, ankylosing spondylitis, Behcet's disease and inflammatory myositis, b) inflammatory bowel disease such as ulcerative colitis and Crohn's disease, c) skin inflammatory diseases such as psoriasis, atopic dermatitis, contact dermatitis, eczematous dermatitis, seborrheic dermatitis, lichen planus, lichen simplex chronicus, pemphigus, bullous pemphigoid, epidermolysis bullosa, urticaria, angioedema, vasculitis, erythema or eosinophilia, nummular dermatitis, generalized exfoliative dermatitis, stasis dermatitis, hair follicles and sebaceous gland diseases including acne, inflammatory response including perioral dermatitis, razor bumps and drug eruption, erythema multiforme, erythema nodosum, and granuloma annulare; and d) celiac disease, encephalitis, pelvic inflammatory disease (PID), but are: not limited thereto.

According to the preferred embodiment of the present invention, the 'inflammation-induced bone diseases' of the present invention include osteogenesis disorders, bone fracture, senile bone loss, chondrodystrophy, hypercalcemia, hyperostosis, osteogenesis imperfecta, osteomalacia, osteomyelitis, osteoporosis, Paget's disease, osteoarthritis, or rickets, but are not limited thereto.

According to the preferred embodiment of the present invention, the 'hyperproliferative vascular disorders' of the present invention means disorders or diseases caused by hyperproliferation of cells present in blood vessels, particularly, vascular smooth muscle cells. The hyperproliferative vascular disorders include a variety of diseases, for example, arteriosclerosis, atherosclerosis, restenosis and stenosis, vascular malformation, hemodialysis vascular access stenosis, transplant arteriopathy, vasculitis, vascular inflammation, DiGeorge syndrome, hereditary hemorrhagic telangiectasia. (HHT), cavernous hemangioma, keloid scar, pyogenic granuloma, blistering disease, Kaposi sarcoma, hyperproliferative vitreous syndrome, retinopathy of prematurity, choroidal neovascularization, macular degeneration, diabetic retinopathy, ocular neovascularization, primary pulmonary hypertension, asthma, nasal polyps, inflammatory bowel and periodontal diseases, seroperitoneum, peritoneal adhesion, contraception, endometriosis, uterine bleeding, ovarian cysts, ovarian hyperstimulation, arthritis, rheumatoid arthritis, chronic rheumatism, synovitis, osteoarthritis, osteomyelitis, osteophyte formation, septicemia, vascular leak syndrome, cancer, infectious diseases, or autoimmune diseases. Preferably, the hyperproliferative vascular disorder of the present invention is arteriosclerosis, atherosclerosis, restenosis or stenosis. Atherosclerosis is a disease: caused by an accumulation of fatty materials in or fibrosis of the inner linings of arteries. Meanwhile, restenosis is a disease that blood vessel's passage is narrow after traumatization is generated in a blood vessel wail. It has been known that vascular restenosis generated after arteriosclerosis progress and stent insertion is caused by proliferation and migration of vascular smooth muscle cells, and secretion of extracellular matrix (Circulation, 95, 1998-2002, (1997); J. Clin. Invest. 99, 2814-2816, (1997); Cardiovasc. Res. 54, 499-502, (2002)). Thereafter, there have been enormously made studies for drug inhibiting vascular smooth muscle cell proliferation to prevent artheriosclerosis development and vascular restenosis (J. Am. Coll. Cardiol., 39, 183-193, (2002)).

In the 'prevention or treatment' of the present invention, the term 'prevention' means all of the actions in which the occurrence of any disease caused by the increased activation of cytosolic Hsp60 protein is restrained or retarded by the administration of the pharmaceutical composition including the cytosolic Hsp60 inhibitor, and the term 'treatment' means all of the actions in which any disease caused by the increased activation of cytosolic Hsp60 protein has taken a turn for the better or been modified favorably by the administration of the pharmaceutical composition.

Figure 49:
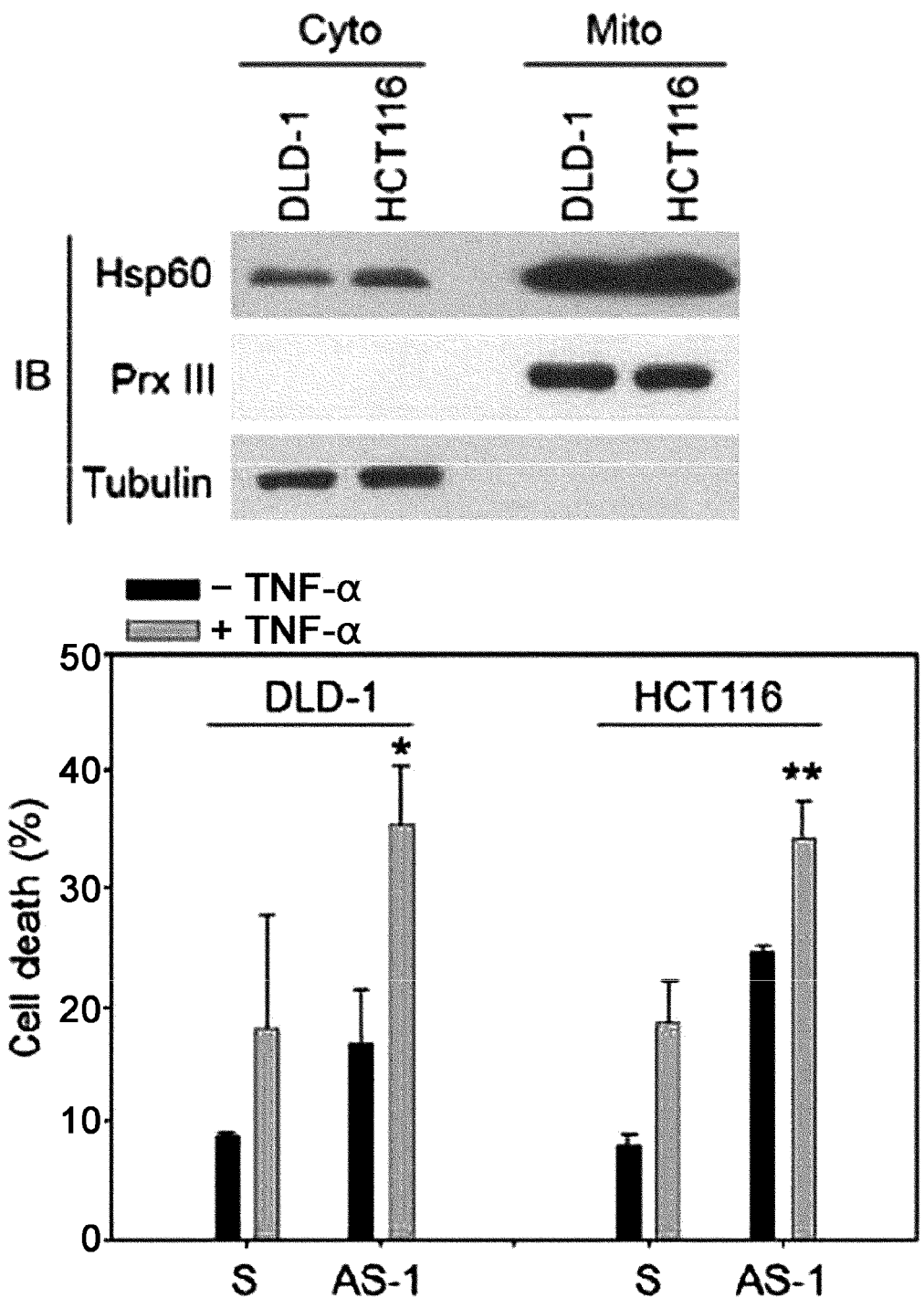

In the specific embodiment of the present invention, Hsp60 AS-ODN as the cytosolic Hsp60 inhibitor enhanced TNF-α-induced cell death in colon carcinoma cell lines, which showed significant level of cytosolic Hsp60 (FIG. 49).

In the specific embodiment of the present invention, the present inventors also investigated whether Hsp60 AS-ODN is able to inhibit NF-κB-dependent inflammatory responses in vivo. More specifically, recent studies reported that IKK-mediated NF-κB pathway is essential for receptor activator of nuclear factor-κB (RANK)-induced osteoclastogenesis. Therefore, the present inventors demonstrated the effects of Hsp60 AS-ODN on osteoclast differentiation regarding inflammation-induced bone loss.

Two main types of cells are responsible for bone renewal: one is an osteoblast involved in bone formation and the other is an osteoclast involved in breakdown of bone. The osteoblast produces RANKL and its decoy receptor, ORG (osteoprotegerin). RANKL binds to receptor activator of nuclear factor-κB (RANK) which is a receptor on the surface of osteoclast progenitor cells, leading to maturation of osteoclast progenitor and bone resorption. However, the binding of OPG to RANKL inhibits the binding between RANKL and RANK; this, in turn, prevents osteoclast formation and excessive bone resorption (Theill L E. et al., Anna Rev Immunol., 20, pp. 795-823, (2002); Wagner E E. et al., Curr Opin Genet Dev., 11, pp. 527-532, (2001)). The resorption or breakdown of old bone is initiated by osteoclasts originating from blood cells (hematopoietic stem cells), which produce pores in the bone and release a small amount of calcium into bloodstream to be used for maintaining body functions (William J. et al., Nature., 423, pp. 337342, (2003)).

As a result, the cytosolic Hsp60 inhibitor of the present invention that interacts with IKK complex remarkably reduced formation of RANKL or TNF-α-induced multinucleated tartrate-resistant acid phosphatase (TRAP)-positive osteoclasts. In addition, ectopic expression of cytosolic Hsp60 clearly increased formation of TRAP-positive osteoclasts in response to RANKL. These results indicate that cytosolic Hsp60 induces expression of superoxide dismutase 2 (SOD2) via IKK/NF-κB signaling to promote: osteoclast survival, and thus bone diseases including inflammation-induced bone loss can be treated by inhibition of cytosolic Hsp60 (FIGS. 58 to 61).

Figure 62:
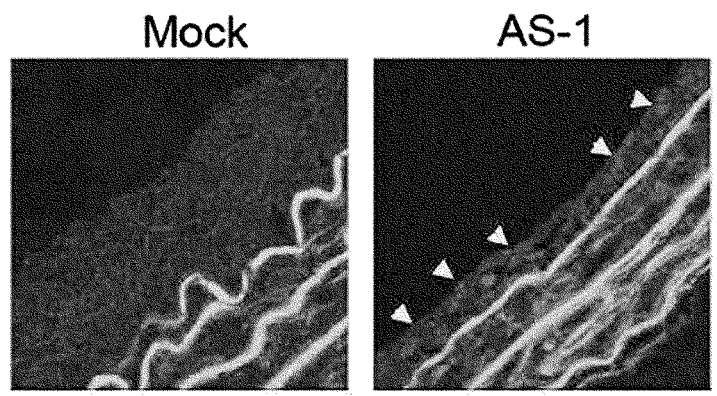
FIGS. 62 to 64 show that ablation of cytosolic Hsp60 causes apoptotic cell death of smooth muscle cells in the neointima of the balloon injured vessels.
Figure 63:
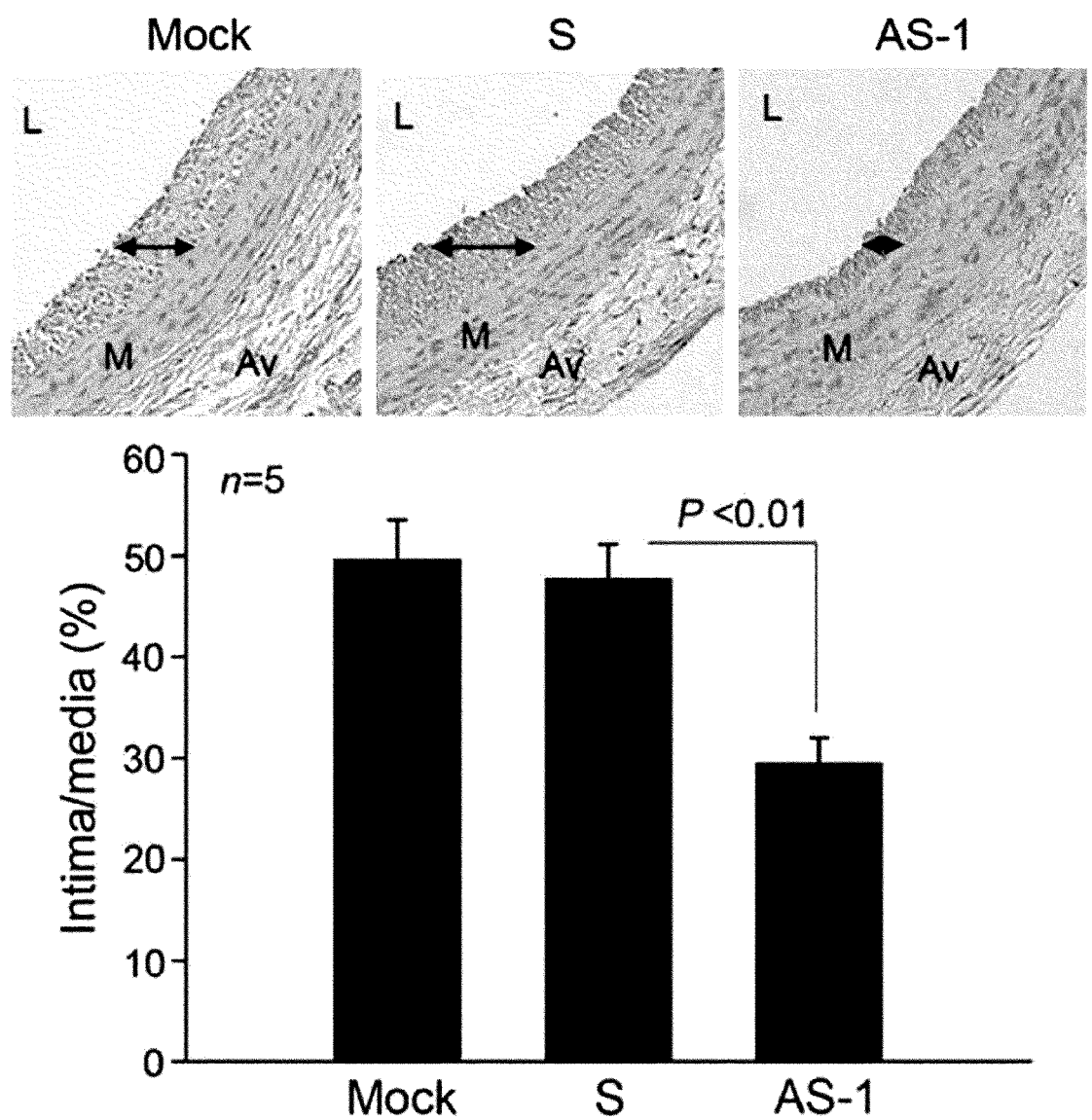
Figure 64:
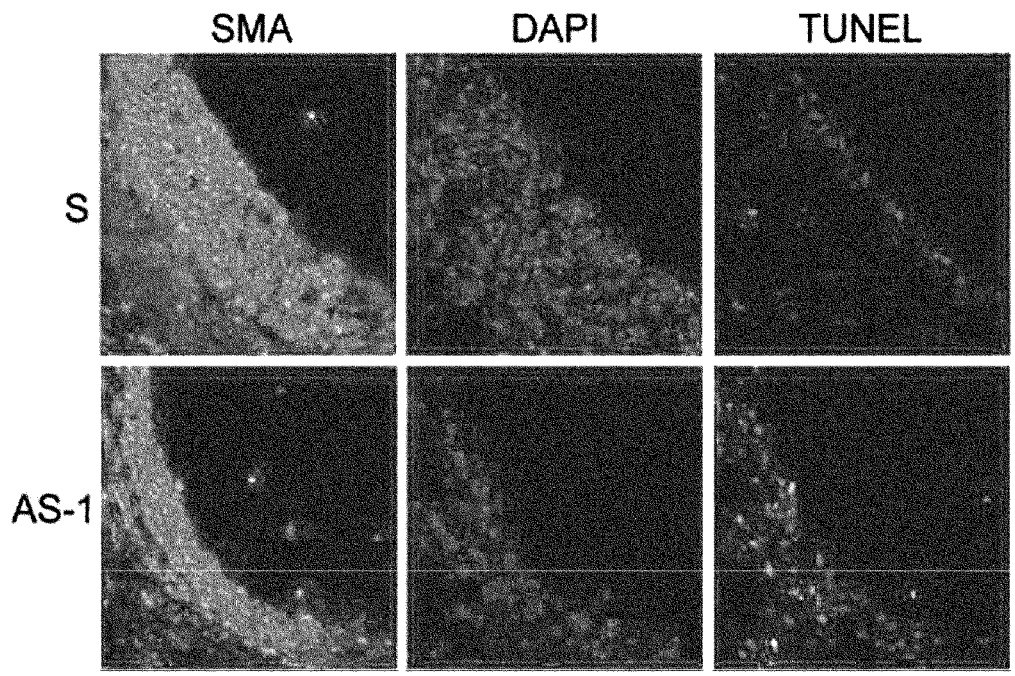
Figure 64:
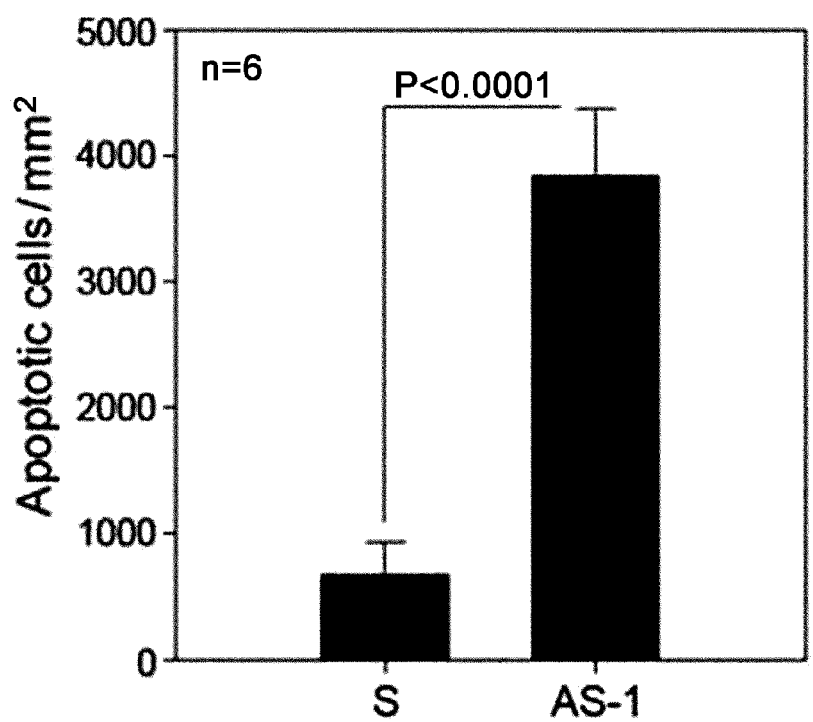

Further, in the specific embodiment of the present invention, inhibition of cytosolic Hsp60 by Hsp60 AS-ODN of the present invention reduced growth of neointimal thickness by proliferative smooth muscle cells in injured carotid artery to approximately 50%, and the reduction of neointimal thickness was induced by apoptotic cell death (FIGS. 62 to 64). Therefore, the cytosolic Rsp60 inhibitor of the present invention that very effectively inhibits proliferation of vascular smooth muscle cells is very useful for the treatment of hyperproliferative vascular disorders.

According to still another aspect of the present invention, the present invention provides a method for screening a therapeutic agent for diseases associated with abnormal cell proliferation, comprising the steps of:
(a) treating a cytosolic Ksp60 gene-containing cell with a test material;
(b) analyzing expression of the cytosolic Hsp60; and
(c) determining that the test material is a therapeutic agent for diseases associated with abnormal cell proliferation when it reduces the level of the cytosolic Ksp60.

According to still another aspect of the present invention, the present invention provides a method for screening a therapeutic agent for diseases associated with abnormal cell proliferation, comprising the steps of:
(a) treating with a test material a cell or a cell extract that contains cytosolic Hsp60 protein, or cytosolic Hsp60 protein and IκB kinase (IKK) protein;
(b) analyzing whether the test material binds to cytosolic Hsp60 protein, or whether the test material inhibits binding of cytosolic Hsp60 protein and IKK protein; and
(c) determining that the test material is a therapeutic agent for diseases associated with abnormal cell proliferation when it binds to cytosolic Hsp60 protein, or it inhibits binding of cytosolic Hsp60 protein and IKK protein. The cell may be a cell extract. In this case, the cytosolic Hsp60 protein may be any one of cytosolic Hsp60 separated from or cytosolic Hsp60 protein included in the cells.

The screening method of the present invention may be performed by various methods, and particularly, it may be performed in a high-throughput manner using various known binding assay techniques.

In the screening method of the present invention, the test material or the cytosolic Hsp60 protein may be labeled with a detectable label. For example, the detectable label may be a chemical label (e.g., biotin), an enzymatic label (e.g., horseradish peroxidase, alkaline phosphatase, peroxidase, luciferase, β-galactosidase and β-glucosidase), a radioactive label (e.g., $C^{14}$, $I^{125}$, $P^{32}$ and $S^{35}$), a fluorescent label [e.g., coumarin, fluorescein, fluorescein Isothiocyanate (FITC), rhodamine 6G, rhodamine 3,6-carboxy-tetramethylrhodamine (TAMRA), Cy-3, Cy-5, Texas Red, Alexa Fluor, 4,6-diamidino-2-phenylindole (DAPI), HEX, TET, Dabsyl and FAM], a luminescent label, a cbemiluminescent label, a fluorescence resonance energy transfer (FRET) label, or a metal label (e.g., gold and silver).

When the cytosolic Hsp60 protein or the test material is labeled with the detectable label, the binding between the cytosolic Hsp60 protein and the test material may be analyzed by detecting signals from the label. For instance, when alkaline phosphatase is used as the label, signals are detected using a chromogenic substrate such as bromochloroindolyl phosphate (BCIP), nitro blue tetrazolium (NET), naphthol-AS-B1-phosphate, or enhanced chemifluorescent (ECF) substrate. When horseradish peroxidase is used as the label, signals are detected using such substrates as chloronaphthol, aminoethylcarbasole, diaminobenzidine, D-luciferin, lucigenin (bis-N-methylacridinium nitrate), resorufin benzyl ether, luminol, Amplex Red (10-acetyl-3,7-dihydroxyphenoxazine), HYR (p-phenylenediamine-HCl and pyrocatechol), tetramethylbenzidine (TMB), 2,2'-azino-bis(3-ethylbenzthiazoline sulfonate (ABTS), o-phenylenediamine (OPD) or naphthol/pyronine.

Alternatively, the binding of the test material with the cytosolic Hsp60 protein may be analyzed without labeling the interactants for example, a microphysiometer may be used to analyze whether the test material binds to the cytosolic Hsp60 protein. The microphysiometer is an analytical tool measuring the acidification rate of the environment of cells using a light-addressable potentiometric sensor (LAPS). The change in the acidification rate may be utilized as an indicator of the binding between the test material and the cytosolic Hsp60 protein (McConnell et al., Science 257: 1906-1912 (1992)).

The binding ability between the test material and the cytosolic Hsp60 protein may be analyzed by real-time bimolecular interaction analysis (BIA) (Sjolander & Urbaniczky, Anal. Chem. 63:2338-2345 (1991), and Szabo et al., Curr. Opin. Struct. Biol. 5:699-705 (1995)). BIA is the technique of analyzing specific interactions in real time and allows analysis without labeling of the interactants (e.g., BIAcore™). The change in surface plasmon resonance: (SPR) may be utilized as an indicator of the real-time interactions between molecules.

Also, the screening method of the present invention may be performed by two-hybrid analysis or three-hybrid analysis (Zervos et al., Cell 72, 223-232, (1993); Madura et al., J. Biol. Chem. 268, 12046-12054, (1993); Bartel et al., BioTechniques 14, 920-924, (1993); Iwabuchi et al., Oncogene 3, 1693-1696, (1993); and WO 94/10300). In this case, the cytosolic Hsp60 protein may be used as the bait protein. According to this method, the substance that binds to the cytosolic Hsp60 protein, especially protein, may be screened. The two-hybrid system is based on the modular characteristics of the transcription factors consisting of splittable DNA-binding and activating domains. Briefly, this technique employs two DNA constructs. For example, in one construct, a cytosolic Hsp60 encoding polynucleotide is fused with a DNA binding domain-encoding polynucleotide of a known transcription factor (e.g., GAL-4). In the other construct, a DNA sequence encoding the protein to be analyzed ("prey" or "sample") is fused with a polynucleotide encoding the activating domain of the known transcription factor. When the bait and the prey proteins interact and form the complex in vivo, the DNA-binding and activating domains of the transcription factor are brought in proximity and transcription of reporter genes (e.g., LacZ) occur. The detection of the expression of the reporter gene confirms that the analyte protein binds with the cytosolic Ksp60 protein, meaning that it can be utilised as an agent for treating diseases associated with abnormal cell proliferation.

According to the method of the present invention, firstly, the test material to be analyzed is contacted with the cytosolic Hsp60 protein. In the context related to the screening method of the present disclosure, the term "test material" refers to an unknown substance: which is screened to test whether it affects the expression of the cytosolic Hsp60 gene or the activity of the cytosolic Hsp60 protein. The test material may be a chemical, a peptide or a natural extract, but is not limited thereto. The test material analyzed by the screening method of the present invention may be a single compound or a mixture of compounds (e.g., natural extract, or cell or tissue culture). The test material may be: obtained from a library of synthetic or natural compounds. The method for obtaining the library of such compounds is known in the art. A library of synthetic compounds is commercially available from Maybridge Chemical Co. (UK), Comgenex (USA), Brandon Associates (USA), Microsource (USA) and Sigma-Aldrich (USA), and a library of natural compounds is commercially available: from Pan Laboratories (USA) and MycoSearch (USA). The test material may be obtained through, various known combinational library methods. For example, it may be acquired by a biological library method, a spatially-addressable parallel solid phase or solution phase library method, a synthetic library method requiring deconvolution, a "one-bead/one-compound" library method, and a synthetic library method using affinity chromatography selection. The methods for obtaining the molecular libraries are described in DeWitt et al., Proc. Natl. Acad. Sci. U.S.A. 90, 6909, (1993); Erb et al., Proc. Natl. Acad. Sci. U.S.A. 91, 11422, (1994); Zuckermann et al., J. Med. Chem. 37, 2678, (1994); Cho et al., Science 261, 1303, (1993); Carell et al., Angew. Chem. Int. Ed. Engl. 33, 2059, (1994); Carell et al., Angew. Chem. Int. Ed. Engl. 33, 2061; Gallop et al., J. Med. Chem. 37, 1233, (1994), and so forth.

Subsequently, the activity of the cytosolic Hsp60 protein treated with the test material is measured. If down-regulation of the activity of the cytosolic Hsp60 protein is observed as result thereof, the test material may be decided as a therapeutic agent for diseases associated with abnormal cell proliferation.

Further, a substance capable of inhibiting binding between the cytosolic Hsp60 protein and IKK protein can be screened by the present invention. The substance inhibiting the binding between the above described two proteins may be: screened by various methods known in the art, for example, two-hybrid assay (Zervos et al., Cell 72, 223232, (1993)), FRET (Fluorescence resonance energy transfer; Shyu et al., PNAS, 105: 151-156(2008)), PCA (Protein Complementation Assay; Tarassov K., et al., Science, 320(5882): 1465-1470(2008)), PLA (Proximal Ligation Assay; Fredriksson; S., et al., Nat. Eiotechnol., 20(5): 473-477(2002)) or the like.

When the method of the present invention is performed by the two-hybrid assay, the cytosolic Hsp60 and the IKK-α or IKK-β may be constructed as a bait protein and a pray protein, respectively. When the cytosolic Hsp60 protein and the IKK-α or IKK-β protein interact, the DNA-binding and activating domains of the transcription factor are brought in proximity and transcription of reporter genes (e.g., LacZ) occur. Therefore, interaction between the two proteins can be detected by the expression of the reporter gene. According to the present invention, a test material is treated to the cells containing the cytosolic Hsp60 protein (bait protein) and IKK (IκB kinase) protein (prey protein). If the expression of the reporter gene is inhibited compared to before treatment of the test material, it indicates that the described test material inhibits interaction between the cytosolic Hsp60 protein and IKK-α or IKK-β protein.

FRET is an assay that can measure the proximity or distance between a donor and an acceptor, and if different fluorophores are fused to a pair of interacting proteins, an excited donor fluorophore transfers energy to an acceptor molecule. At this time, the efficiency of the energy transfer (FRET efficiency) is defined as the fraction of donor excitation events that results in energy transfer to an acceptor. Hence, FRET efficiency can be used as an indicator of protein-protein interactions.

When the method of the present invention is performed by FRET assay, the cytosolic Hsp60 and the IKK-α or IKK-β are fused with different fluorophores, respectively. A fusion construct of the cytosolic Hsp60 of the present invention and a fluorophore (e.g., GFP, RFP, CFP, YEP, etc) functions as a donor, and a fusion construct of the IKK-α or IKK-β and a fluorophore functions as an acceptor. FRET efficiency can be measured by interaction between the above described two constructs. According to the present invention, the test material is treated to the cells containing the fluorophore (e.g., GFP, RFP, CFP, YEP, etc)-fused cytosolic Hsp60 and KKα or IKK-β constructs. If FRET efficiency is reduced compared to before treatment of the test material, it indicates that the above described test material functions to inhibit interaction between the cytosolic Hsp60 protein and IKK-α or IKK-β protein.

When the method of the present invention is performed by PCA assay, constructs are prepared, by fusion of the cytosolic Hsp60 and the IKK-α or IKK-β with the N-terminal and C-terminal fragments of fluorophores. For example, YEP used as a fluorophore is divided into an N-terminal fragment (N-YEP) and a C-terminal fragment (C-YEP) to prepare constructs fused with cytosolic Hsp60 and IKK-α or IKK-β (N-YEP-cytosolic Hsp60 and C-YEP-IKK-α or C-YEP-IKK-β; alternatively, C-YEP-cytosolic Hsp60 and N-YEP- IKK-α or N-YEP-IKK-β). The cytosolic Hsp60 and IKK-α or IKK-β in these constructs interact with each other, and thus N-terminal and C-terminal fragments of YEP bind with each other to form a complete YEP. Consequently, interaction between two proteins can be detected by fluorescence emission. In the present invention, the test material was treated with cells containing the constructs that are prepared by fusion of the cytosolic Hsp60 and the IKK-α or IKK-β with the N-terminal or C-terminal fragment of fluorophores, and then fluorescence is detected. At this time, if fluorescence is reduced compared to before treatment of the test material, it indicates that the above described test material functions to inhibit interaction between the cytosolic Hsp60 protein and IKK-α or IKK-β protein.

When the screening method of the present invention is performed by analysing the cytosolic Hsp60 expression, changes in the expression level of the cytosolic Hsp60 gene may be measured by various methods known in the art, for example, RT-PCR (Sambrook et al., Molecular Cloning. A Laboratory Manual, 3rd ed. Cold Spring Harbor Press (2001)), Northern blotting (Peter B, Kaufma et al., Molecular and Cellular Methods in Biology and Medicine, 102-108, CRC press), hybridization using cDNA microarray (Sambrook et al. Molecular Cloning. A Laboratory Manual, 3rd ed. Cold Spring Harbor Press (2001)) or rn situ hybridization (Sambrook et al., Molecular Clonrng. A Laboratory Manual, 3rd ed. Cold Spring Harbor Press (2001)).

When performed according to RT-PCR protocol, a cytosol fraction is first separated from, the cells treated with the test material, and total RNA was isolated therefrom, and a first strand cDNA is prepared using oligo dT primers and reverse transcriptase. Subsequently, PCR is performed using the first strand cDNA as a template and a cytosolic Hsp60 gene-specific primer set. Then, a PCR product is electrophoresed, and formed bands are analyzed to determine the changes in the expression level of cytosolic Hsp60 gene.

The changes in the amount of cytosolic Hsp60 protein may be determined by various immunoassays known in the art. For example, the changes in the amount of cytosolic Hsp60 protein may be determined by radioimmunoassay, radioimmunoprecipitation assay, immunoprecipitation, enzyme-linked immunosorbent assay (ELISA), capture-ELISA, inhibition or competition assay, and sandwich assay, but are not limited thereto.

The expression of cytosolic Hsp60, binding to cytosolic Hsp60 protein, or binding between cytosolic Hsp60 and IKK proteins may be analyzed in vivo or in vitro.

According to still another embodiment, the present invention provides a therapeutic agent for diseases associated with abnormal cell proliferation that is the cytosolic Hsp60 inhibitor screened by the above screening method, a therapeutic agent for diseases associated with abnormal cell proliferation that is the inhibitor of cytosolic Hsp60 protein activity binding to the cytosolic Hsp60 protein, screened by the above screening method, or a therapeutic agent for diseases associated with abnormal cell proliferation that is the binding inhibitor of cytosolic Hsp60 protein and IKK protein, screened by the above screening method.

According to still another embodiment, the present invention provides a screening kit for the above screening method. Specifically, it is a screening kit comprising a cell or a cell extract including cytosolic Hsp60 protein, or cytosolic Hsp60 protein and IKK (IκB kinase) protein, and a reaction buffer solution.

Throughout this application, several publications and patents are referenced and citations are provided in parentheses. The disclosure of these publications and patents is incorporated into this application in order to more fully describe this invention and the state of the art to which this invention pertains.

Hereinafter, the present invention will be described in further detail with reference to Examples. It will be obvious to a person having ordinary skill in the art that these examples are illustrative purposes only and are not to be construed to limit the scope of the present invention.

Methods

Reagents

Antibodies to IKKα (B-8), IKKγ (FL-419), Hsp90 (H-114), Hsp60 (K-19 and N-20), IκB (C-21), JNK1 (C-17), ASK-1 (H-300 and F-9), glutathione S-transferase (B14), and goat IgG were purchased from Santa Cruz Biotechnology (Santa Crus, US). Anti-Flag antibody (M2) was purchased from Sigma. Anti-hexahistidine antibody was obtained from Qiagen. Antibodies to phosphor-IKK, phosphor-IKKα, and phosphor-IKKβ were from Cell Signaling Technology. Normal mouse and rabbit IgG were from Amersharm Bioscience. Anti-cytochrome c antibody were from BD Pharmingen. Antibodies to Peroxiredoxin III (Prx III), MnSOD (2AI), Hemagglutinin epitope (HA), and GAPDH were provided, by AbFrontier (Seoul, Korea). Recombinant human TNF-α was purchased from Invitrogen (Grand Island, USA). The phosphorothioate oligodeoxynucleotides (ODNs), including the antisense and sense sequences, were synthesized by Hokkaido System Sciences Co. (Hokkaido, Japan). The full-length human IκB protein was a kind gift of W. Jeong (Ewha Womans University, Korea) [Jung Y, Kim H, Min S H, Rhee S G, Jeong W (2008) Dynein light chain LC8 negatively regulates NF-kappaB through the redox-dependent interaction with IkappaBalpha. J Biol Chem 283: 23863-23871].

Plasmids

The full-length cDNA of human Hsp60 was obtained from the National Genome Information Center (Daejeon, Korea). A truncated form of Hsp60, designated as Hsp60c, which lacks a mitochondrial targeting sequence (MTS; amino acids 1-26 based on human sequence), was amplified by PCR and subcloned into the pCGN-HA. (a kind gift of Dr. W. Herr, Cold. Spring Harbor Laboratory) and pGEX-4T1 (Amersham) vectors, by which the HA-tagged and GST-fused Hsp60c expression plasmids, respectively, were constructed.

CRE-, NF-AT-, and AP1-dependent (pAP17x-Luc) firefly luciferase reporters were obtained from Stratagene. Luciferase reporter plasmids harboring the IFNβ-derived NF-κB enhancer sequences [Fujita T, Nolan G P, Ghosh S, Baltimore D (1992) Independent modes of transcriptional activation by the p50 and p65 subunits of NF-kappa B. Genes Dev 6:775-787] was a kind gift of S. Y. Lee (Ewha Womans University, Korea). Human IKKα, β and γ cDNAs were subcloned into the pCMV2-FLAG or baculovirus expression vector pFastBac-HTa (Invitrogen). The pFastBac contructs, encoding each of IKKα, IKKβ and IKKγ, were used for production of high-titer recombinant baculovirus stocks (~1× $10^7$ pfu/mL), according to the manufacturer's protocol. The pPuro plasmids encoding human Bcl-2 or Bcl-XL were kindly provided by D. Y, Shin (Dankook University, Korea) [Jung M S, Jin D H, Chae H D, Kang S, Kim S C, et al. (2004) Bcl-xL and E1B-19K proteins inhibit p53-induced irreversible growth arrest and senescence by preventing reactive oxygen species-dependent p38 activation. J Biol Chem 279: 17765-17771]. The plasmid pGEX-4 T1-SEK1 (K129R) [Sanchez I, Hughes R T, Mayer B J, Yee K, Woodgett J R, et al. (1994) Role of SAPK/ERK kinase-1 in the stress-activated pathway regulating transcription factor c-Jun. Nature: 372: 794-798] was used for production of GST-SEK1 (K129R) recombinant protein. Site-directed mutagenesis was performed using a QuikChange mutagenesis kit (Stratagene).

Immuno-Affinity Purification of IKK Complex and ESI-q-TOF Tandem Mass Spectrometry HeLa S3 cells (20 mL packing volume from 20L suspension culture) were gently lysed in 200 mL of lysis buffer A (20 mM HEPES (pH 7.5), 150 mM NaCl, 1 mM EDTA, 2 mM EGTA, 1% Triton X-100, 10% glycerol, 1 mM AEBSF, 1 mM $Na_3VO_4$, 5 mM NaF, 10 ug/mL aprotinin and leupeptin). The lysate (2 g of total protein) was precleared with agarose beads alone for 1 hour, and then incubated overnight with anti-IKKα-conjugated agarose beads (2 mg/mL IgG; Santa Cruz Biotechnology). After extensively washing four times with the lysis buffer, the beads were loaded onto a column and rinsed twice with phosphate-buffered saline. The precipitated proteins were eluded twice with 1 mL of 0.1M glycine buffer (pH 2.5). The protein eluates were immediately neutralized by adding 1M Tris HCl buffer (pH 8.0) and separated on a 10% denaturing gel. The gel was subsequently stained with silver nitrate, and the silver-stained spots were subjected to in-gel trypsin digestion with minor modifications as follows. Briefly, the gel spots were excised with a scalped, and destained by washing with 15 mM $K_4Fe$ (CN) s, 50 mM sodium, thiosulfate. The gel pieces were crushed, dehydrated by adding acetonitrile, rehydrated by adding 10-20 mL of 25 mM ammonium bicarbonate with 10 ng/mL of sequencing grade trypsin (Promega), and incubated at 37° C. for 15 hours to 17 hours. The peptides in the supernatant were transferred to a new tube and extracted twice by adding 50 μL of a solution (60% acetonitrile and 0.1% trifluoroacetic acid). The extracted solutions were pooled and evaporated to dryness in a SpeedVac vacuum centrifuge. The tandem mass spectral (MS/MS) analysis for peptide sequencing was done with nano flow reversed-phased HPLC/ESI/MS with a mass spectrometer (Q-TOF Ultima™ global, Waters Co. UK). The peptides were separated by using a $C_{18}$ reversed-phase/5 μm i.d.×150 mm analytical column (3 μm particle size; Atlantis™dC18, Waters) with an integrated electrospray ionization Silica-Tip™ (±10 μm; New Objective, USA). In detail, 5 μL of peptide mixtures were dissolved in buffer A (water/ACN/formic acid=95:5:0.2, v/v), injected, onto a column and eluted by a linear gradient of 5% to 80% buffer B (water/ACN/formic acid=5:95:0.2, v/v) over 120 minutes. Samples were desalted on a line prior to separation using a trap column (i.d. 0.35×50 mm, OPTI-PAK™ C18, Waters) cartridge. Initially, the flow rate was set to 200 mL/min by a split/splitless inlet and the capillary voltage (3.0 keV) was applied to the HPLC mobile phase before spraying. Chromatography was performed online using the manufacturer's control software MassLinx of Q-TOF Ultima™ global. The mass spectrometer was programmed to record scan cycles composed of one MS scan followed by MS/MS scans of the eight most abundant ions in each MS scan. MS parameters for efficient data-dependent acquisition were intensity (>10) and number of components (3-4) to be switched from an MS to MS/MS analysis. Following positive identification, all identified peptides from database search (Mascot) were excluded in the next run analysis until full sequence coverage was obtained. Database analyses using the database search programs including Mascot (global search engine), Proteinlynx 2.1 (Waters Co., UK) and MODi (Korea, http://modi.u-os.ac.kr/modi/), provided almost full sequence coverage on selective exclusion monitoring. MS/MS spectra were matched against amino acid sequences in SwissProt. Precursor ion mass corrections and a fragment ion mass tolerance of 0.2 Da were used to consider as 2 missed cleavages.

Immunoelectron Microscopy

The HeLa cells ($1 \times 10^7$ cells) were harvested and fixed for 1 hour, at room temperature in 0.1M cacodylate buffer (pH 7.2) that contained 0.5% glutaraldehyde. After rinsing with cold, distilled water, the cells were dehydrated through an ethanol treatment series at 4° C. The cells were infiltrated with LR White resin (London Resin, Berkshire, England) at 4° C. and embedded in LR White resin in a gelatin capsules (Nisshin E M, Tokyo, Japan). Polymerization of the resin was carried out at 50° C. for 24 hours. Serial sections (120-200 sections per one sample), 70 nm in thickness, were: attached to formvar-coated nicked, grids. Sections were incubated in 50 mM glycine for 5 minutes at room temperature. After rinsing with PBS, sections were incubated in 3% BSA for 30 minutes at room temperature. Then, they were incubated with primary antibodies (goat anti-human Hsp60 (SC-1722), mouse anti-human IKKα (SC-7606), mouse anti-IKKβ (SC-8014), diluted 1:100 in PBS) for 2 hours, at room, temperature. After washing five times with Tween-PBS (PBS plus 0.5% Tween-20), sections were treated with 20 nm and 40 nm-diameter colloidal gold conjugated to anti-goat and anti-mouse IgG+IgM antibodies, respectively (BB International, UK; diluted 1:20 in PBS) for 2 hours at room temperature. The sections were washed three times with Tween-PBS and then washed three times with distilled water. Sections were stained with 4% uranyl acetate for 5 minutes and with lead citrate for 5 minutes. To examine the specificity of the primary antibody, a treatment of sections was performed with the same procedure without of the primary antibody. For double staining, antibody reactions were repeated with the second set of primary and secondary antibodies. Finally, samples were observed with a Tecnai G2-Spirit Twin transmission electron microscope (FBI Co., USA) and a JEM ARM 130QS high-voltage electron microscope (JEOL, Japan).

Subcellular Fractionation

The subcellular fractions for immunoprecipitation were acquired by differential centrifugation. Briefly, the HeLa cells ($2 \times 10^7$ cells) were harvested, rinsed twice with ice-cold PBS, and resuspended in 1 mL of a homogenization buffer (20 mM HE PES (pH 7.5), 0.5 mM EDTA, 0.5 mM EGTA, 2 mM $MgCl_2$, 25 mM KCl, 1 mM AEBSF, 1 mM $Na_3VO_4$, 5 mM NaF, 5 μg/ml aprotinin, and 5 μg/mL leupeptin) containing 0.25 M sucrose. After rupturing the cells using a glass Bounce homogenizer, the post-nuclear supernatants were obtained from the homogenate by centrifugation (750 g for 10 minutes). The supernatants were separated into pellets (mitochondrial, fraction) and supernatants (cytosol fraction) by centrifugation (15,000 g for 15 minutes). For ODN transfected cells, the subcellular fractions were obtained using the ProteoExtract subcellular proteome extraction kit (Roche). The purity of each fraction was verified by selective markers: α-tubulin as a cytosolic marker; inner membrane protein cytochrome: c oxidase 4 (COX4) and matrix protein peroxiredoxin III (Prx III) [Chang T S, Cho C S, Park S, Yu S, Rang S W, et al. Peroxiredoxin III, a mitochondrion-specific peroxidase, regulates apoptotic signaling by mitochondria. J Biol Chem 279:41975-41984, (2004)] as mitochondrial markers. For best comparison, the mitochondrial fraction was loaded at a volume of one-fifth of the corresponding cytosolic fraction.

In Vitro Binding Assay with Recombinant Proteins

Figure 3:
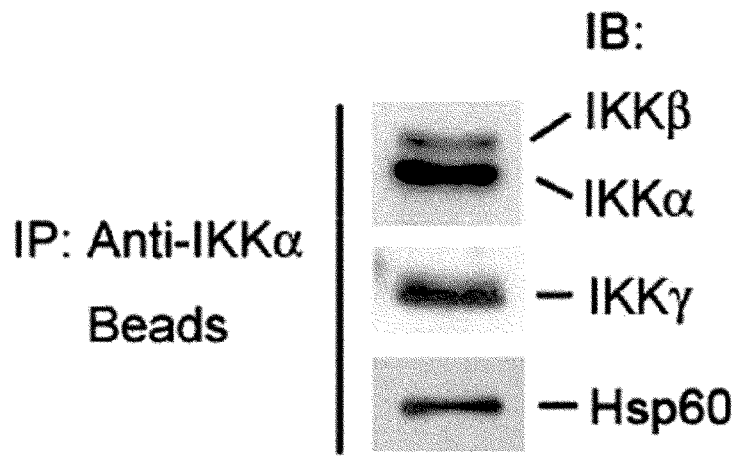

The Sf9 insect cells were infected with each of recombinant baculovirus stocks harboring IKKα-, IKKβ- and IKKγ-encoding bacmids. The insect lysates expressing (His)6- tagged IKKs were incubated with 1.0 μg of GST-Rsp60 proteins pre-bound to glutathione-Sepharose beads (Amersham Pharmacia Biotech) at 4° C. for 2 hours. The beads were washed again three times with a cold lysis buffer A. The proteins bound to the beads were eluted by boiling in a SDS sample buffer and then subjected to immune-blot analyses as indicated in FIG. 3.

The ODNs (200 nM; unless indicated) was transfected for 24 hours using Oligofectamine™ reagent (Invitrogen, USA). The plasmid transfection was achieved using Fugene-6 reagent (Roche, USA). The antibody was transduced using a Chariot™ protein delivery kit (Active Motif Co., USA), according to the manufacturer's instruction.

Immunoprecipitation and In Vitro Kinase Assay

The HeLa cells were treated with or without TNF-α (10 ng/mL) for the indicated time periods, rinsed once with cold PBS, and lysed in the lysis buffer A. The cell lysates were: prewashed with 10 μl of protein A/G agarose beads (Amersham Biosciences) for 1 hour. The washed lysates were incubated with 2 μg of Hsp60, IKKα, IKKβ or IKKγ antibodies for 3 hours and mixed with 20 μL of protein A/G agarose beads. The lysates were further rotated overnight at 4° C. The beads were washed three times with 1 mL of lysis buffer A. The final protein precipitates were subjected to immunoblot analyses. The immune complexes were visualized by using an enhanced chemiluminescence bit (Amersham Biosciences, USA).

For the in vitro kinase assay, the IKK, JNK1 or ASK-1 was immunoprecipitated with anti-IKKγ (FL-419) or anti-JNK1 (C-17) or anti-ASK-1 (H-300) antibody, respectively. The beads containing the IKK complex or JNK1 were washed twice with lysis buffer and further twice with a kinase buffer (20 mM REPES, pH 7.4, 5 mM $MgCl_2$, 10 mM β-glycerophosphate, 1 mM $Na_3VO_4$, 2 mM NaF, and 1 mM dithiothreitol), and then incubated in a kinase buffer containing 10 μM: ATP, 0.6 μCi [$\gamma^{32}P$] ATP, and 2 μg of either GST-IκB(1-54) or GST-c-Jun or GST-SEK1 (K129R) at 30° C. for 30 minutes. The reaction was stopped by adding 20 μL of 3 SDS sample buffer. After boiling, the half of reaction mixture was resolved on a 10% denaturing gel and the radioactivity was detected by autoradiography. The other half of reaction mixture was used for immunoblotting of the immunoprecipitated kinase proteins (note: anti-ASK-1 antibody (F-9) for detecting ASK-1).

Measurement of Intracellular ROS

Intracellular ROS generation was assessed with an oxidation sensitive fluoresce dye, 5,6-chloromethyl-2',7'-dichlorodihydrofluorescein diacetate (CM-$H_2$DCFDA, Molecular Probes, USA) as described [Rang S W, Chae H Z, Seo M S, Kim K, Baines I C, et al. Mammalian peroxiredoxin isoforms can reduce hydrogen peroxide generated in response to growth factors and tumor necrosis factor-alpha. J Biol Chem 273: 6297-6302, (1998)]. The HeLa cells ($3 \times 10^5$) were plated on 35-mm dishes and transfected with ODNs for 24 hours. The cells were then deprived of serum for 6 hours and stimulated with TNF-α in phenol red-free media for the indicated periods of time. After stimulation, the cells were quickly rinsed with Krebs-Ringer solution and incubated for 5 minutes with 5 μM CM-$H_2$DCFDA. The DCF fluorescence was collected for 10 seconds with an inverted Axiovert200 fluorescence microscope (Zeiss). The relative DCF fluorescence was obtained by averaging the fluorescence intensities of the 60-80 cells in each image using ImageQuant™ software (GE Healthcare). Note that the detached round cells were omitted from quantification.

RNase Protection Assay

ODN-pretreated HeLa cells were treated with or without TNFα (10 ng/mL) for the indicated times. The total RNA was extracted with Trizol reagent(Invitrogen). The ribonuclease (RNase) protection assay was performed according to the manufacturer's protocol (BD PharMingen). Briefly, the human apoptosis template set hAPO-5 was labeled with [$\alpha$-$^{32}P$]-uridine triphosphate. The RNA (10 μg) and $6 \times 10^5$ cpm of the labeled probes were subjected to hybridization. After the RNase treatments, the protected probes were resolved on 5% urea-polyacrylamide gel and detected by autoradiography.

Quantitative PCR (qPCR)

Total RNA was extracted using Trizol reagent (Invitrogen) from the HeLa cells stimulated with TNF-α for indicated periods of time. RNA (1.5 μg) was reverse transcribed using ImProm-II RT system (Promega). The real-time PCR was performed using specific primers in the presence of SYBR Green (Applied Biosystems) inside a fluorescent temperature cycler (ABI Prism 7000 sequence detection system, Applied Biosystems). The fluorescence signals were quantified by a comparative cycle threshold method. The actin mRNA was used for an endogenous control.

Transgenic Mice Generation

The HA-tagged human Hsp60c lacking mitochondrial signal sequence was PCR-amplified and subcloned into pCAGGS transgenic (Tg) vector, which contains the chicken β-actin promoter, using NheI and EcoRV sites. The HA-Hsp60c Tg construct was linearized by digestion with SaiI and PstI and then microinjected into eggs from C57BL/6J females. The transgenic founders were genotyped as described below. Two of the six positive transgenic lines, designated T4 and T11, were chosen for this study. The tail DNA was used for genotyping. In brief, mouse tail DNAs were incubated overnight in 100 mM Tris (pH 8.0), 0.5 mM EDTA, 200 mM NaCl, 0.2% SDS, and 100 μg of proteinase K at 55° C. DNA was extracted with phenol:chloroform:isoamyl alcohol (25:24:1) and precipitated with isopropanol. Genomic PGR was performed by using the following primer sets: set 1,5'-ATGGCTTCTAGCTATCCTTATG-3' (forward, SEQ ID NO. 8) and 5'-GTAGCAACCTGTGCAATTTCTIC-3' (reverse, SEQ ID NO. 9); set 2, 5'-CTGCTAACCATGT-TCATGCC-3' (forward, SEQ ID NO. 10) and 5'-ACAAGTT-TAGCTCCAATGTTTTTGTA-3' (reverse, SEQ ID NO. 11). All the experiments were performed with 4-week-old males.

Analysis of Apoptotic Cells in DEN-Induced Liver Damage

The four-week-old male mice were injected intravenously with phosphate-buffered saline (PBS, pH 7.4) or TNF-α (6 μg/kg body weight) via the lateral tail vein 6 hours before: intraperitoneal administration of DEN (10 mg/kg body weight). After 48 hours of DEN treatment, animals were sacrificed and rapidly perfused with PBS followed by 4% paraformaldehyde. The livers were removed and frozen in OCT embedding medium, and then a series of tissue sections (10 μm in thickness) was obtained in cryostat (Leica). The sections were incubated in 50 μl of terminal deoxynucleotidyl transferase-mediate uridine 5'-triphosphate-biotin nick-end labeling (TUNEL) fluorescent reaction mixture (In situ Cell Death Detection Kit, Roche Diagnostics) for 60 minutes at 37° C. in a dark chamber, washed and subsequently counterstained with 4',6'-diamidino-2-phenylindole (DAPI, 1 μg/mL, Sigma) for 30 minutes. The sections were mounted using the Vectashield mounting medium and examined using a LSM510 confocal laserscanning microscope (Carl Zeiss, Germany). TUNEL-positive cells were counted and averaged from at least three tissue sections per mouse. All animal experiments were performed in compliance with the Institutional Guidelines for the Care and Use: of Laboratory Animals (Ewha Womans University, Korea).

Balloon-Injury in Rat Carotid Artery

In this experiment, male Sprague-Dawley rats weighing 270-290 g (Charles River, USA) were used. Rats were fed with water and food ad libitum, and housed in an automatic system similar to natural light-dark cycle. Anesthesia was induced with 5% isoflurane in a mixture of 70% nitrous oxide and oxygen, and then 1% to 2% isofluran was maintained during experiment. As described previously, balloon injury was carried out in the left carotid artery of normal rat by a Fogarty 2F balloon catheter (Usui et al. 2002). After anesthesia of 10-week-old rats, the left external carotid artery was exposed, and then its branches were electrocoagulated. The catheter was inserted via an external carotid arteriotomy incision about 1 cm in length, and endothelial denudation of the common carotid, artery was carried out by three passages. At 0 h, 18 h, 3 days, 5 days and 7 days after injury, carotid artery was transcardially perfused with heparinized saline containing 3.7% formaldehyde, incised and paraffin-embedded. Five serial sections (100-μm width and 3-μm thickness) were obtained from the middle portion of the common carotid artery. For all subsequent studies, sections from the middle portion of the vessel were analyzed. Each slide was stained with hematoxylin and eosin (H&E) for the morphometric study.

In Vitro Osteoclasfcogenesis Assay

The non-adherent bone marrow-derived monocytes/macrophages (BMM) lineage cells derived from C57BL/6J mice were seeded and cultured in α-MEM (Invitrogen) containing 10% FBS and M-CSF (10 ng/mL, R&D systems). After 2 days, the nonadherent cells including lymphocytes were used as BMMs. The differentiation of BMM to osteoclast cells was induced by treating them with either soluble RANKL (50 ng/mL, Peprotech) or TNF-α (20 ng/mL) in the presence of M-CSF. For retrovirus infection, BMMs were reacted with a control group or supernatant including Hsp60c-expressing retrovirus in the presence of polybrene (10 μg/rciL). After 2 day-exposure to virus, the cells were reacted with RANKL as described above. After 5 days of induction, the cells were fixed and stained for tartrate-resistant acid phosphatase (TRAP; Sigma Co.). The cells were observed using a Zeiss Axiovert 200 microscope (Carl Zeiss) equipped with a plan-Neofluor objective lens. The images were analyzed using AxioVisron 3.1 software (Carl Zeiss). The TRAP-positive multinucleated (>3 nuclei) cells were counted as osteoclast-like cells.

Statistics

Figure 2:
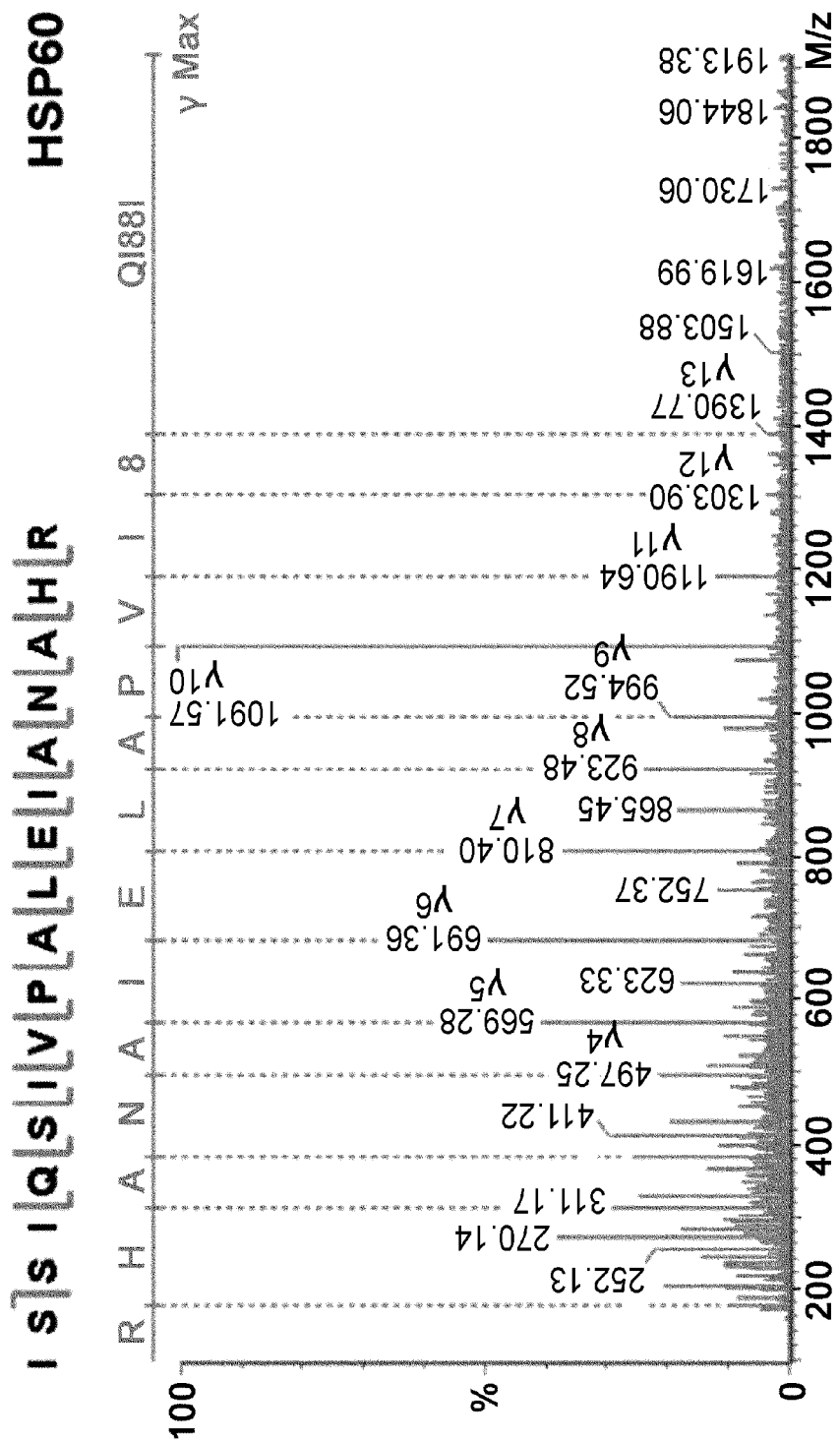

Data were analyzed using Student's t-test on SigmaPlot 8.0 software. The P values were derived to assess statistical significance and indicated on figure panels Results Hsp60 Interacts with IKK Complex in Cytoplasm The present inventors examined the molecular composition of the latent IKK complex using a proteomic technique combining immune-affinity purification and mass spectrometry. Briefly, the IKK complex was precipitated from the lysates of unstimulated HeLa S3 cells using anti-IKKαantibody beads, and the co-precipitated proteins were sequenced by liquid chromatography-tandem mass spectrometry. The identification of the IKK subunrts and Hsp90 indicated that the immunopurification of IKK complex fairly worked (FIG. 1), and a heat shock protein Hsp60 was identified in the precipitates (FIGS. 1-2). The presence of the IKK subunits and Hsp60 in the precipitates was confirmed by immunoblotting (FIG. 3). Then, the present inventors decided to investigate the biological meaning of the IKK-Hsp60 interaction.

Figure 4:
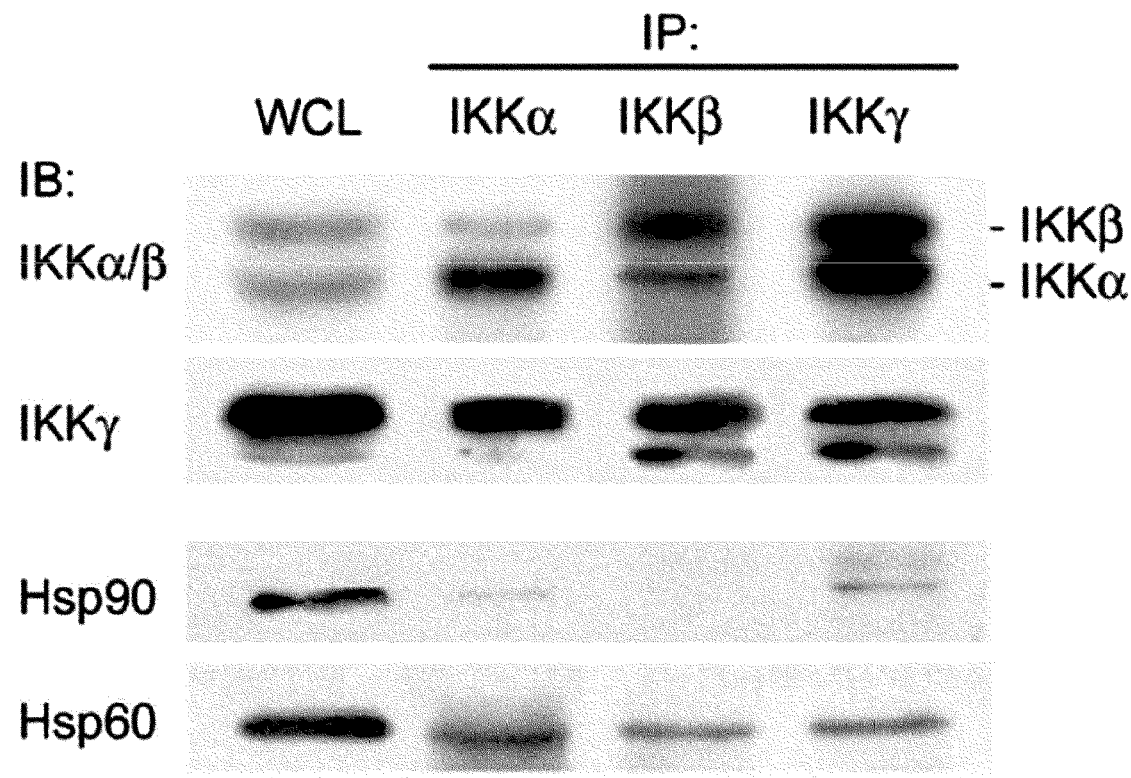
Figure 5:
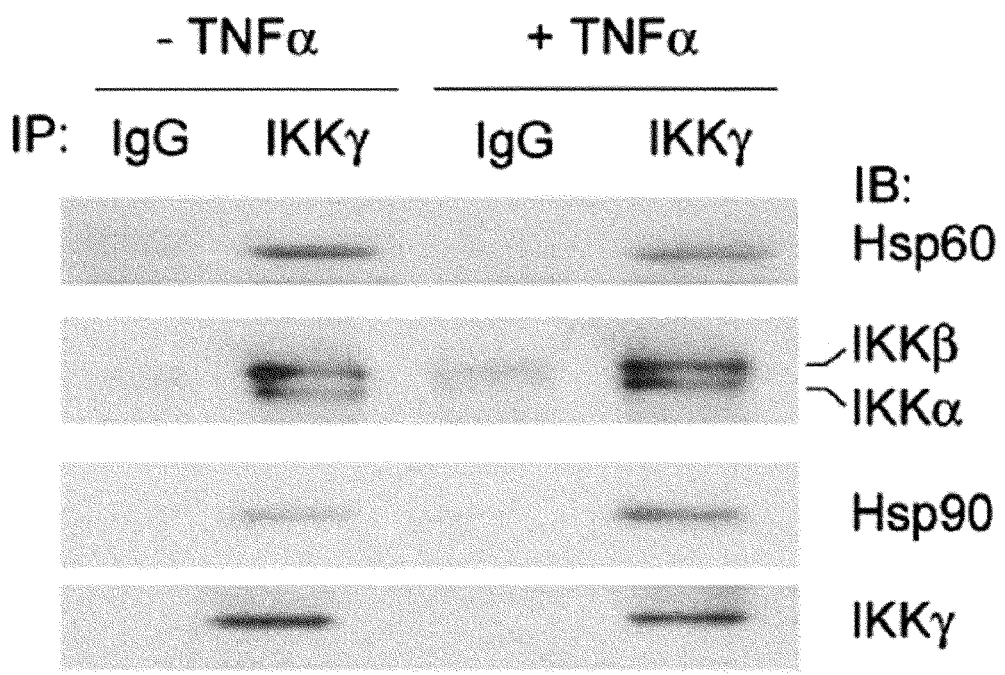
Figure 6:
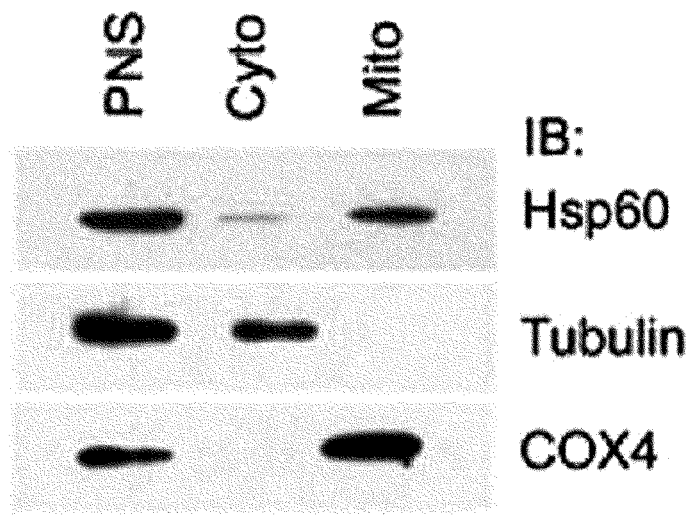
Figure 6:
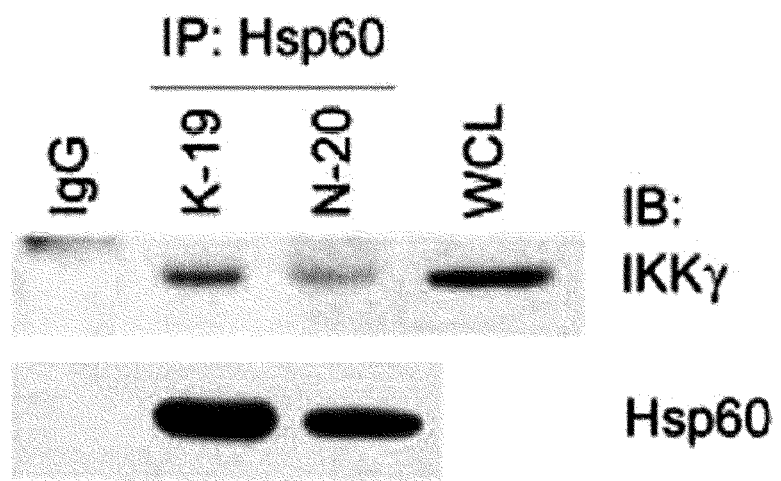
Figure 7:
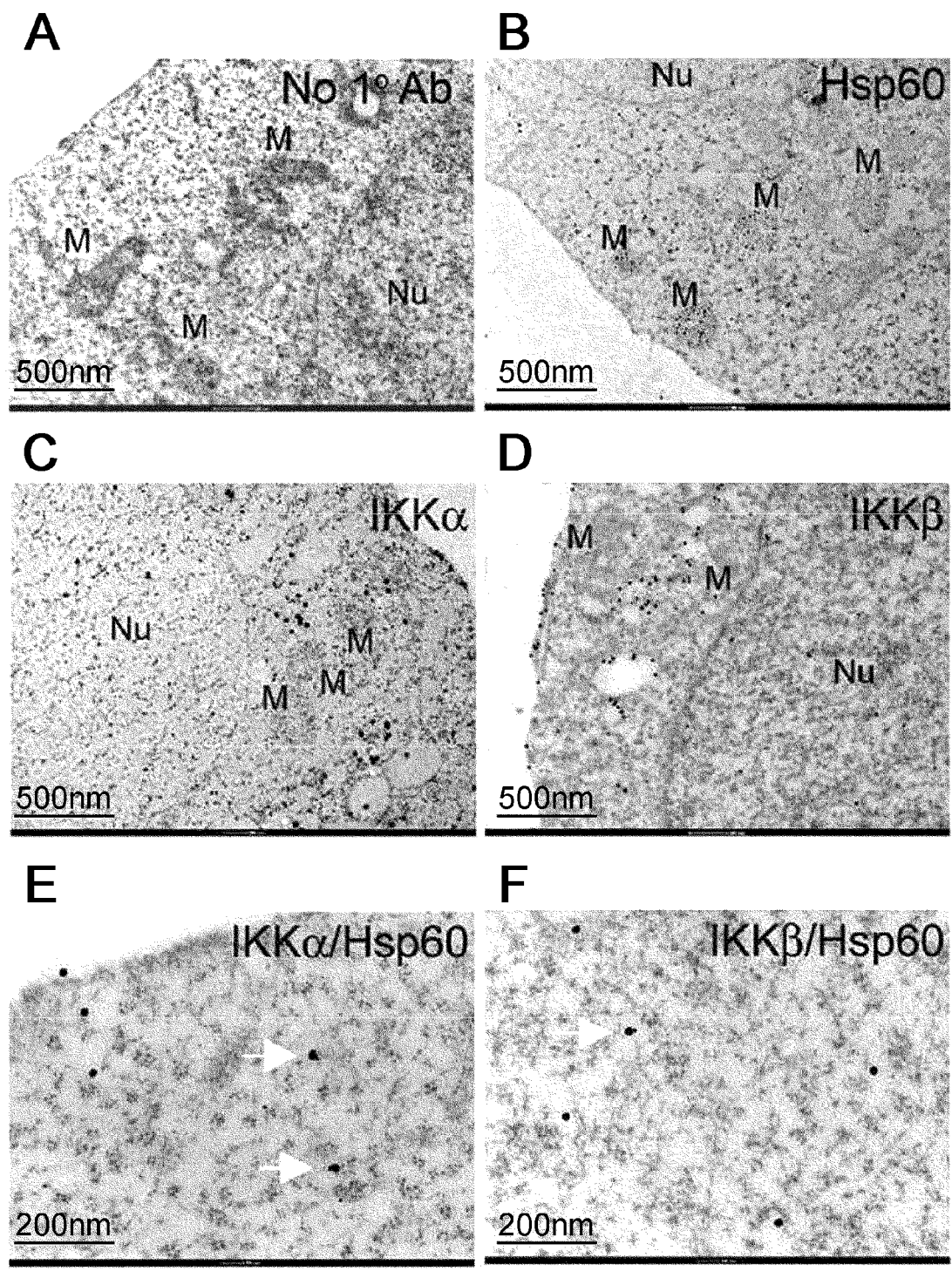
FIG. 7 is the results of visualization of Hsp60 and IKK interaction at a single-cell level. HeLa cells were immune-reacted with no primary (A), anti-Hsp60 (B), anti-IKKα (C), anti-IKKβ (D), anti-Hsp60/IKKα (E), and anti-Hsp60/IKKβ (F) antibodies, and then labeled with the corresponding secondary antibodies conjugated with 20 nm or 40 nm gold particles. The labeling was assessed by immuno-gold electron microscopy. Nuclei (Nu) and mitochondria (M) are indicated. Arrows indicate direct adherence of Ksp60- and IKK-labeled gold particles. No immunoreactive signal was seen in the sample without primary antibodies (A). The experiments were repeated twice with the same results, and representative results are shown.

The endogenous interaction of Hsp60 and IKKs was first verified by co-immunoprecipitation experiments. When the heterogeneous IKK complexes were precipitated with antibodies against IKKα, IKKβ and IKKγ, each of the IKK subunit-specific antibodies similarly precipitated Hsp60 (FIG. 4). In addition, Hsp90 was also co-precipitated with IKK complex. This interaction was found to be unaffected by TNF-α treatment (FIG. 5), indicating that Hsp60 is a component protein of heterogeneous IKK complexes. A reverse immunoprecipitation was then carried out with the cytosolic fraction to exclude the mitochondrial contamination. The anti-Hsp60 antibodies coprecipitated IKKγ with Hsp60, whereas control goat IgG did not (FIG. 6), confirming that cytosolic interaction of Hsp60 and IKK. In order to visualize the virtual interaction of Hsp60 with IKKs in cytoplasm, the immune-gold staining combined with the electron microscopy (EM) was performed. The immune complexes of Hsp60 and IKK with their specific antibodies were detected differently using secondary antibodies labeled with 20 nm- and 40 nm-diameter gold particles, respectively. As a result, the Hsp60-labeling gold particles were distributed throughout the cellular structures: not only in the matrix and intermembrane space of mitochondria, but also in the cytoplasm and plasma membrane (FIG. 7B). In contrast, the IKKα- and IKKβ-labeling gold particles were mainly detected in the cytoplasm (FIGS. 7C and 7D), while the IKKα-labeled gold particles were also detected in the nucleus, which is consistent with the previous reports [Anest V et al., Nature 423:659-663 (2003)]. Considering that IKKα is known to regulate NF-κB transcriptional activation in the nucleus, the Hsp60-IKKαcomplex translocates to nucleus, and is involved in the promoter of particular gene set (e.g., MnSOD and Bfl-1/A1). The data of the present invention showed that the IKK-labeling gold particles were often seen in the vesicular structures rather than the mitochondria (FIGS. 7C and 7D). When the Hsp60 and IKKs were co-stained, the direct binding of 20 nm and 40 nm gold particles was clearly detected in the cytoplasm (FIGS. 7E and 7F). It should be noted that not all of the IKKα and IKKβ were associated with Hsp60. These results collectively indicate that the Hsp60 directly interacts with IKK complex in the cytosol.

Hsp60 Directly Interact with IKKα/β, not IKKγ

Figure 8:
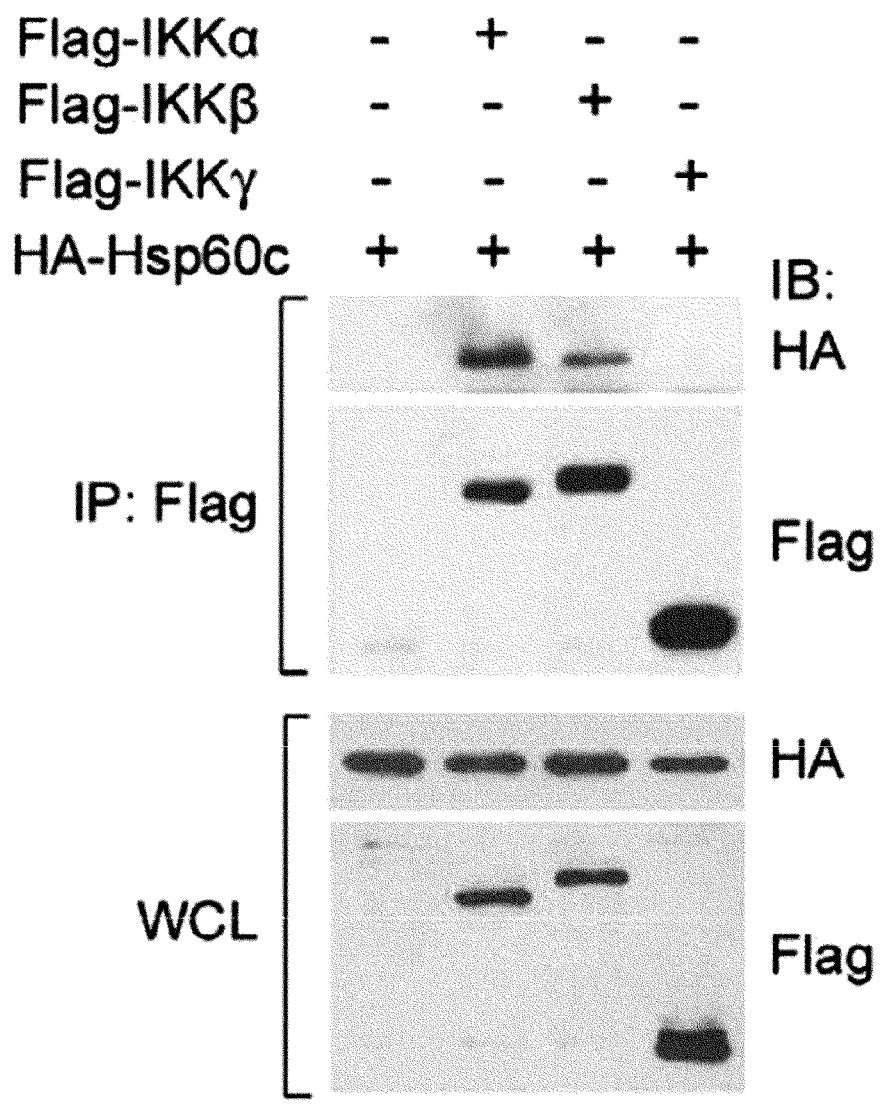
FIGS. 8 to 12 show that Hsp60 directly interacts with IKK complex.
Figure 9:
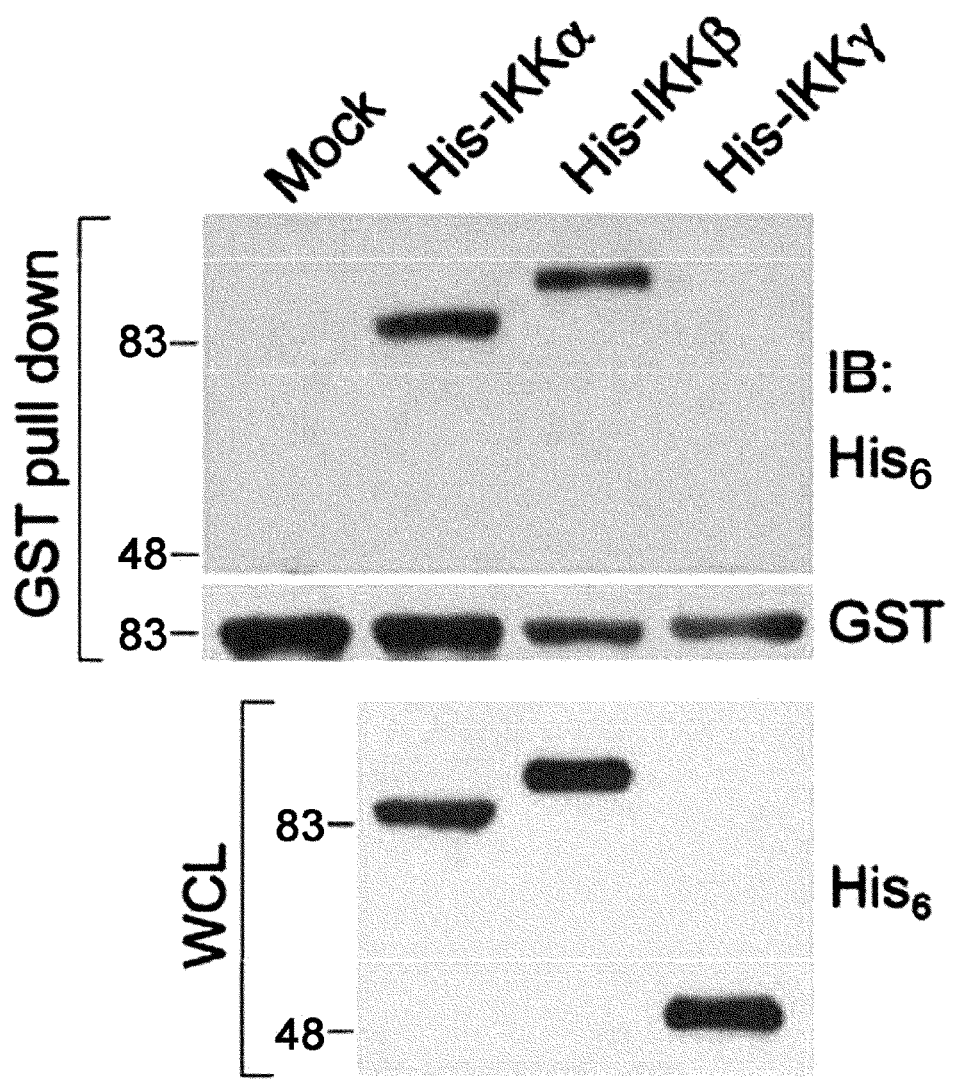

The present inventors analyzed the molecular interaction of Hsp60 and IKKs. To do this, a cytosol-targeted version of Hsp60 (Hsp60c), wherein the mitochondrial targeting signal sequence is deleted, was constructed. When Hsp60c was co-expressed with each of the IKK core subunits, Hsp60c interacted with IKKα and, albeit to a lesser extent, with IKKβ, but not with IKKγ (FIG. 8). Then, an in vitro binding experiment using the recombinant proteins of glutathione-S-transferase (GST)-fused Hsp60 and (His)-tagged IKK core subunits was assessed by a GST pull-down assay. The result, again, indicates that Hsp60 binds directly to IKKα and IKKβ, but not to IKKγ (FIG. 9).

Figure 10:
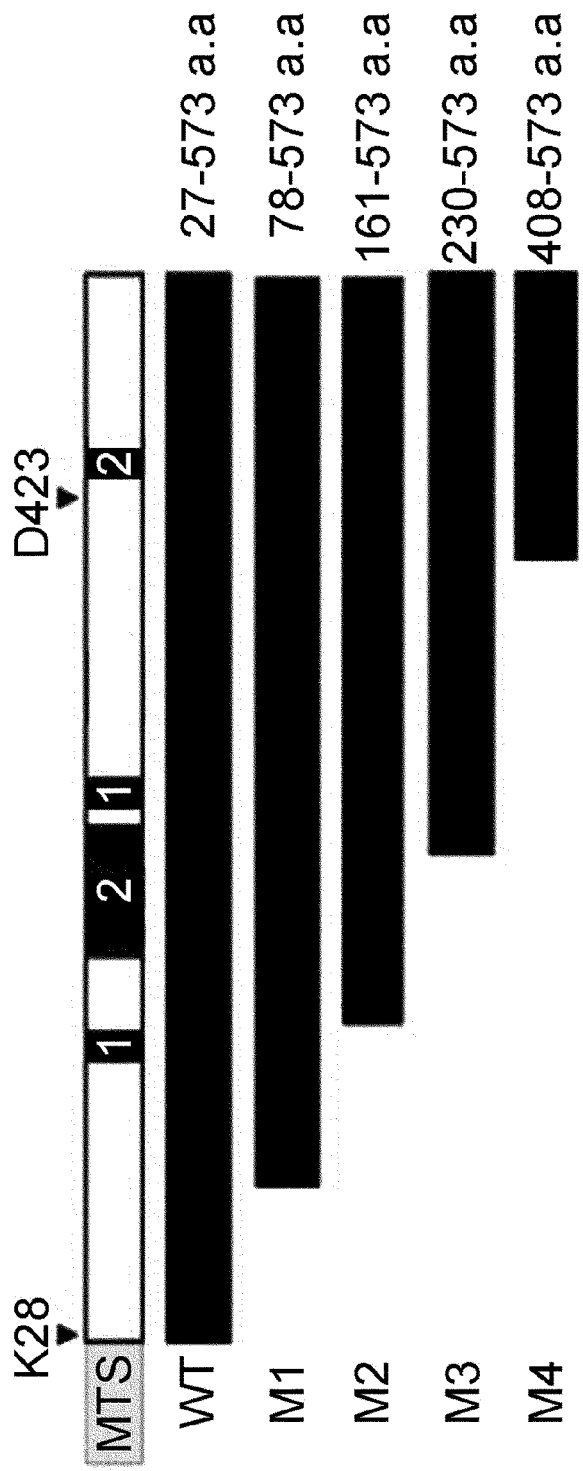
Figure 11:
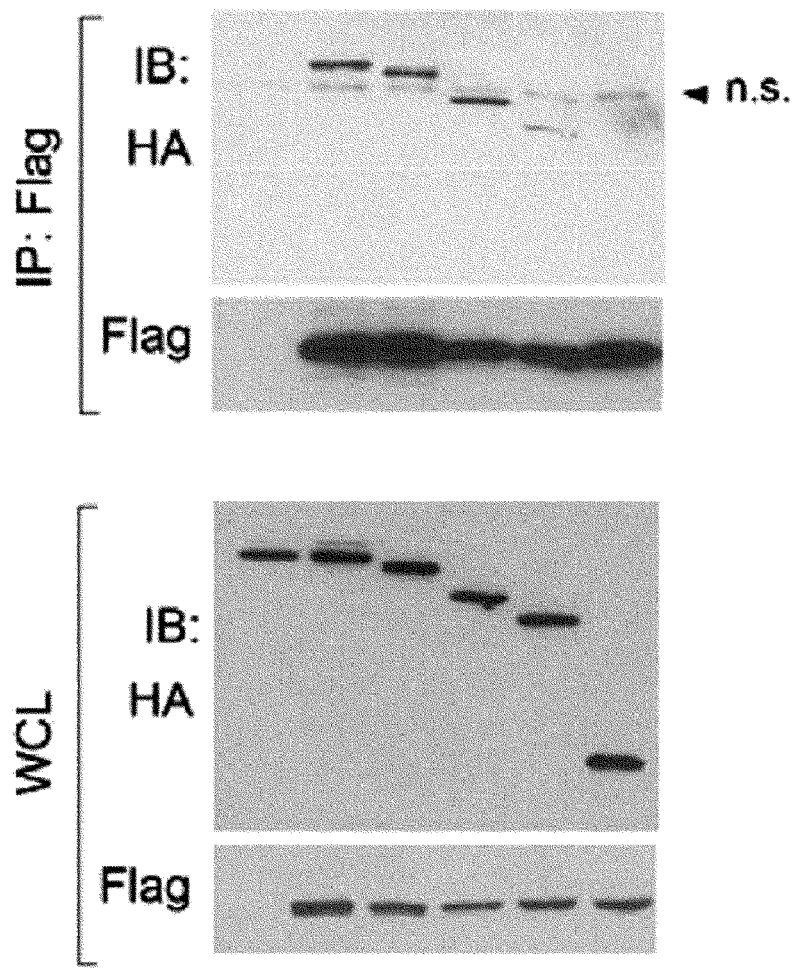
Figure 12:
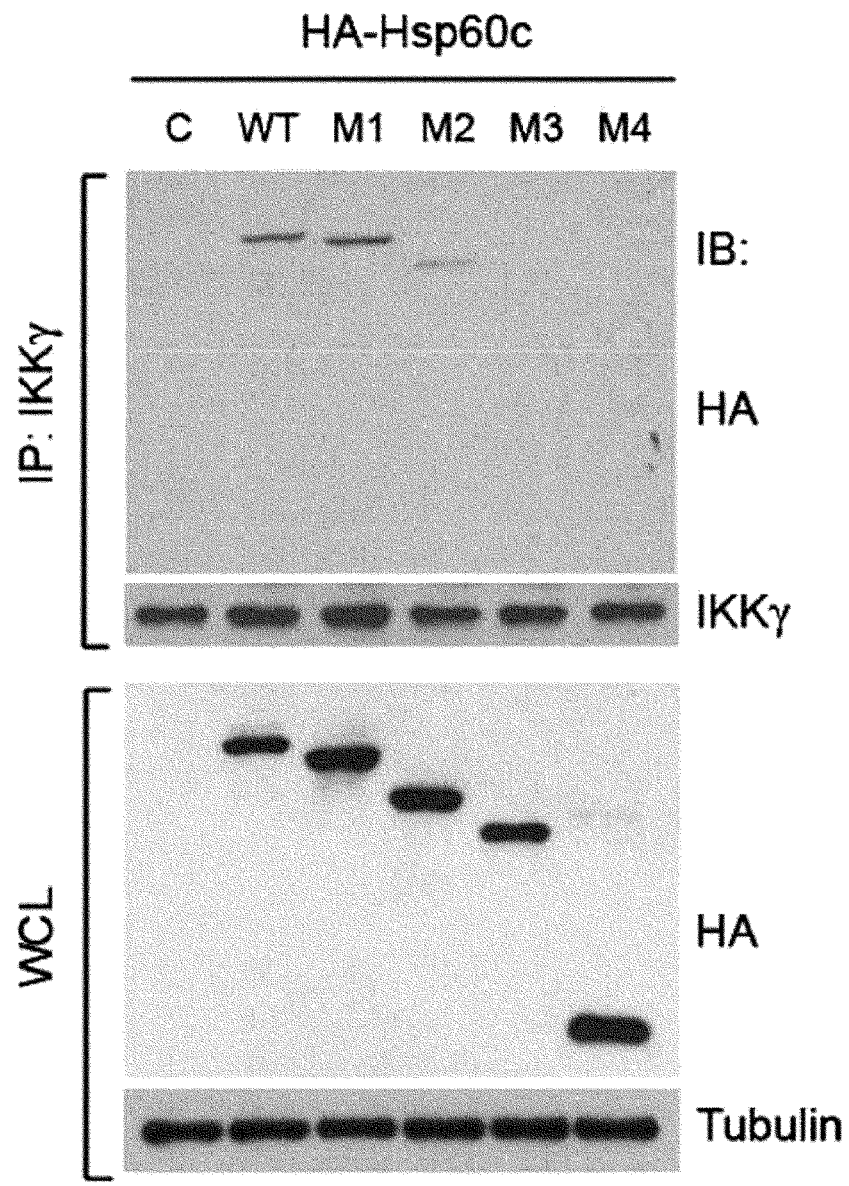

The molecular interaction of Hsp60 with IKKs was further characterized by domain mapping experiments. Because the C-terminal deletion hampered the ectopic expression, a series of N-terminal deletion mutants of Hsp60c was tested for IKK binding via co-expression with Flag-tagged IKKα in HEK293 ceils (FIG. 10). The results showed that the N-terminal part (approximately 160 amino acids from N-terminus) of Hsp60 protein was shown to be dispensable for the interaction with IKK (FIG. 11). The same result, was obtained when endogenous IKK complex was immunoprecipitated from HeLa cells transfected with the Hsp60c constructs (FIG. 12). The results fairly indicate that the core binding domain is located in the middle of Hsp60 protein.

Hsp60 is Involved in the IKK/NF-κB Activation

Figure 13:
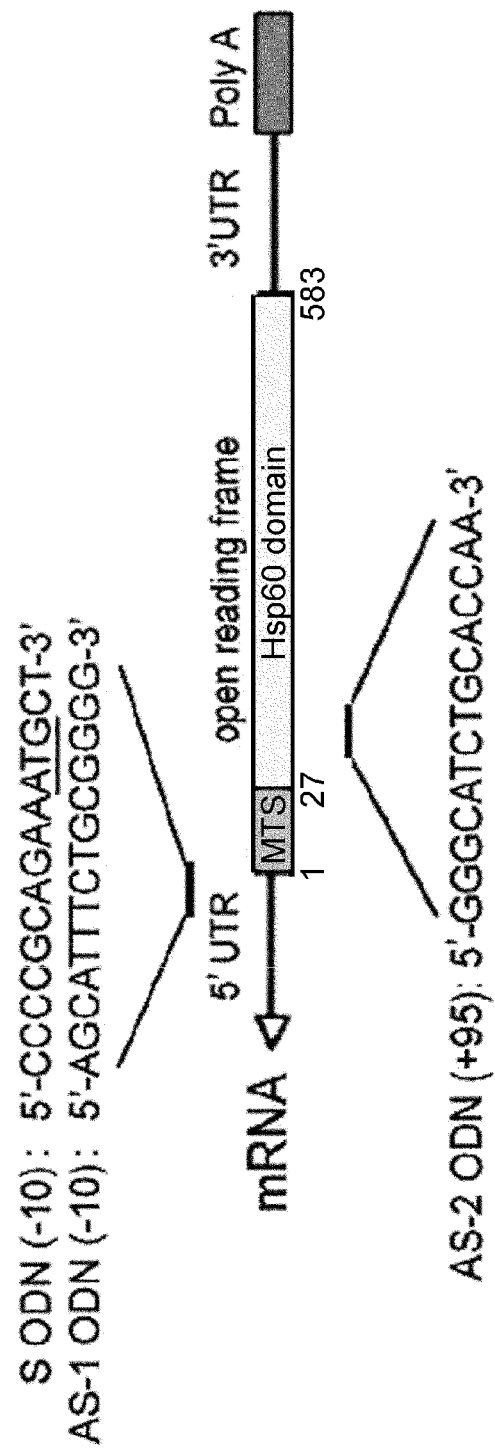
FIGS. 13 to 17 snow action of Hsp60-specific antisense oligodeoxynucleotide (AS-ODN), FIG. 13 snows schematic representation of two different Hsp60 AS-ODNs, FIG. 14 snows Hsp60 expression in mock- or ODN-transfected HeLa cells.
Figure 14:
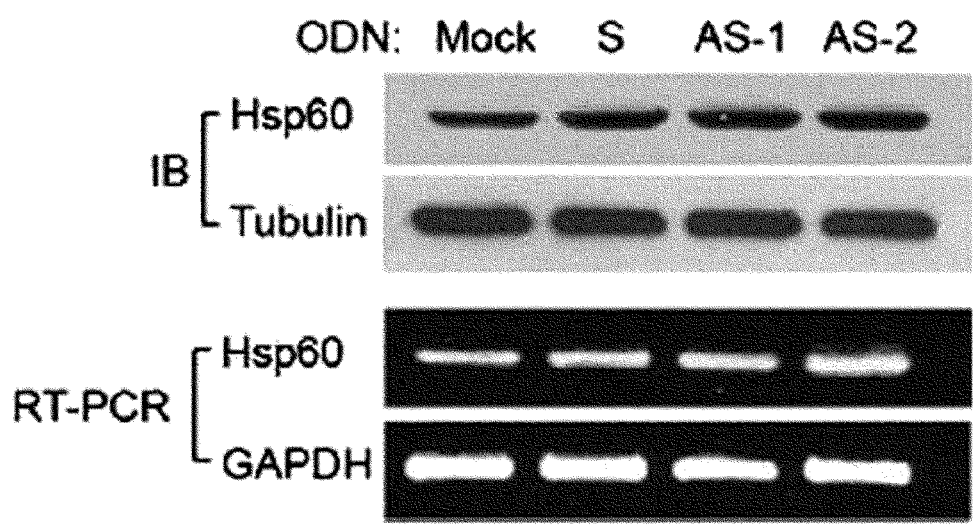
Figure 19:
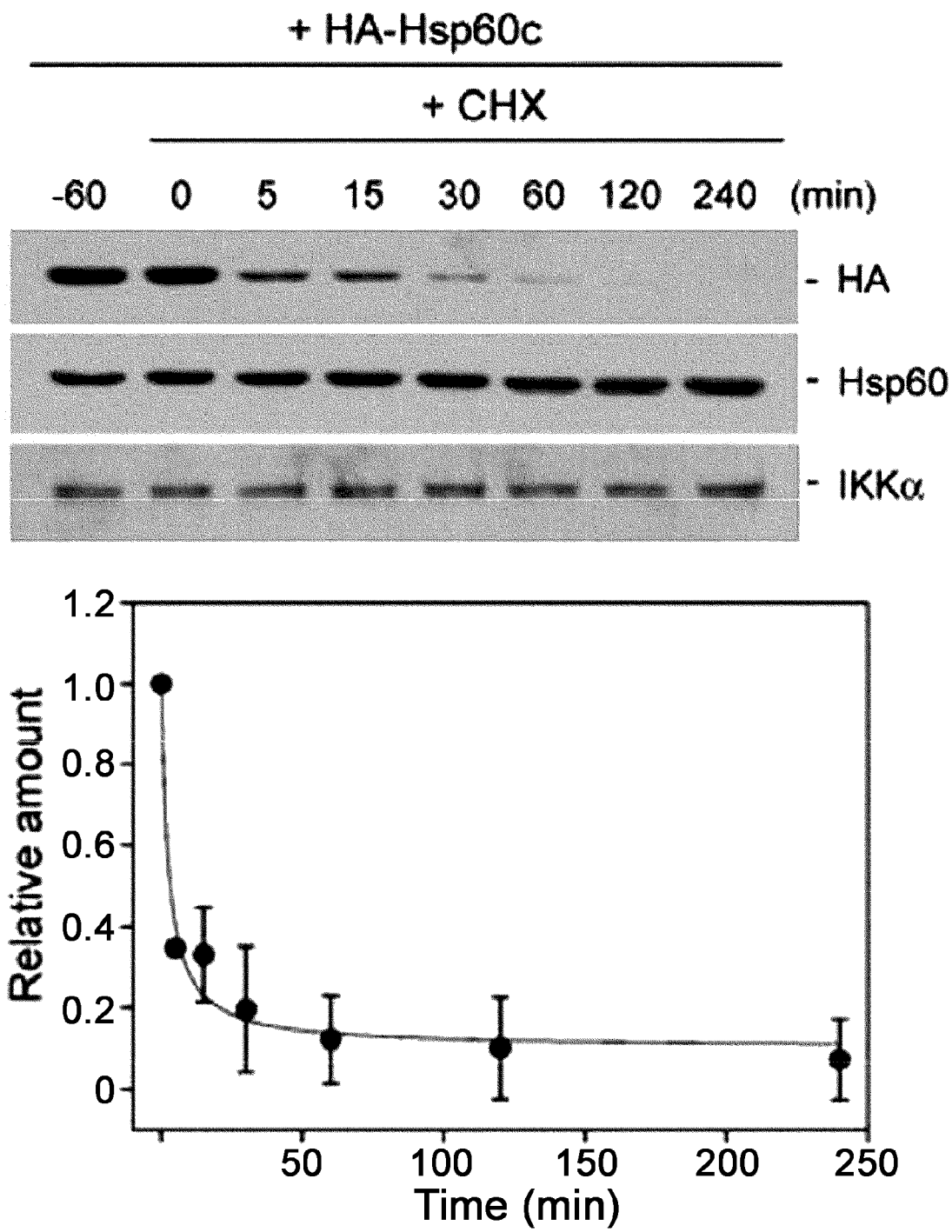
Figure 20:
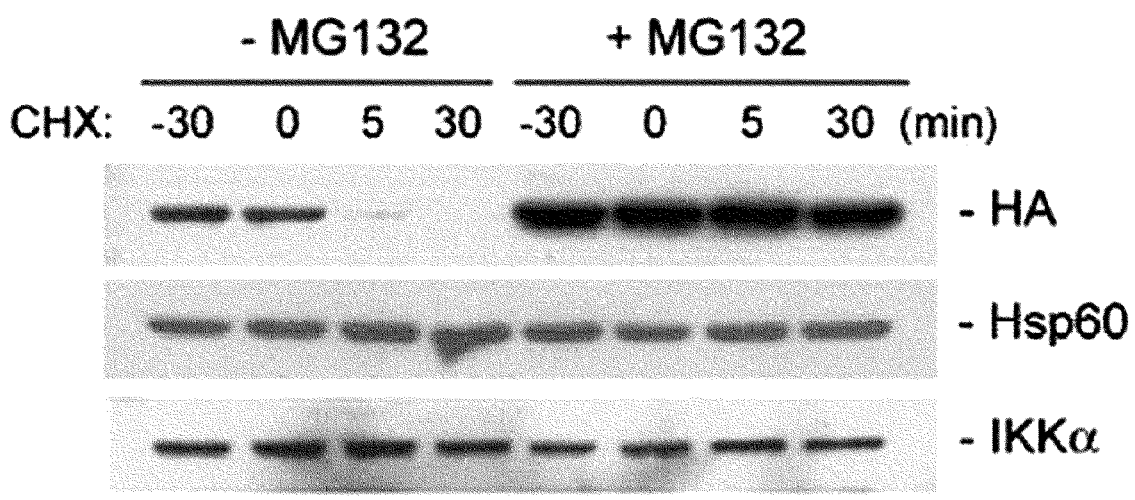

The biological effect of cytosolic Hsp60-IKK interaction was investigated in TNF-α-mediated NF-κB pathway. To achieve the goal, the essential step is to manipulate the level of cytosolic Hsp60 without affecting the mitochondrial one because Hsp60 deficiency is known to cause a mitochondrial functional defect [Bozner P et al., j Alzheimers Bis 4:479-486 (2002); Briones P et al., J Inherit Metab Dis 20:569-577 (1997); Huckriede A et al., Virchows Arch 427:159-165 (1995)]. Interestingly, a number of studies have previously reported that an antisense oligodeoxynucleotide (AS-ODN) complementary to a sequence surrounding the start codon of the human Hsp60 open reading frame (ORF) actually reduces the cytosolic Hsp60 level [Park S G et al., J Biol Chem 278:39851-39857 (2003); Kirchoff S R et al., Circulation 105:2899-2904 (2002); Steinhoff U et al., Proc Natl Acad Sci USA 91:5035-5088 (1994)]. The present inventors, therefore, decided to test this AS-ODN (designated as AS-1; SEQ ID NO. 3) for a selective knockdown effect. In order to exclude the possibility of non-specific action of a particular ODN sequence, the present inventors chose a second AS-ODN (AS-2, SEQ id NO. 4) that is complementary to the region (+95 to +110 from start codon) near the 5'-end, but after mitochondrial targeting signal sequence (MTS) of Hsp60 ORF (FIG. 13). In order to examine whether the objects of the present invention can be achieved by antisense oligonucleotides targeting all regions in ORF, AS-3 ODN (SEQ ID NO. 5), AS-4 ODN (SEQ ID NO. 6) and AS-5 ODN (SEQ ID NO. 7) specific to the downstream sequences of the AS-2 ODN target sequence were constructed. The sense ODN (S-ODN) complementary to AS-1 was used as a control ODN. Since the antisense ODN is a moderate translational blocker, it did not elicit the reduction of total Hsp60 level (FIG. 14). However, the transfection of AS-ODNs indeed selectively reduced cytosolic Hsp60 levels compared to the mock or control S-ODN without affecting the mitochondrial level (FIG. 13). To understand this phenomenon, the present inventors hypothesized that the half-life of Hsp60 protein in two compartments may differ. To prove it, the half-life of cytosol-targeted Hsp60 (Hsp60c) was assessed after inhibition of protein synthesis. Surprisingly, the level of cytosolic Hsp60 protein was rapidly reduced (calculated t½=3.2 min), while total level of endogenous Hsp60 and IKKα proteins was unchanged (FIG. 19). Moreover, this reduction was completely blocked by the treatment of a proteasome inhibitor MG132 (FIG. 20). It is noted that the MG132 treatment also resulted in the remarkable increase of the basal level of the Hsp60c protein. Thus, this result, at least in part, explains why the level of cytosolic Hsp60 was more sensitive to AS-ODN treatment., and it additionally suggests that the level of cytosolic Hsp60 might be controlled by proteasome.

Figure 15:
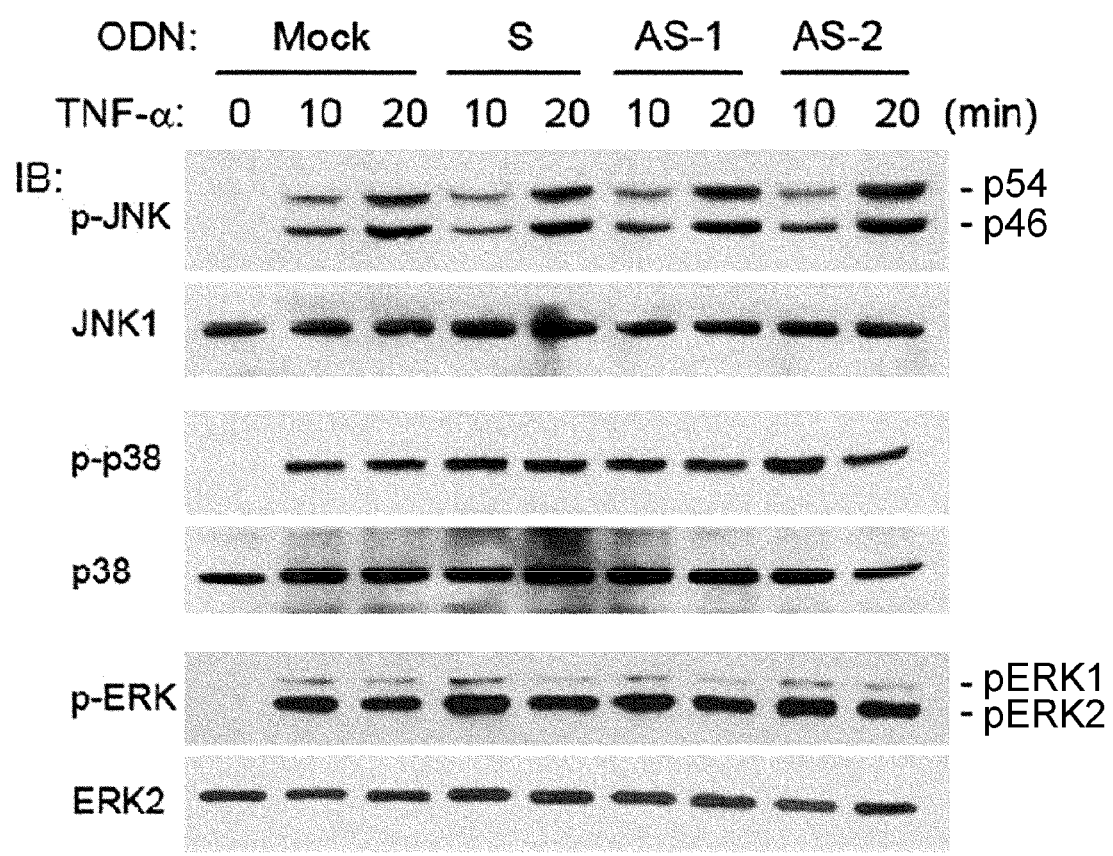
Figure 16:
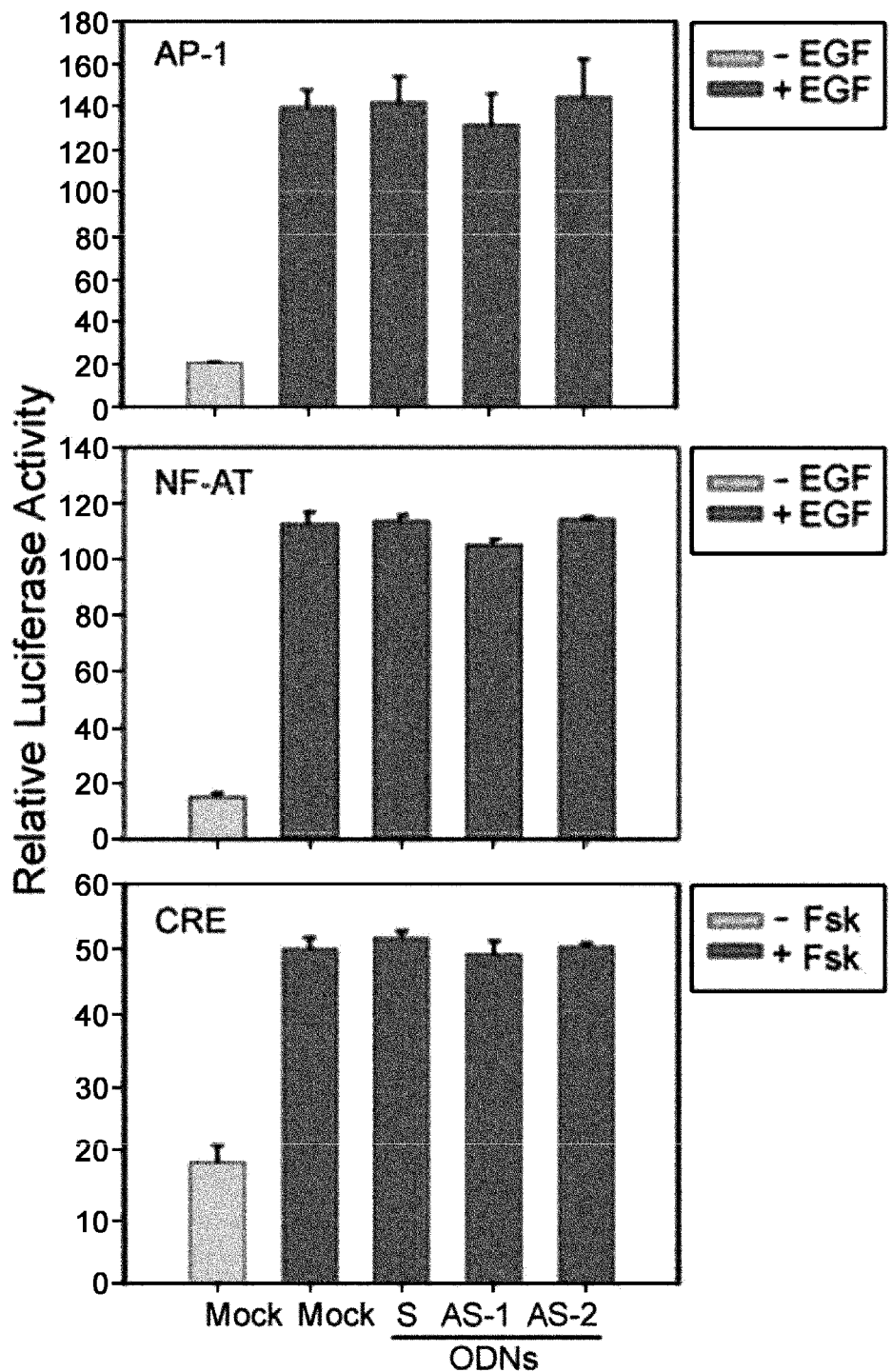
Figure 17:
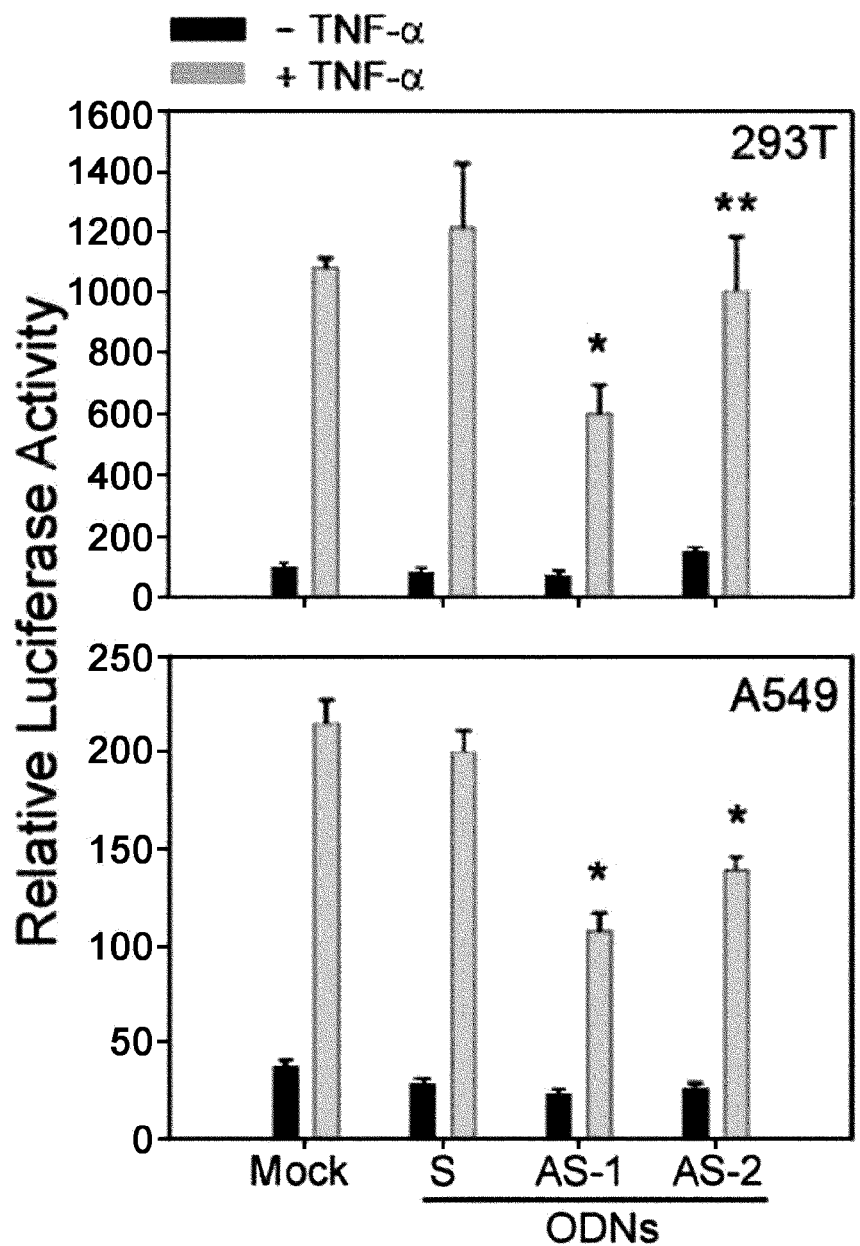
Figure 18:
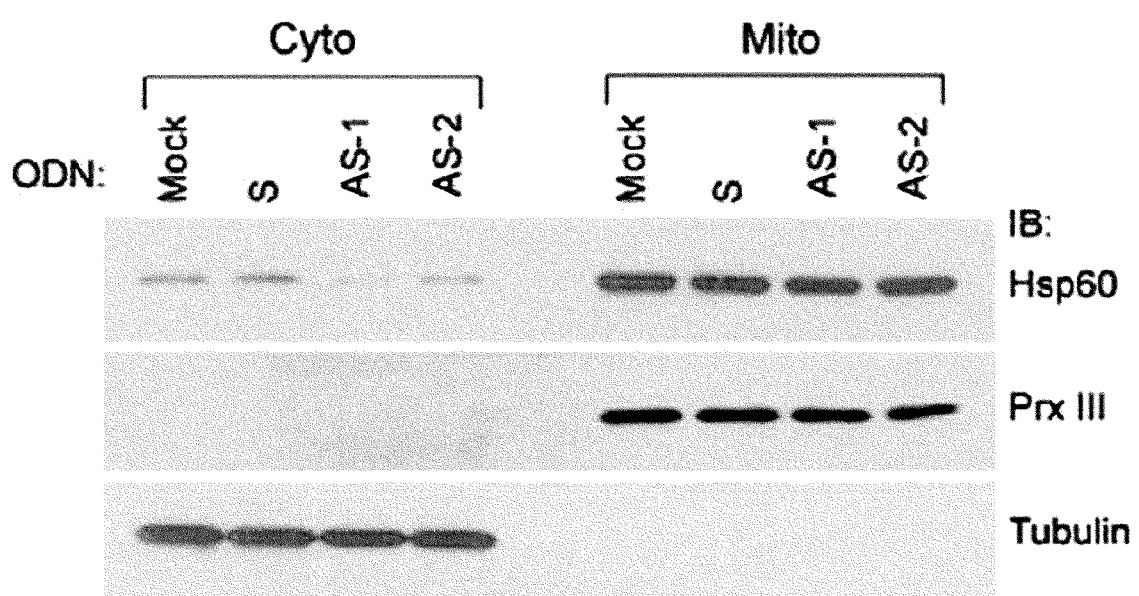
FIGS. 18 to 23 snow that loss of cytosolic Hsp60 diminishes IKK/NF-κB activation in response to TNF-α.
Figure 21:
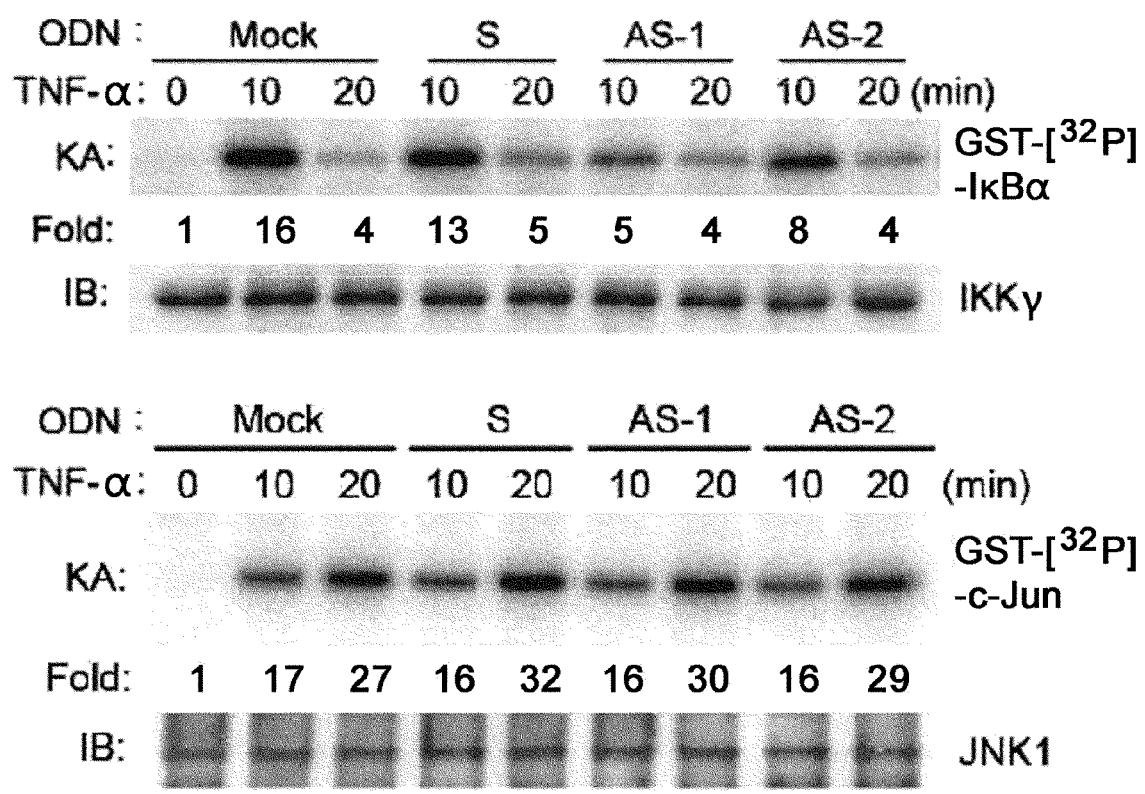
Figure 22:
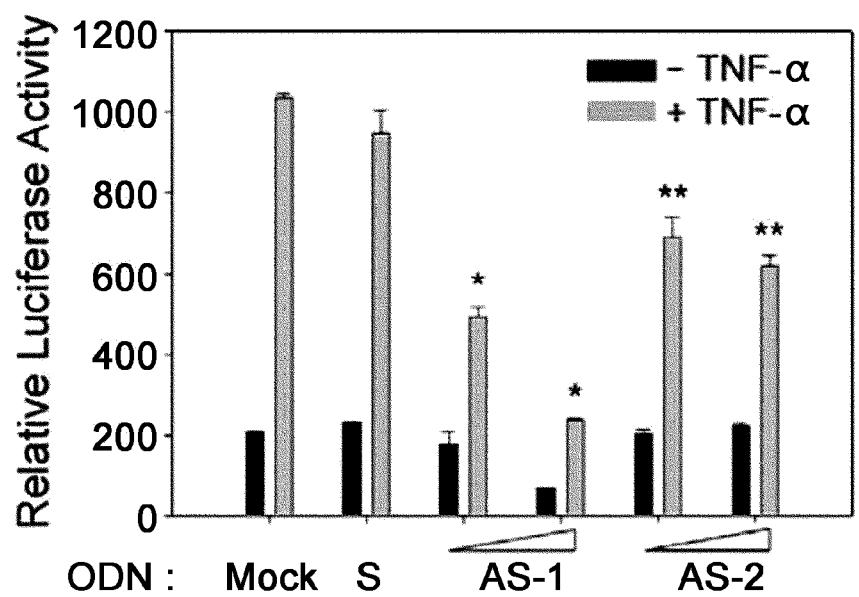
Figure 23:
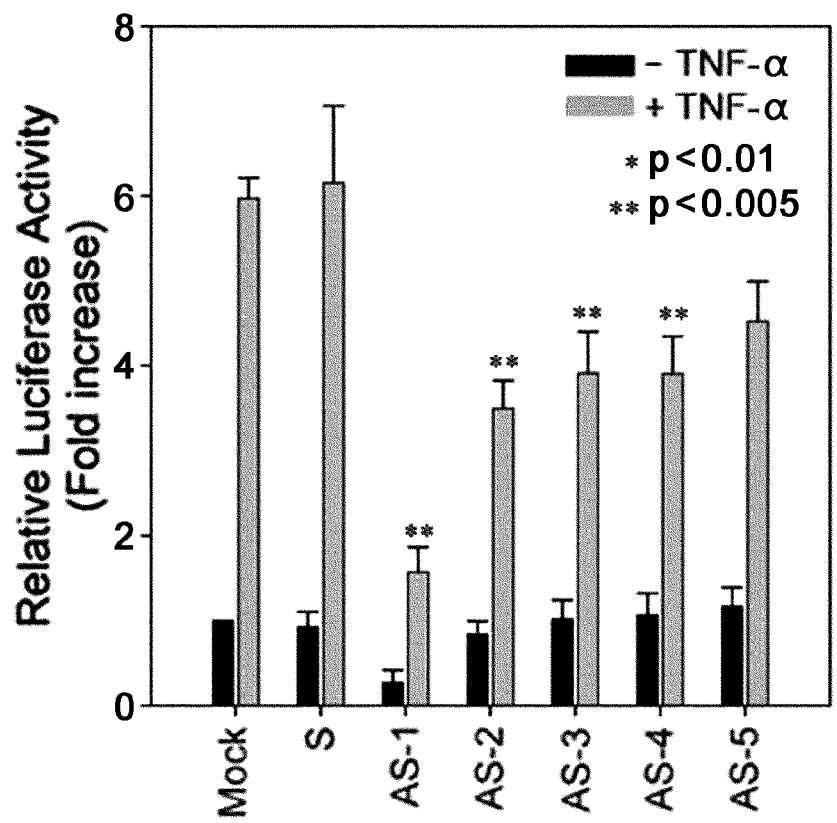
Figure 24:
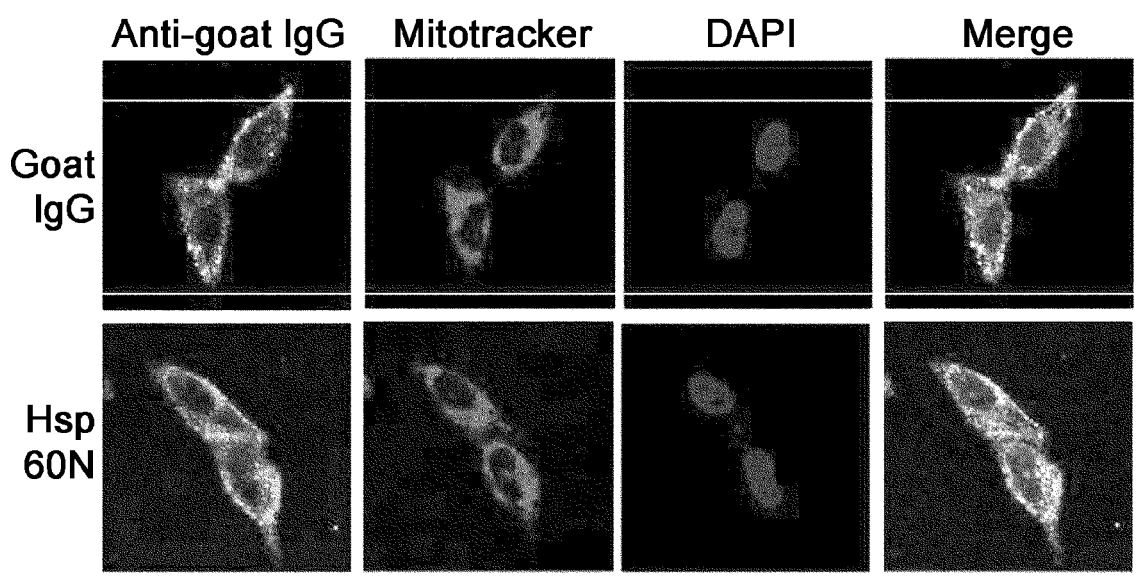
FIGS. 24 to 27 show that Hsp60-specific antibody blocks IKK/NF-κB activation.
Figure 25:
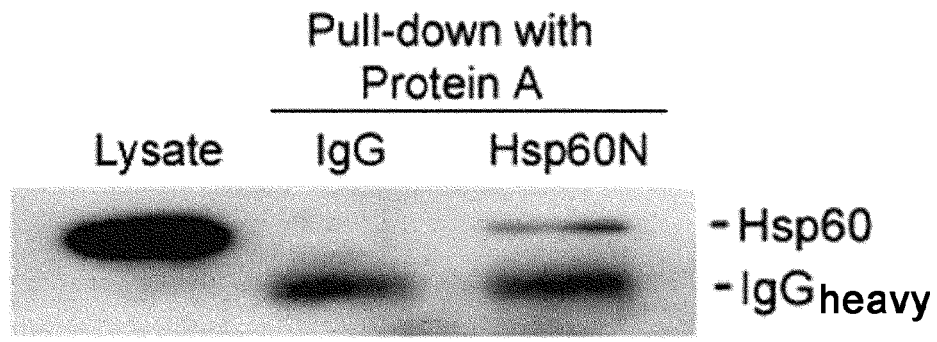
Figure 26:
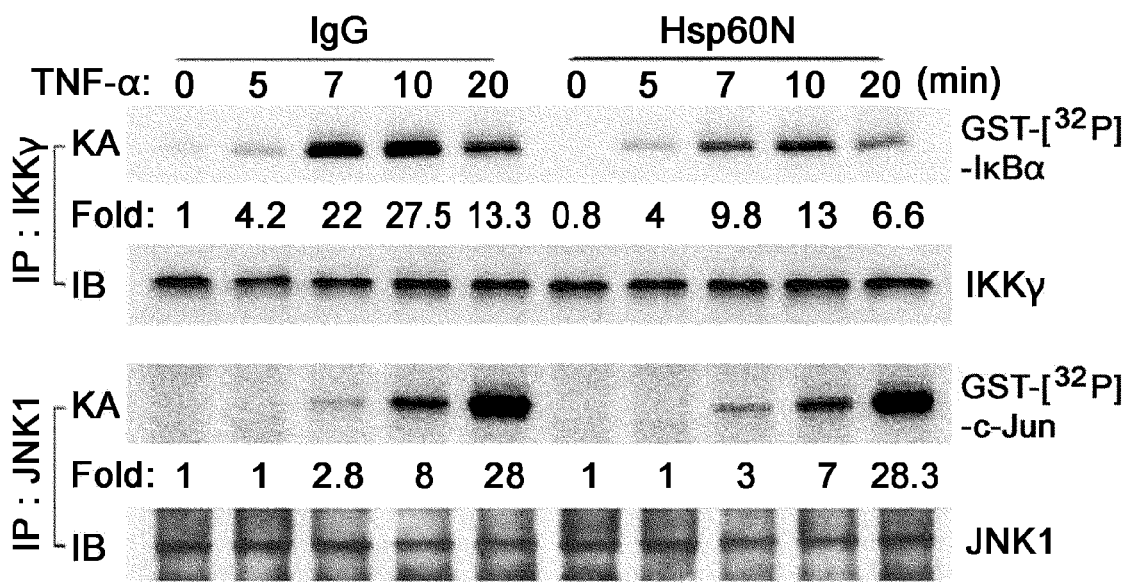
Figure 27:
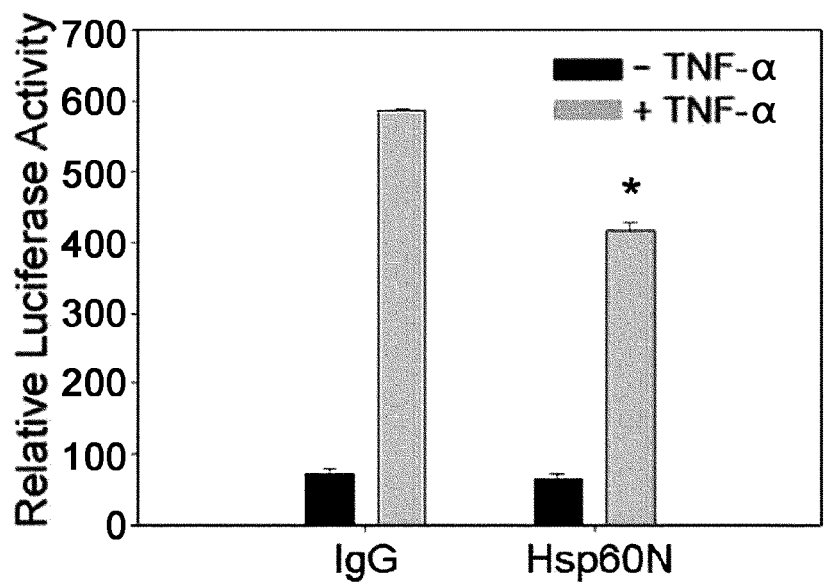

The TNF-α-induced IKK/NF-κB activation was then examined in the AS-ODN-transfected cells. An in vitro kinase assay showed that the transfection of AS-ODNs appreciably reduced the IKK activation in response to TNF-α by 60% compared to that of the mock or S-ODN (FIG. 21). However, the AS-ODNs had no effect on the MAP kinase activation in response to TNF-α (FIGS. 21 and 15), revealing the specific effect of the Hsp60 AS-ODNs on IKK activation. Furthermore, the AS-ODNs almost completely abolished the NF-κB transcriptional activation in response to TNF-α, whereas S-ODN did not, compared to mock-treated cells (FIGS. 22 and 23). Owing to its knockdown efficacy, AS-1 is more potent than AS-2 to AS-5, and all of AS-2 to AS-5 inhibited NF-κB transcriptional activation even though they are weaker than AS-1. However, the transfection of ODNs itself did not induce basal NF-κB activation, indicating no off-target effect of ODNs. In addition, the reductive effect of AS-ODNs on NF-κB transcriptional activity was also evident in 293 T and A549 cells (FIG. 17). An additional control experiment showed that the AS-ODNs had no effect on other transcription factor activation, such as AP-1, NF-AT, and ORE (FIG. 16). A similar study was performed by blocking the cytosolic Hsp60 using a specific antibody (Hsp60N), which has been used for immunoprecipitation and immunostaining of Hsp60 (FIG. 1). The antibody transduction was achieved by a peptide-mediated protein delivery system [Morris M C et al., Nat Biotechnol 19:1173-1176 (2001)]. The control goat IgG and Hsp60N antibody were found to be successfully delivered, to cytoplasm, as being not merged with Mitotracker (FIG. 24), and Hsp60N, but not control IgG, bound to Hsp60 (FIG. 25). This result indicates that the delivered antibody can act as a function blocker. Then, IKK/NF-κB activation was examined in antibody-transduced cells. The Hsp60N antibody evidently reduced the IKK activation in response to TNF-α by 50% of the level obtained with the control IgG (FIG. 26). In contrast, TNF-α-induced JNK activation was not affected, which again proves that the role of Hsp60 is specific to the IKK activation. Consistently, the Hsp60N antibody significantly reduced the transcriptional activity of NF-κB (FIG. 27). The data collectively conclude that cytosolic Hsp60 promotes the TNF-α-induced IKK/NF-κB signaling.

Figure 28:
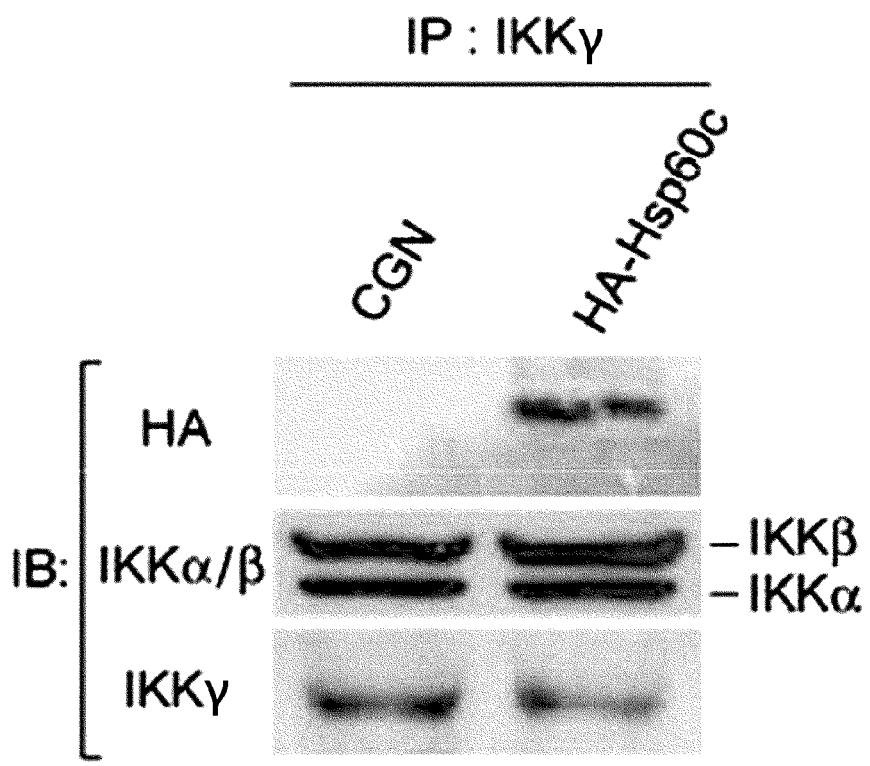
FIGS. 28 to 31 show that cytosol-targeted expression of Hsp60 promotes TNF-α-induced IKK/NF-κB activation. Cells were transfected with either control (CGN) or Hsp60c-encoding plasmid (HA tag) for 24 hours and then treated with TNF-α.
Figure 29:
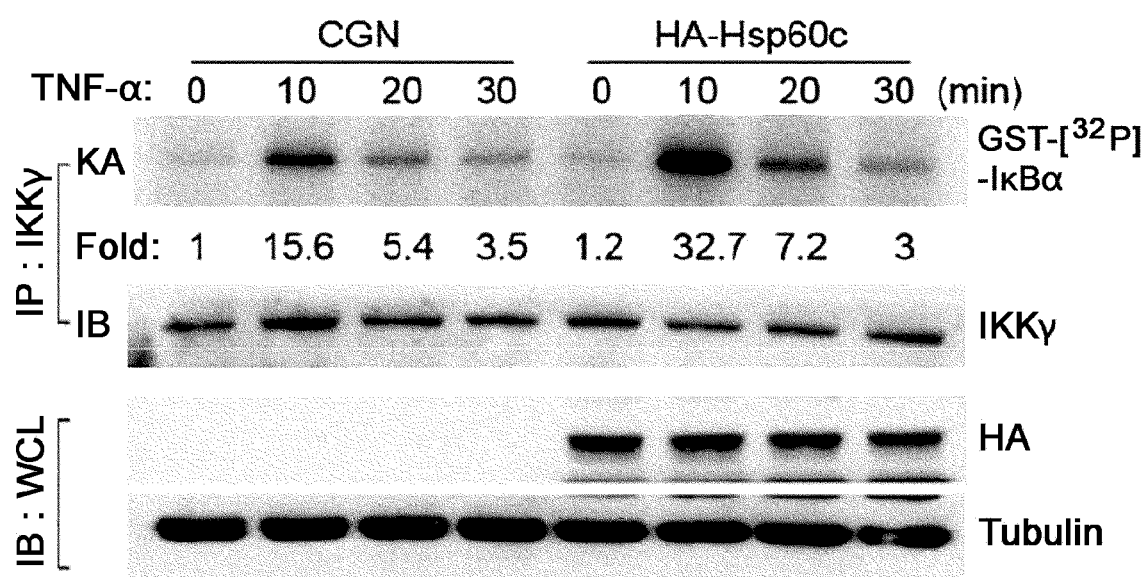
Figure 30:
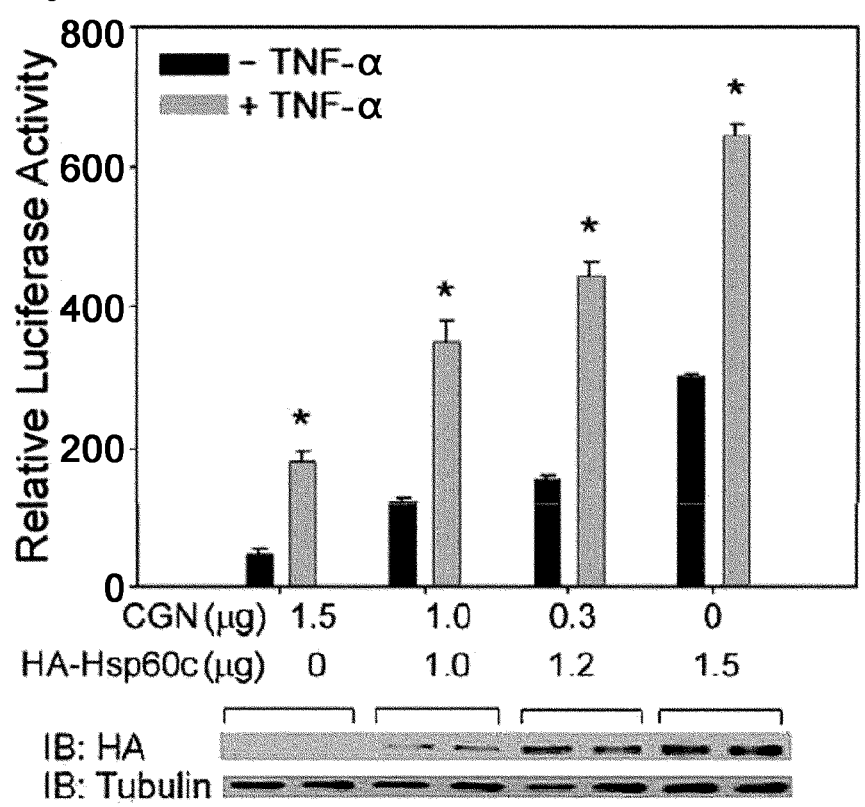
Figure 31:
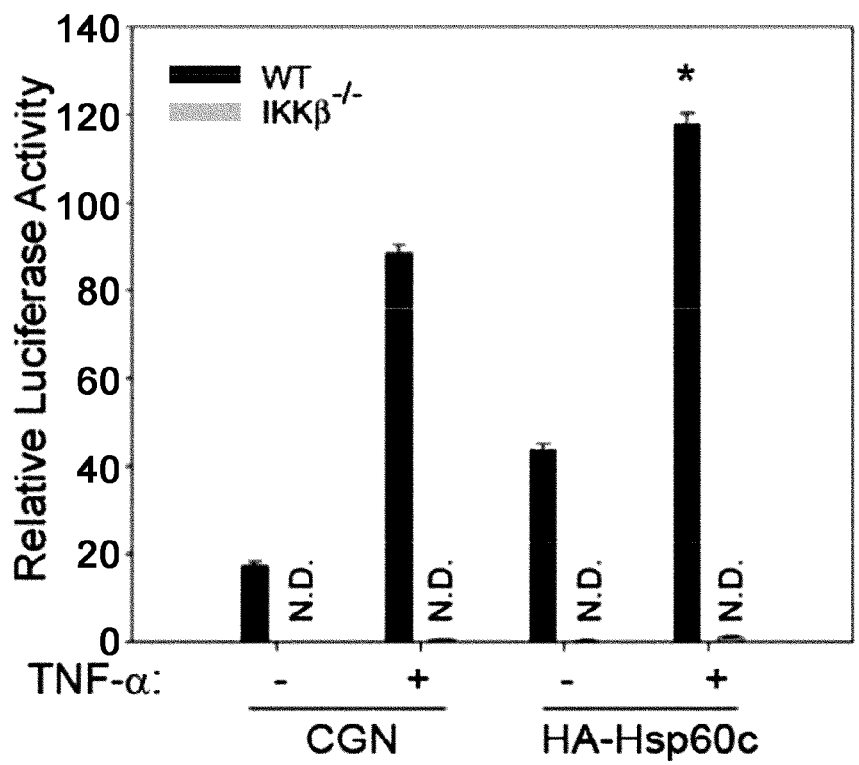
Figure 32:
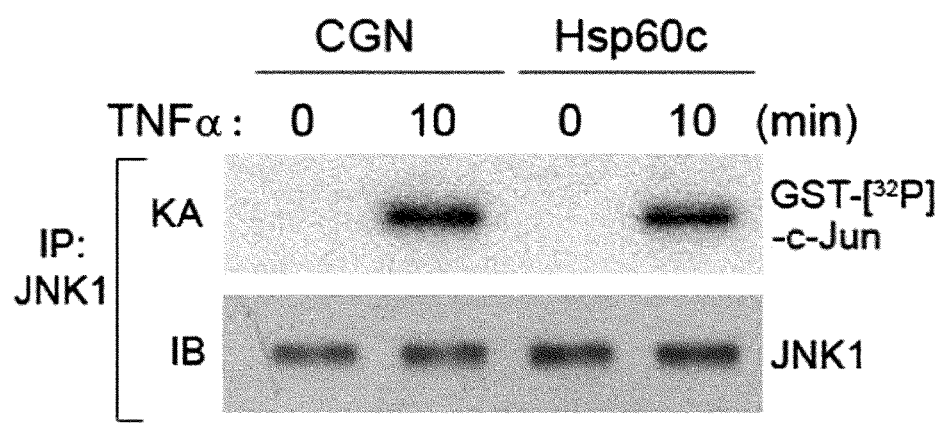
FIGS. 32 to 35 show selective role of cytosolic Hsp60 (Hsp60c) in IKK/NF-κB signaling.
Figure 33:
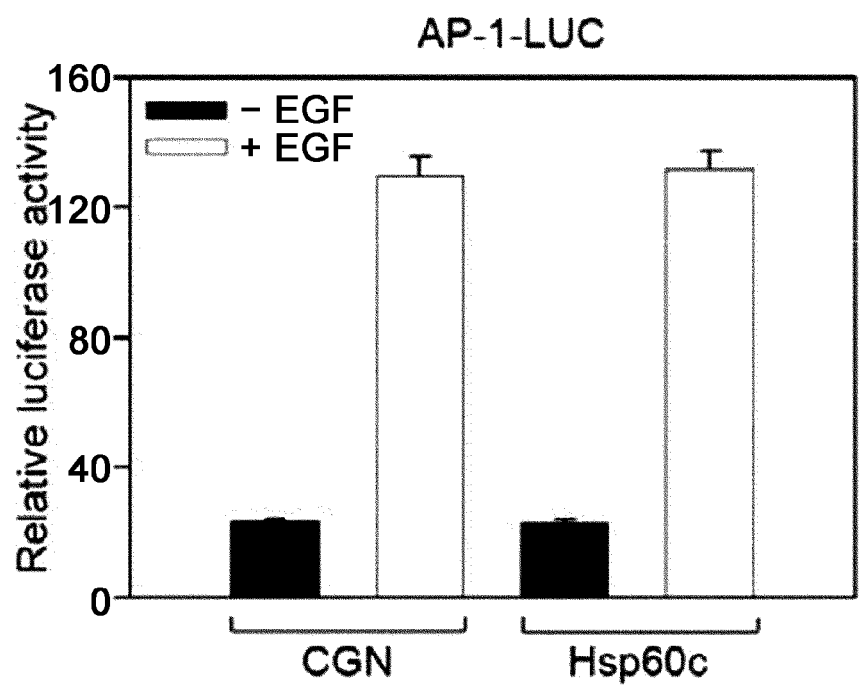
Figure 34:
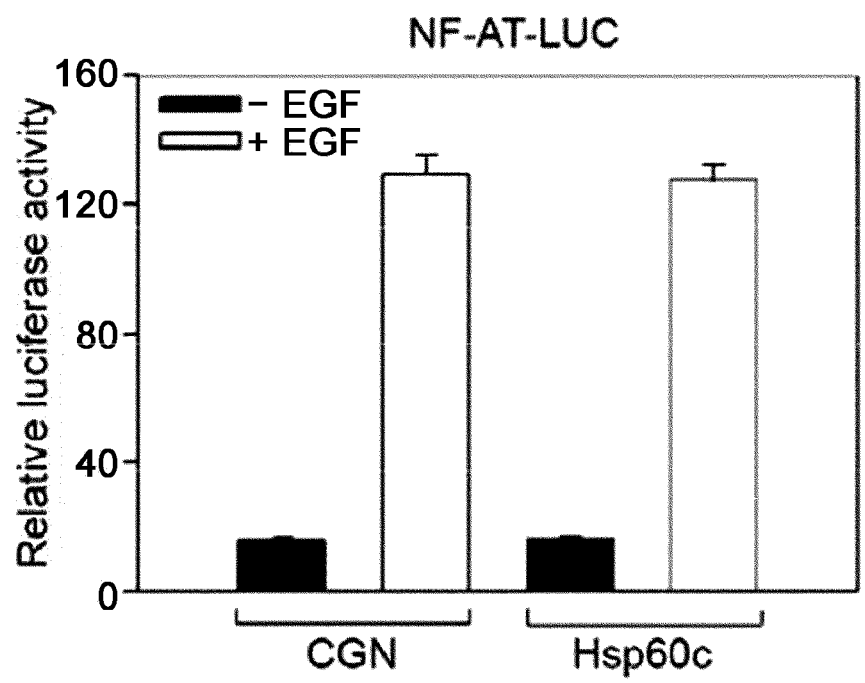
Figure 35:
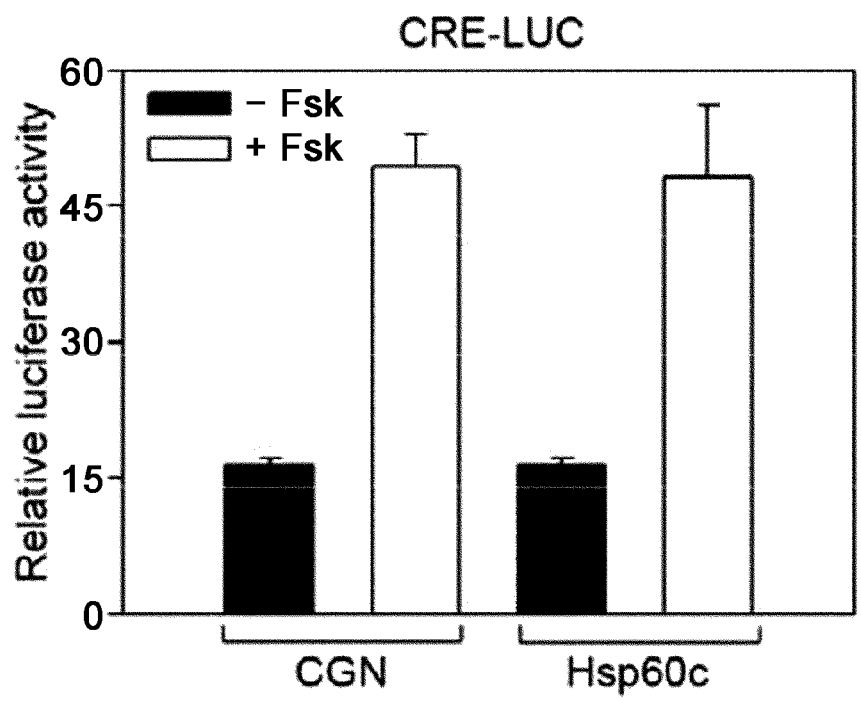

Ectopic Expression of Cytosol-Targeted Hsp60Sufficiently Promotes IKK/NF-κ Activation Conversely, the role of cytosolic Hsp60 in IKK/NF-κB pathway was addressed by over-expression of cytosol-targeted Hsp60c. The ectopically-expressed Hsp60c was found to associate with the IKK complex (FIG. 28) and markedly enhanced the IKK and NF-κB activation in response to TNF-α (FIGS. 29-30). It should be noted that the ectopic expression of Hsp60c marginally induced the basal IKK and NF-κB activation. The effect of Hsp60c expression in NF-κB activation was completely abolished in IKKβ-deficient cells (FIG. 31), indicating that the regulatory activity of cytosolic Hsp60 is IKK-dependent. Meanwhile, the ectopic expression of Hsp60c did not enhance either JNK activation or the activation of other transcription factors such as AP-1, CRE, and NF-AT (FIGS. 32 to 35). This result indicates that increasing the cytosolic Hsp60 level augments TNF-α-induced IKK/NF-κB activation.

Hsp60 Regulates IKK Phosphorylation at the Activation T-Loop

Figure 36:
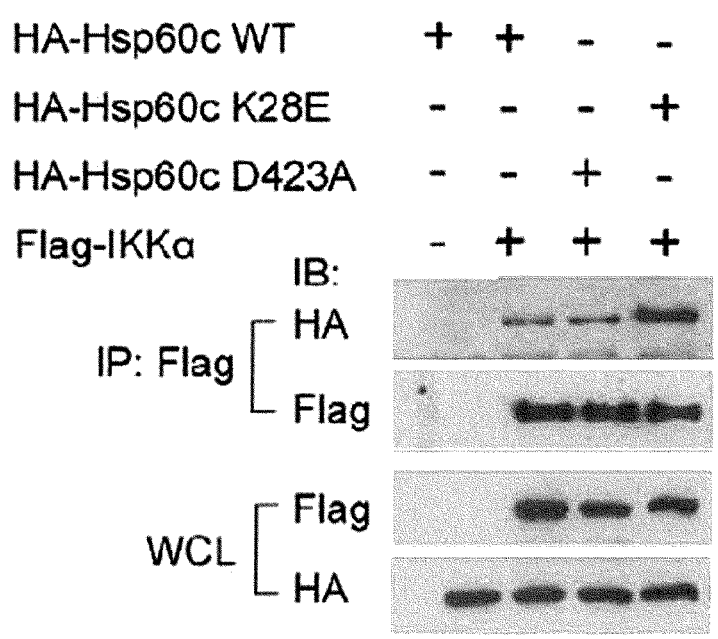
FIGS. 36 to 41 show that cytosolic Hsp60 regulates IKK phosphorylation independently of chaperone activity.
Figure 37:
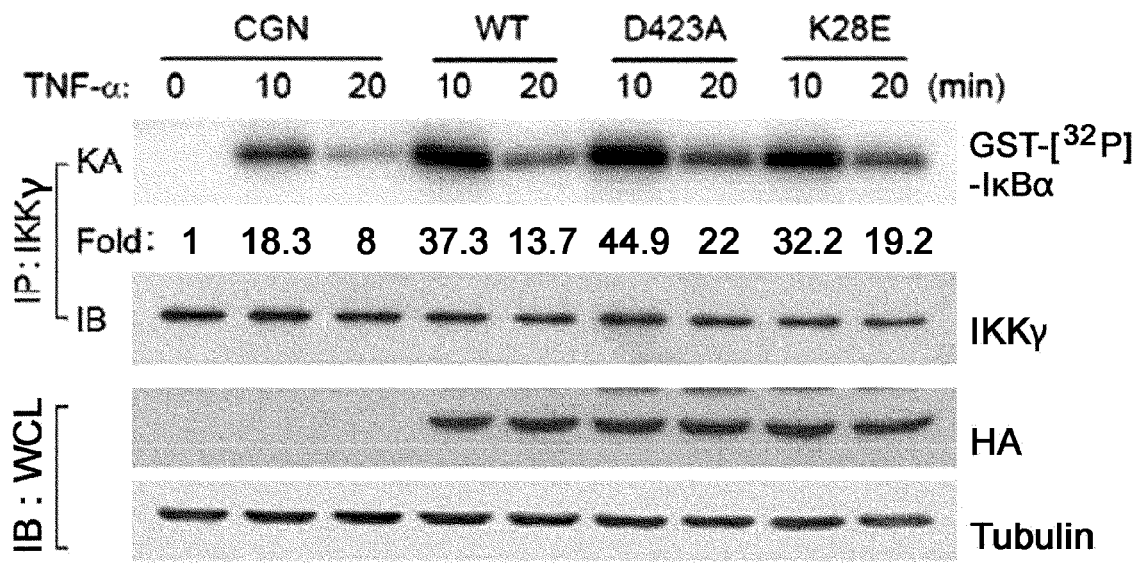
Figure 38:
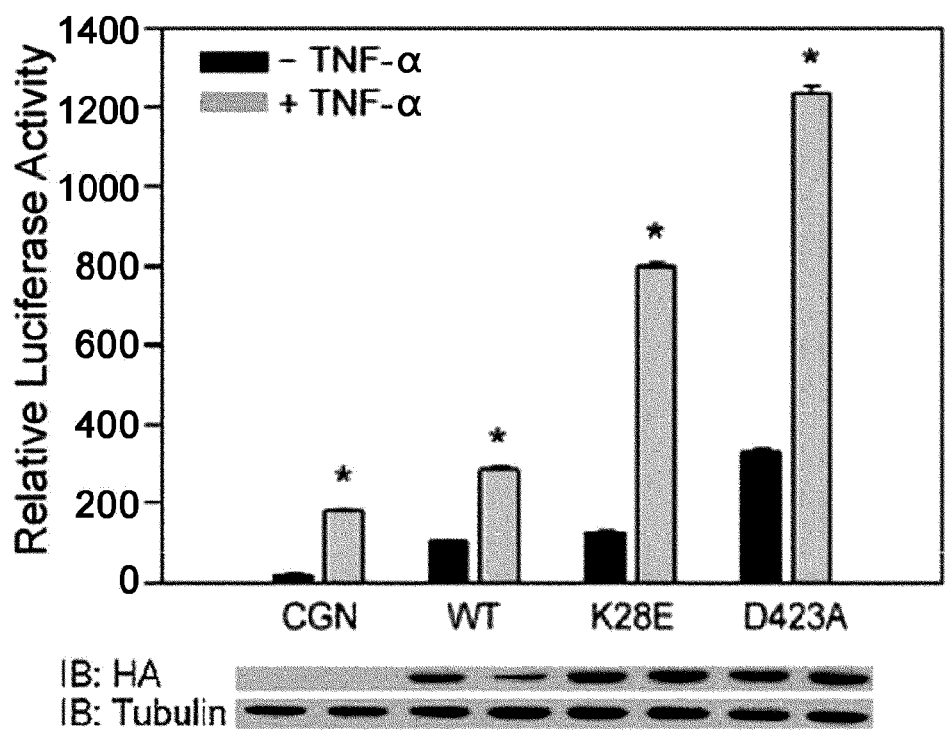

To understand the mechanism underlying the regulatory action of Hsp60 in IKK/NF-κB activation, several experimental approaches were attempted. To determine whether the chaperone activity of Hsp60 is required, the two amino acid residues that are known to be critical for the chaperone activity of Hsp60 were considered. One is a lysine residue (K28), which is involved in the oligomerization of Hsp60 protein. The other is an aspartate: residue (D423), which is an active site residue for ATPase activity. Thus, the Hsp60c mutants, wherein K28 and D423 are substituted with glutamate and alanine respectively, were constructed. The co-transfection experiment showed that both mutants interacted with IKKα as well as or perhaps even better than the wild type (FIG. 36). The IKK activation in response to TNF-α in the Hsp60 mutant-expressing cells was similar to that in the wild type (FIG. 37), indicating that such loss-of-function mutations did not affect the IKK-enhancing activity of Hsp60. Furthermore, TNF-α-induced NF-κB transcription was even enhanced in the Hsp60 mutant-expressing cells at approximately 4-6 times higher compared to the vector control (EIG. 38). The enhancing effect of the mutants was clearly IKKβ-dependent, as tested again in IKKβ-deficient 3T3 cells. Thus, this experiment using the loss-of-function mutants strongly suggest that the cytosolic Hsp60 functions independently of chaperone activity in IKK/NF-κB activation.

Figure 39:
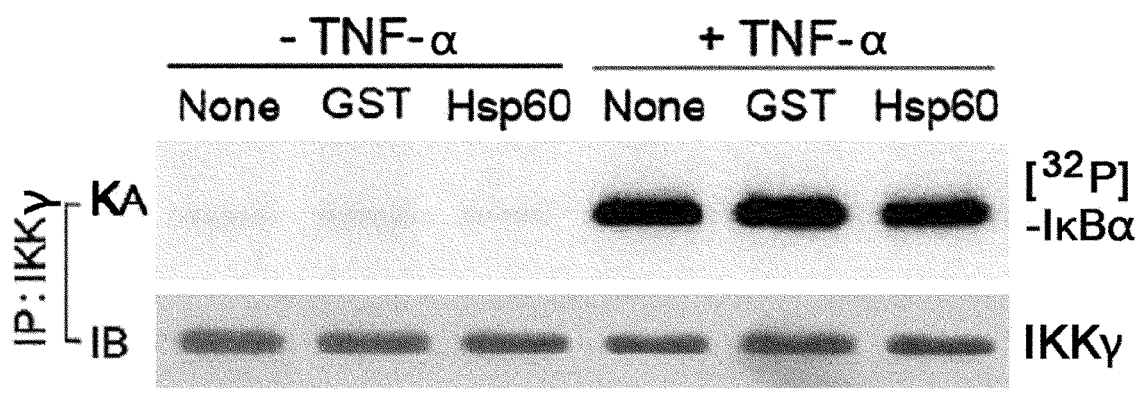

One of the IKK-interacting protein, ELKS, has been shown to mediate the IκB recruitment to IKK complex. To test this mode of action, the recombinant Hsp60 protein was directly added into the IKK kinase reaction, where the activated IKK complex is incubated with full-length human IκB as a substrate. The in vitro kinase activity of the activated IKK toward IκB was not affected by the presence of Hsp60 protein (FIG. 39), indicating that Hsp60 is not involved in the interaction of IKK and its substrate IκB.

Figure 40:
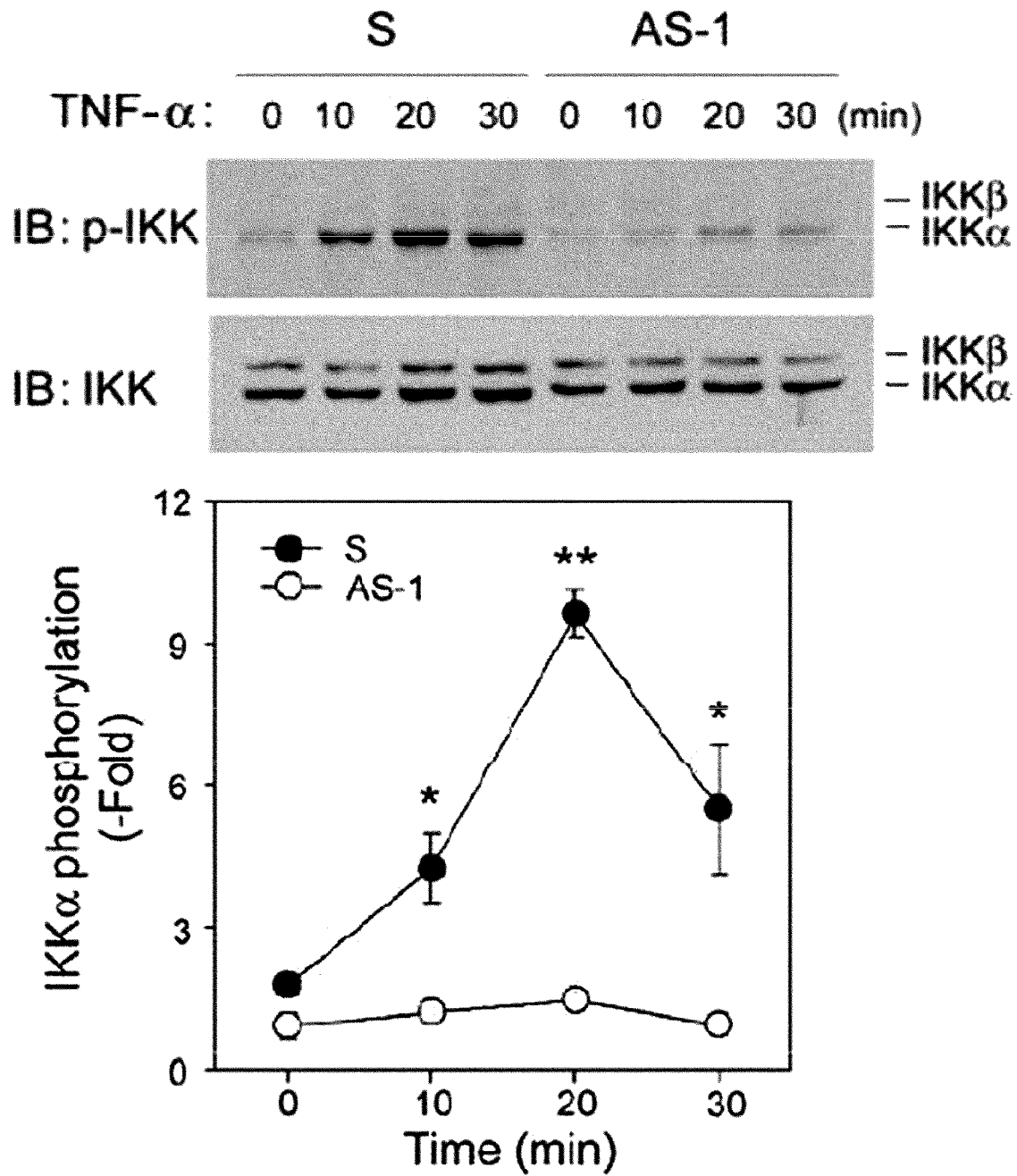
Figure 41:
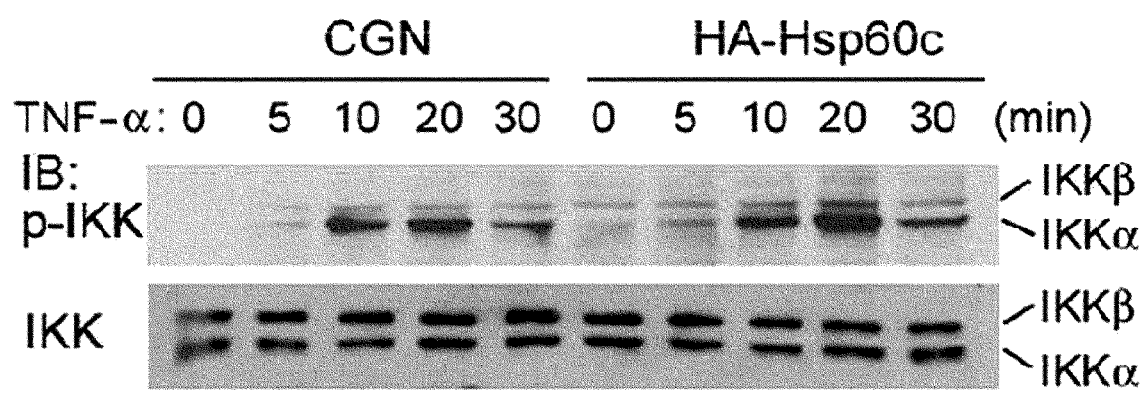

Also, a direct involvement of cytosolic Hsp60 in IKK activation was addressed by examining the activation-dependent serine phosphorylation in the T-loop of IKKα/β. The AS-ODN transfection markedly abolished the TNF-α-induced phosphorylation of IKK at Ser178/181, indicating that the phosphorylation-dependent IKK activation was impaired (FIG. 40). Conversely, the ectopic expression of Hsp60c resulted in an increase of IKK phosphorylation (FIG. 41). Overall, the data of the present invention indicate that the cytosolic Hsp60 is involved in the phosphorylation-dependent IKK activation, rather than the chaperone-dependent stabilization of IKK complex.

Cytosolic Hsp60 Affects the NF-κB Target Gene Expression and Cell Survival

Figure 42:
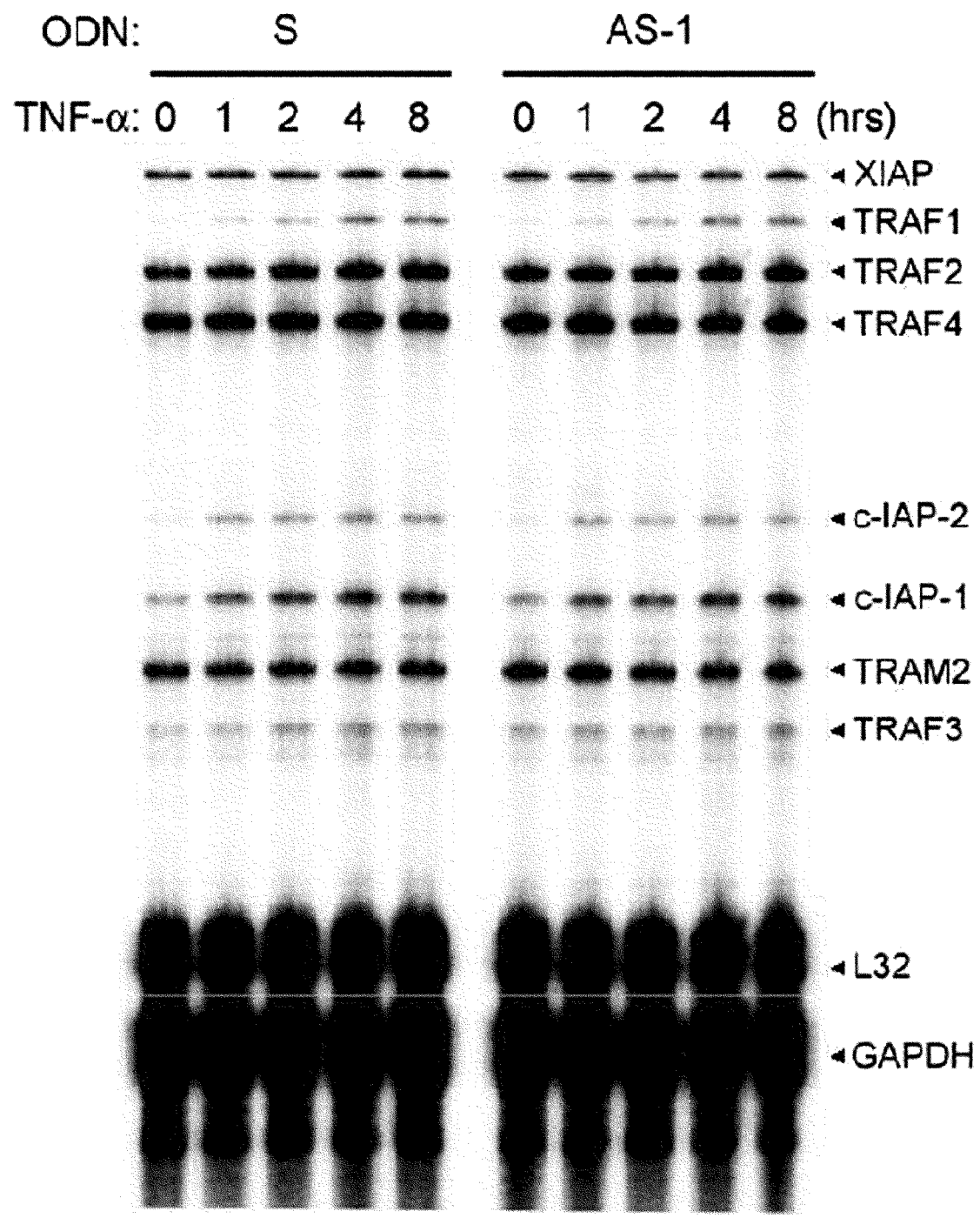
FIGS. 42 to 49 show that loss of cytosolic Hsp60 induces cell death in response to TNF-α by inducing ROS and ASK-1 activation.
Figure 43:
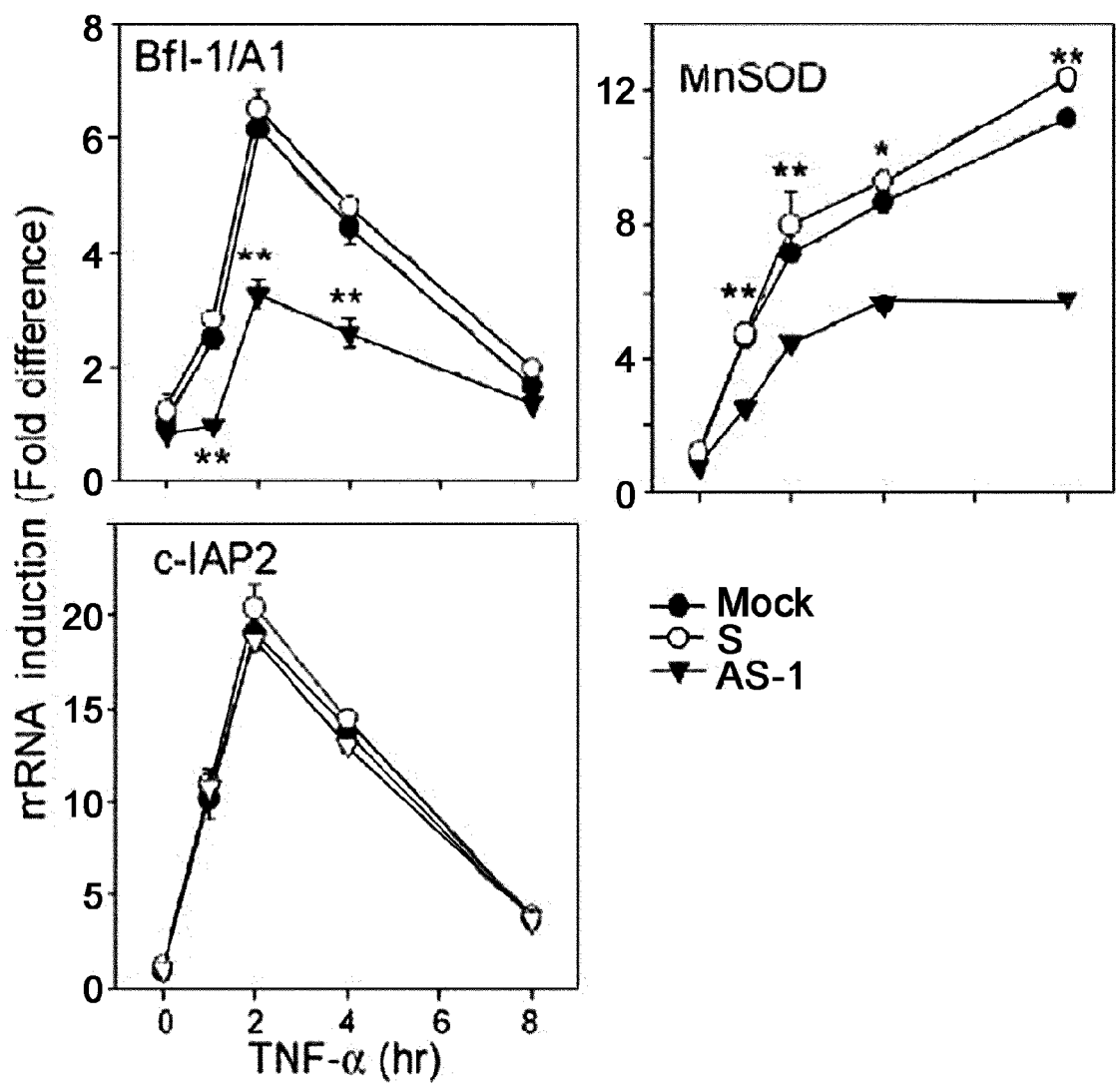
Figure 44:
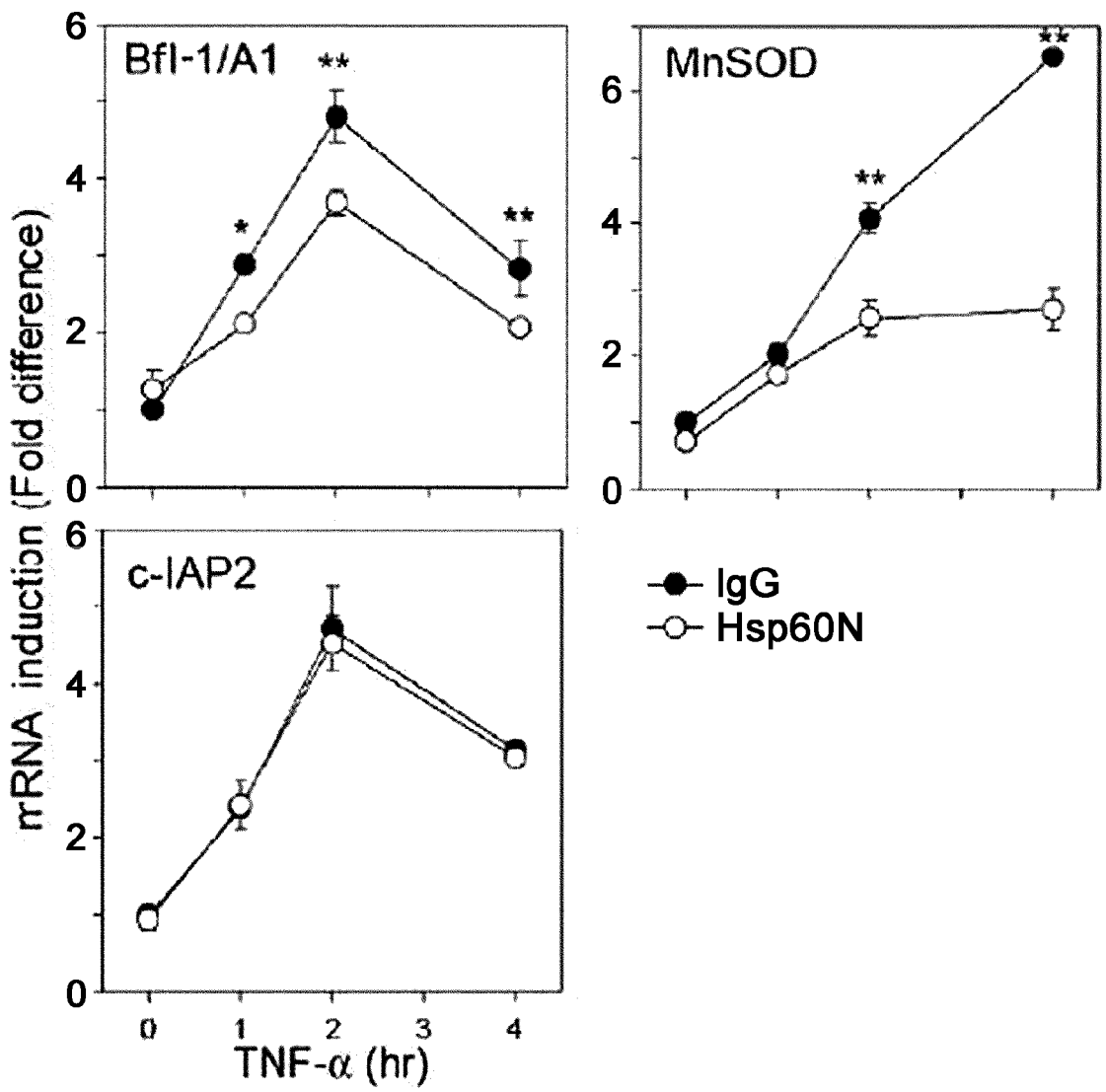

To determine the significance of cytosolic Hsp60-mediated regulation of the IKK/NF-κB pathway, the present inventors examined the expression of NF-κB target genes in ODN-transfected cells. When the expression of anti-apoptotic genes was screened by an RNase protection assay, the expression of TRAF1, c-IAP1, and C-IAP2 were not affected by AS-ODN transfection (FIG. 42). Interestingly, the AS-ODN significantly diminished the induction of only MnSOD and Bfl-1/A1 expression in response to TNF-α (FIG. 43). The Hsp60N antibody also significantly reduced the induction of these genes (FIG. 44). It was again confirmed that the induction of the C-IAP2 expression was not affected in either case. Thus, the results indicate that the regulation of the IKK activation by cytosolic Hsp60 influences the expression of selective NF-κB target genes.

Figure 45:
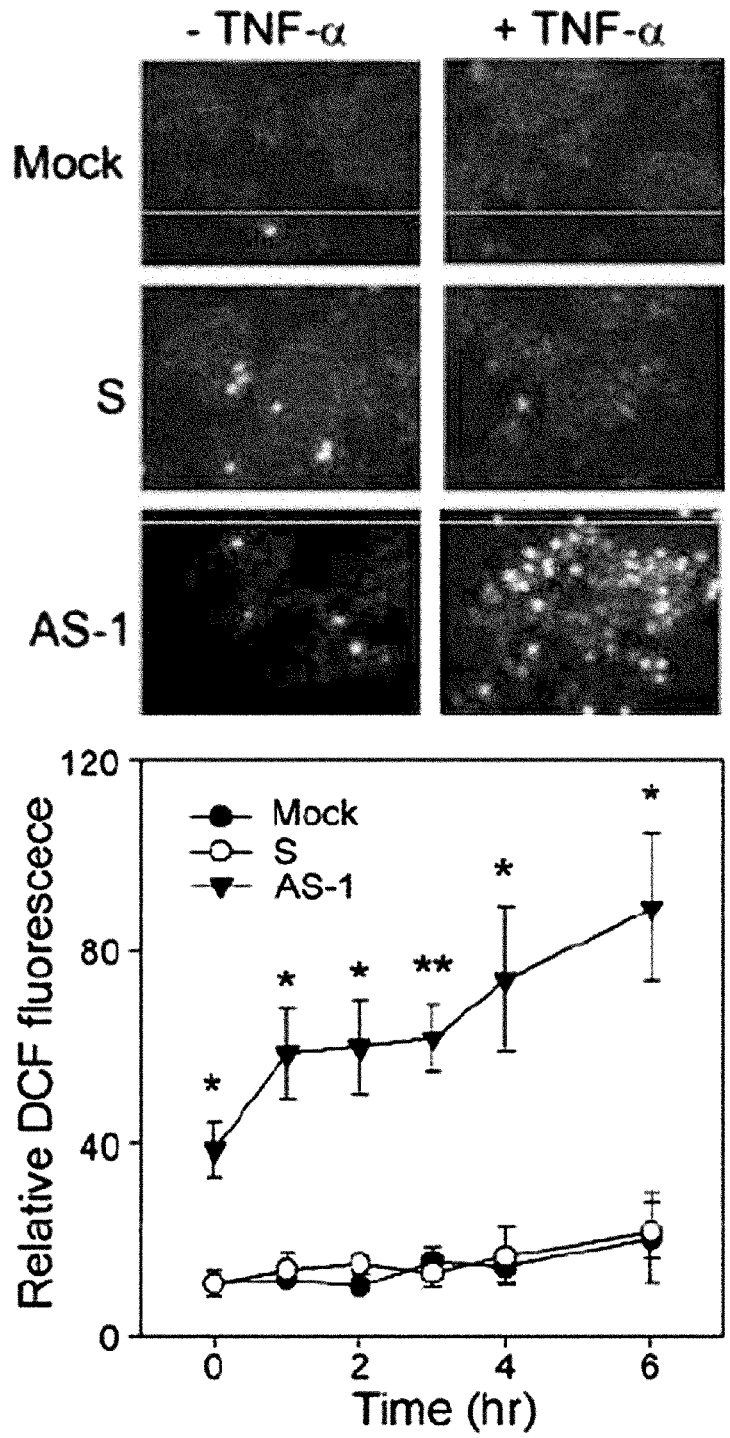
Figure 46:
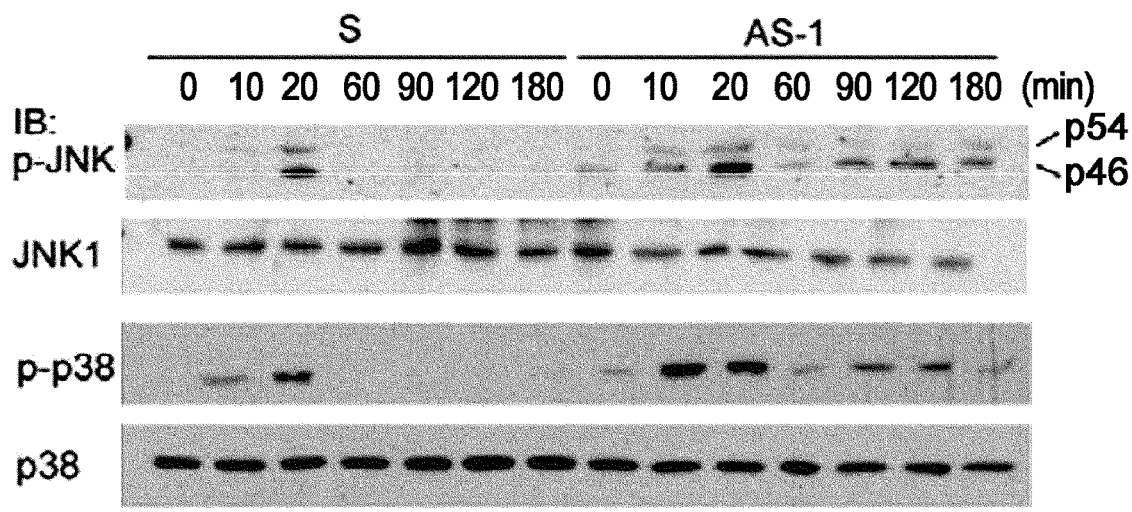
Figure 47:
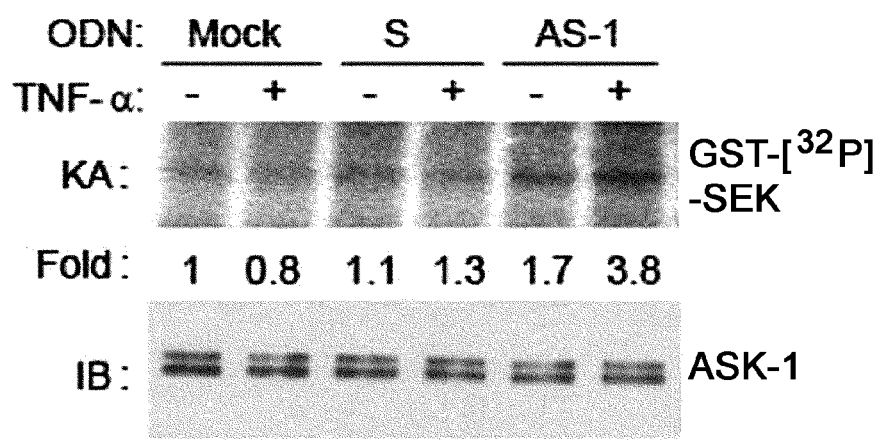
Figure 48:
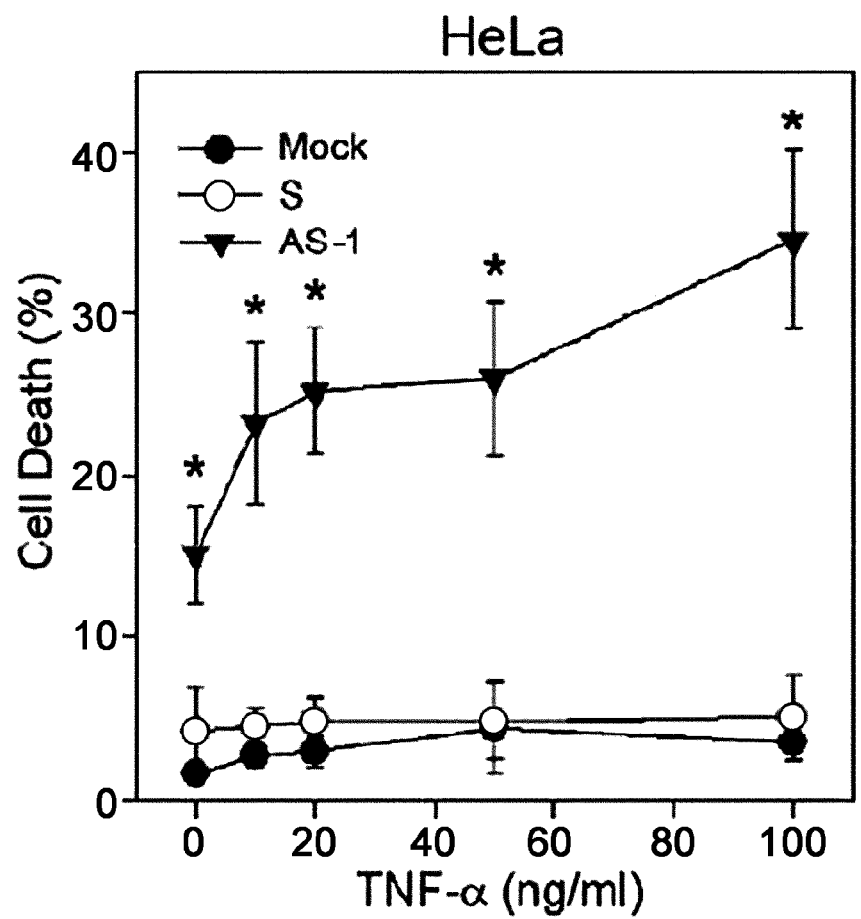

The present inventors next wondered whether such regulation of selective target genes has an impact on cell survival. Since there is a possibility that MnSOD and Bfl-1/A1 function to suppress the mitochondrial derived reactive oxygen species (ROS), the level of cellular ROS was examined in ODN-transfected cells using an oxidation sensitive fluorescence dye, CM-H2DCFDA. The AS-ODN transfection induced a marked increase of cellular ROS in response to TNF-α treatment, in a time-dependent manner, compared to mock or S-ODN transfection (FIG. 45). Since the enhanced ROS level is linked to cell death via the sustained JNK activation, the sustained activation of stress-activated protein kinases (JNK and p38 MAPK) was examined. Unexpectedly, the activation of both JNK and p38 MAPK were found to be clearly sustained in AS-ODN-transfected cells (FIG. 46). The ASK-1 MAP3K is known to be responsible for the sustained activation of JNK and p38 in the ROS-mediated cell death. Indeed, the ASK-1 activation was significantly induced in AS-ODN-transfected cells (FIG. 47). As a consequence of this signaling pathway including ASK-1 activation, the AS-ODN resulted in a marked induction of TNF-α-induced cell death in HeLa cells, whereas the mock or S-ODN did not at all (FIG. 43). Likewise, the AS-ODN enhanced TNF-α-induced cell death in colon carcinoma cell lines, which showed significantly increased level of cytosolic Hsp60 (FIG. 49). It should be noted that the AS-ODN transfection by itself resulted in the basal activation of ROS, ASK-1, and cell death.

Along with the evidence that the Hsp60c overexpression induced the basal IKK/NF-κB activation (FIGS. 28 to 31), cytosolic Hsp60 seems likely to direct cell survival in resting cancer cells. Collectively, our results suggest that the selective regulation of MnSOD and Bfl-1/A1 expression by cytosolic Hsp60 sufficiently influences cell survival via suppressing mitochondrial ROS burst.

Cytosolic Hsp60 Protects Host Cells Against Stressed Conditions

Figure 50:
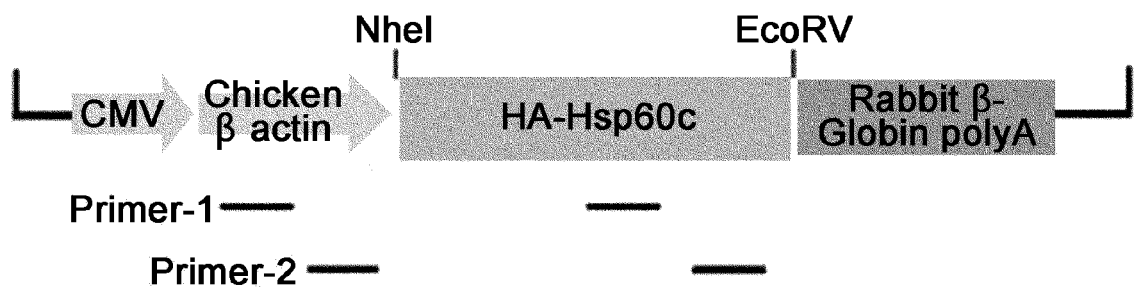
FIGS. 50 to 55 show that cytosolic Rsp60 protects hepatic cells in vivo from stress-induced apoptosis via IKK activation.
Figure 51:
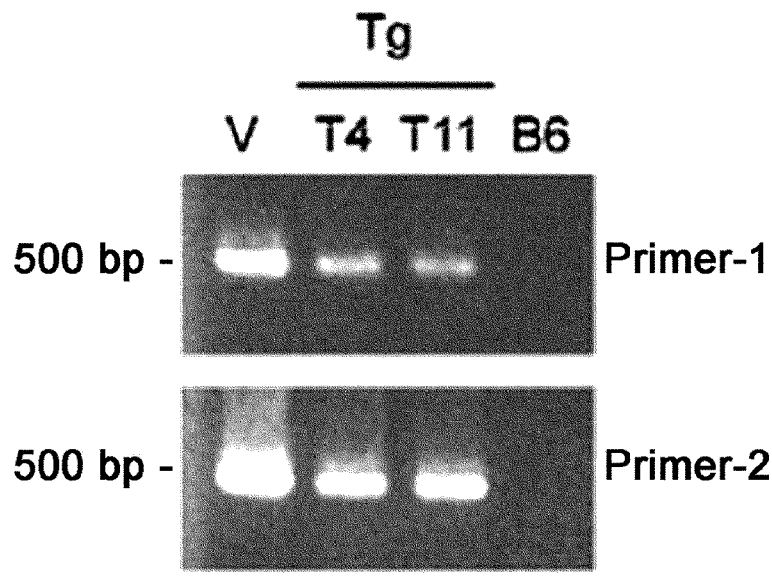
Figure 52:
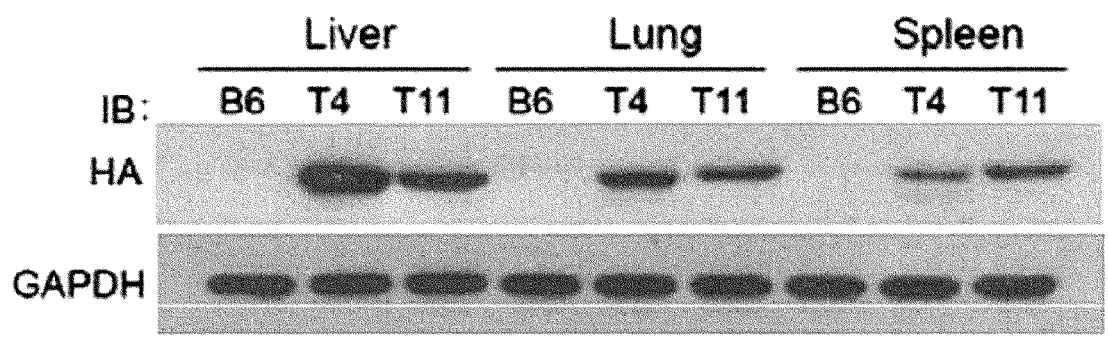
Figure 53:
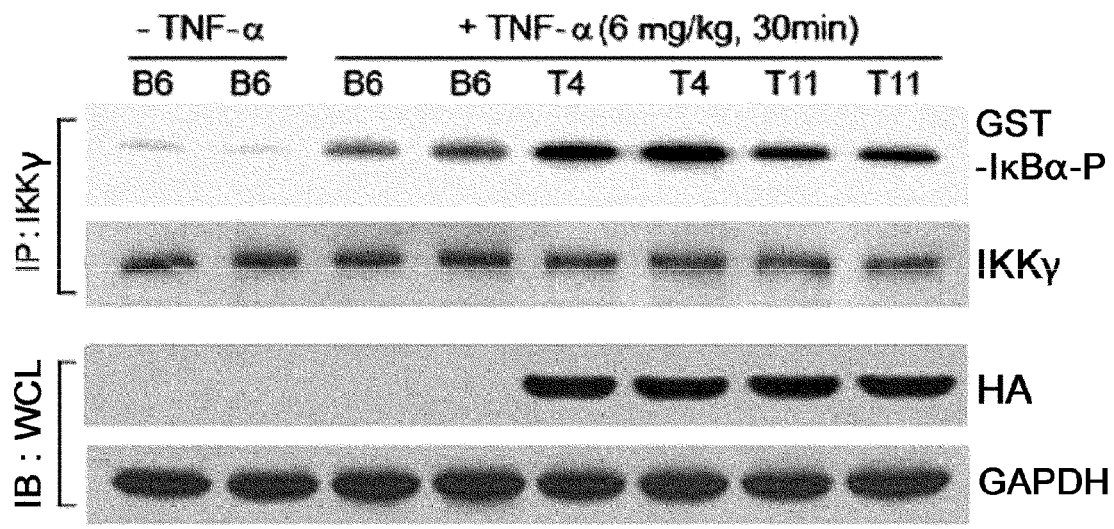
Figure 54:
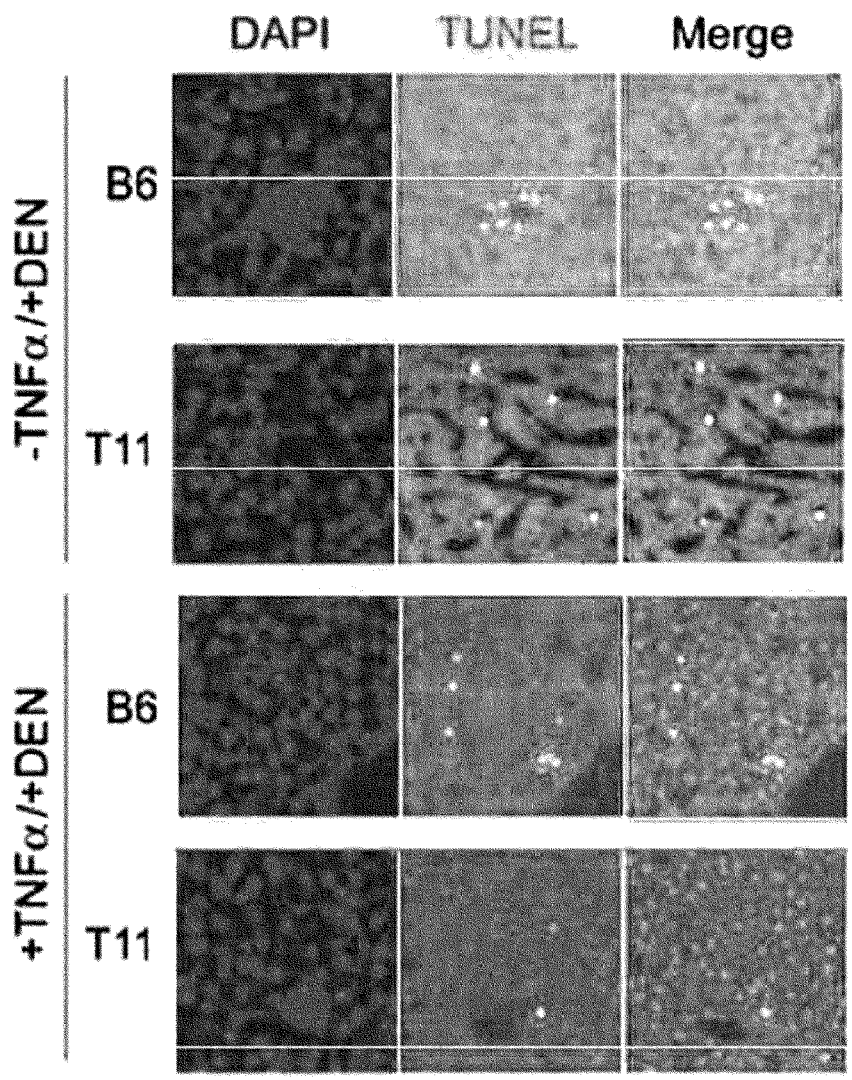
Figure 55:
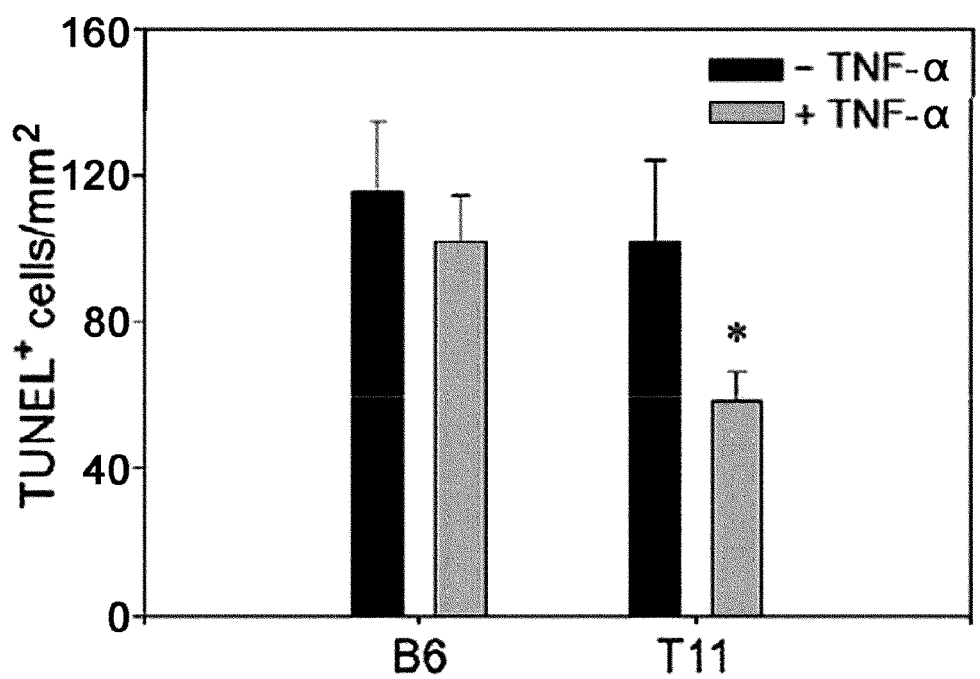
Figure 56:
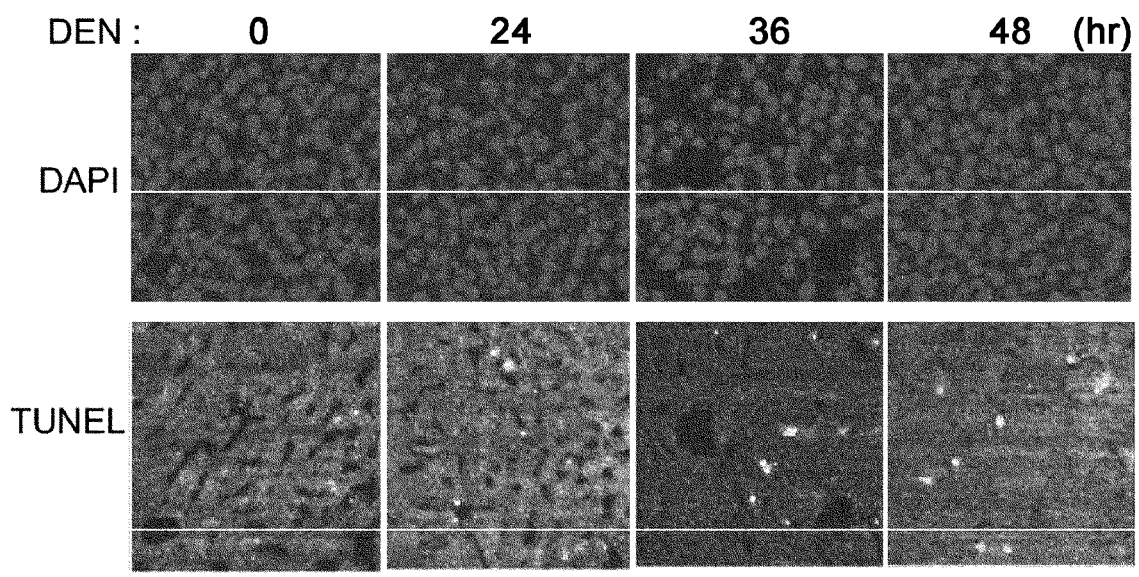
FIGS. 56 to 57 show that DEN induces hepatic cell apoptosis. The four-week old C57BL/6J male mice were intraperitoneally injected with DEN (10 mg/kg). After the indicated time periods of DEN treatment, animals were sacrificed and processed to prepare tissue sections and images as described in Experimental Procedures. TUNEL positive cells were counted in three tissue sections per mouse. Representative images (FIG. 56) are shown. Data in the quantitative graph (FIG. 57) are mean±S.D. of TUNEL positive cells per unit area.
Figure 57:
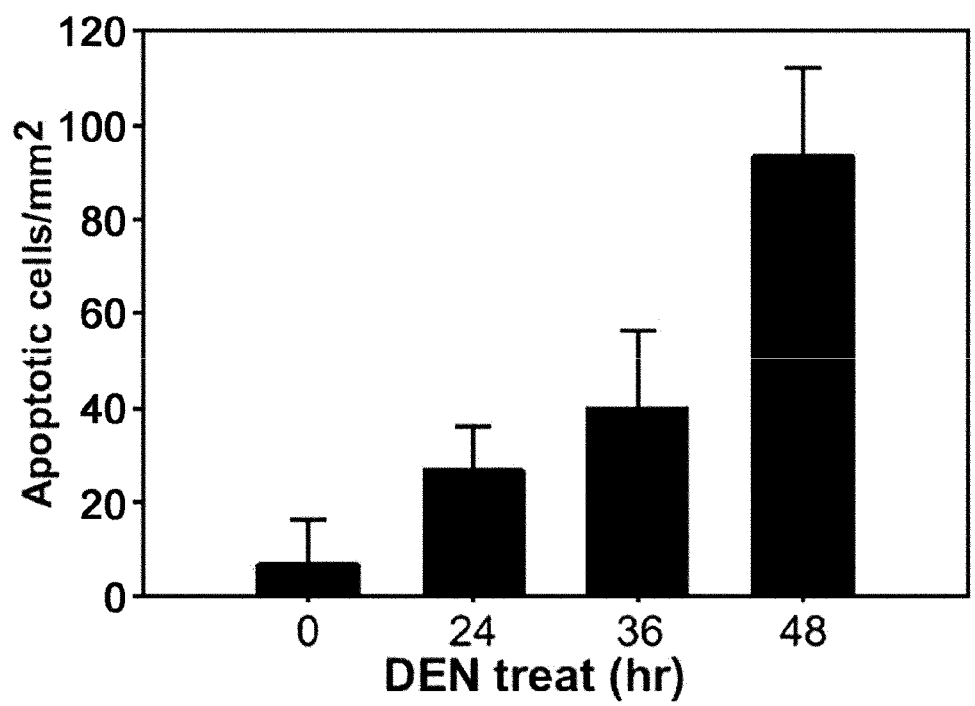
Figure 58:
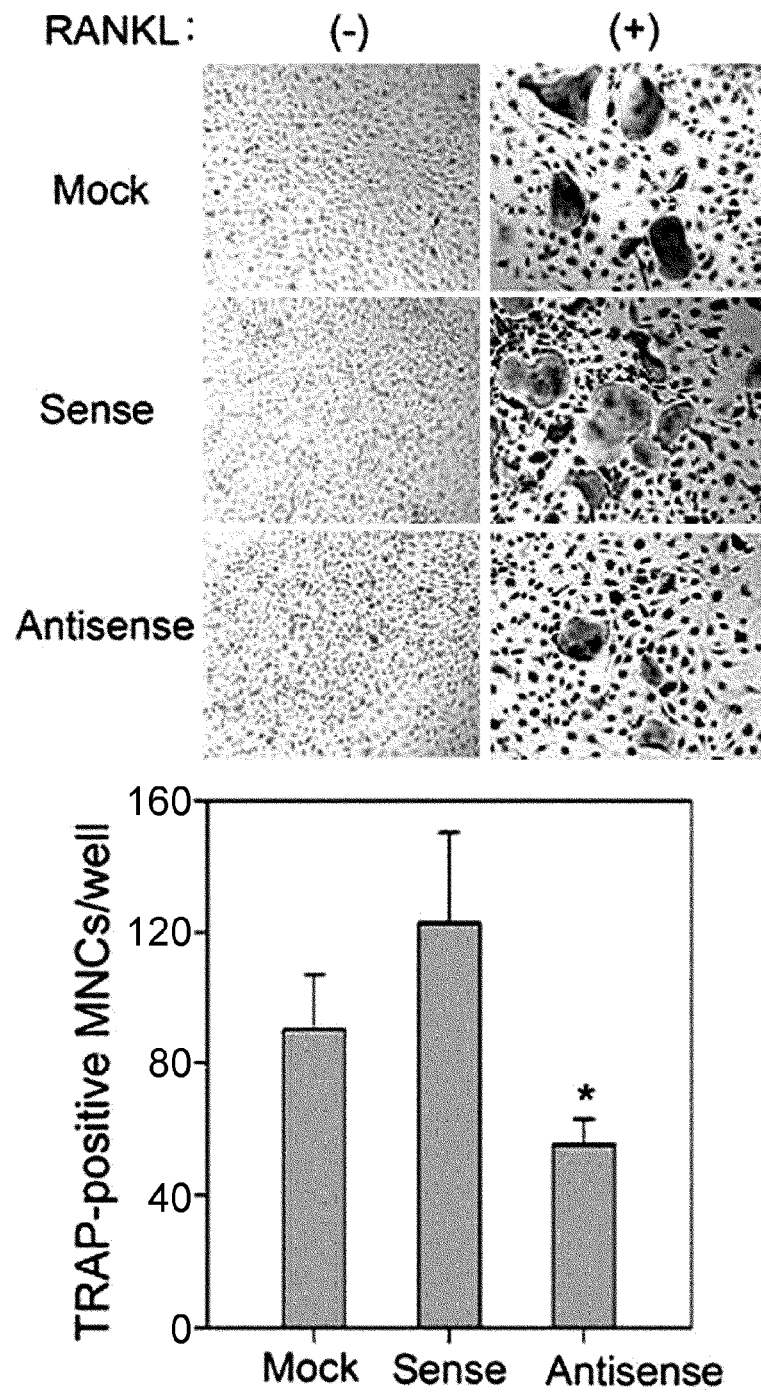
FIGS. 58 to 61 show that cytosolic Hsp60 plays an important survival role in the biological system.
Figure 59:
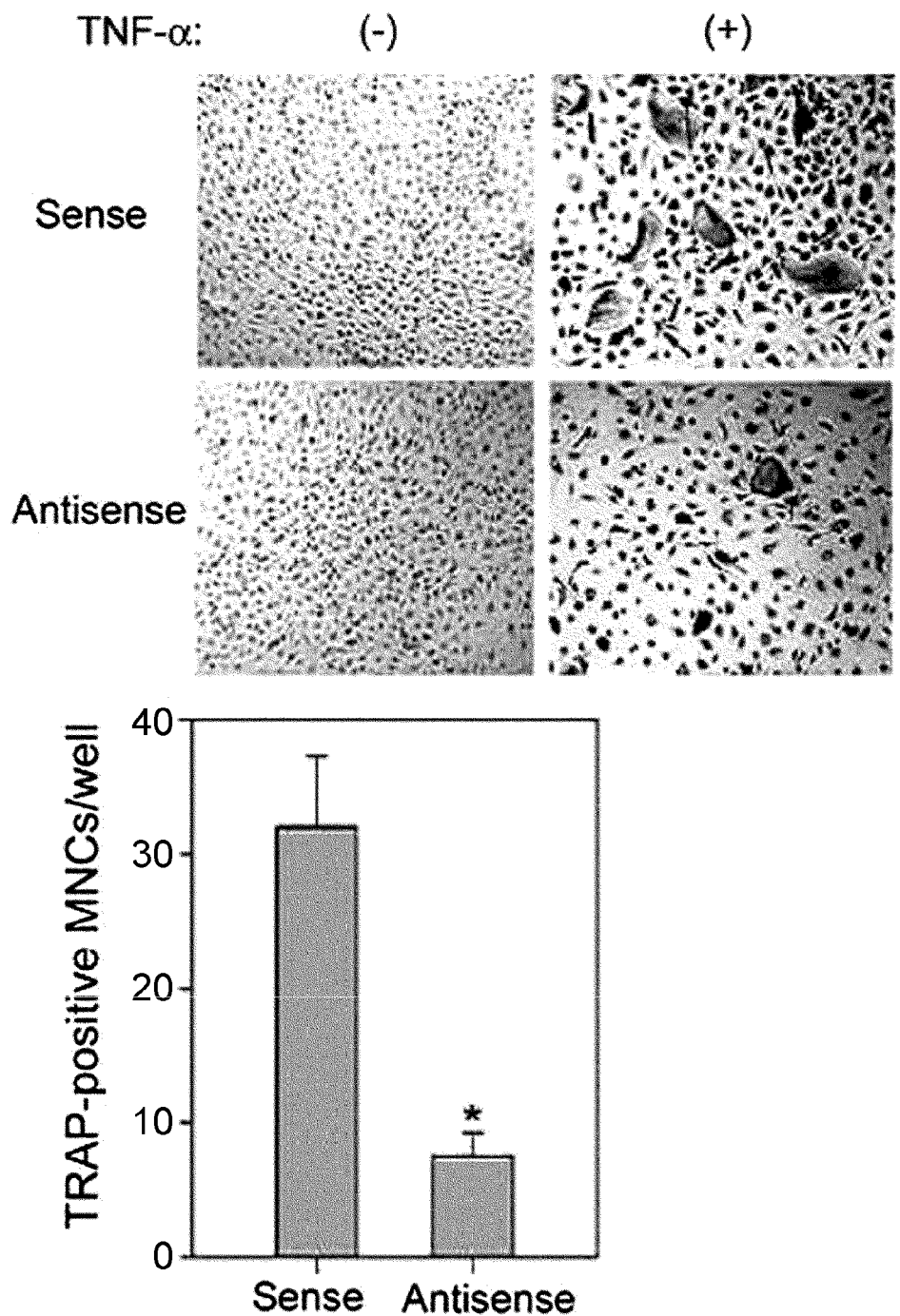

The pro-survival activity of cytosolic Hsp60 was investigated in vivo. To do this, transgenic mice expressing Hsp60c were generated (FIGS. 50-51). The Hsp60c protein was successfully expressed in various tissues, including liver, spleen, and lung (FIG. 52). The IKK activation was markedly enhanced in the Hsp60c-expressing transgenic mice compared to the control B6 mice when TNF-α was intravenously injected (FIG. 53). The result indicates that the cytosolic Hsp60 enhanced the TNF-α-induced IKK activation in vivo. The present inventors then sought an animal model wherein the IKK/NF-κB-dependent cell survival is involved the diethylnitrosamine (DEN)-induced hepatocyte death. The apoptotic cell death of hepatocytes was indeed increased after DEN injection in four-week-old male mice (FIGS. 56 to 57). Therefore, the DEN-induced hepatic cell death was examined in Hsp60c-expressing transgenic mice that had been primed with or without TNF-α. TUNEL staining of the liver tissue sections showed that the hepatic cell death was significantly reduced in Hsp60c-expressing transgenic mice compared to control mice (FIGS. 54-55). The data indicate that the cytosolic Hsp60 prevents the stress-induced cell death in vivo by promoting IKK/NF-κB activation, Hsp60 AS-ODN Suppresses Inflammation-Induced Bone Loss.

Figure 60:
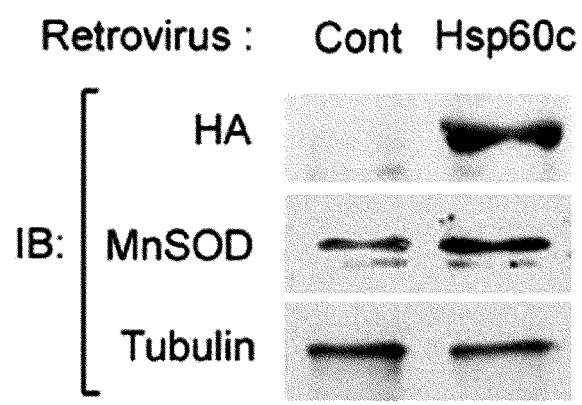
Figure 61:
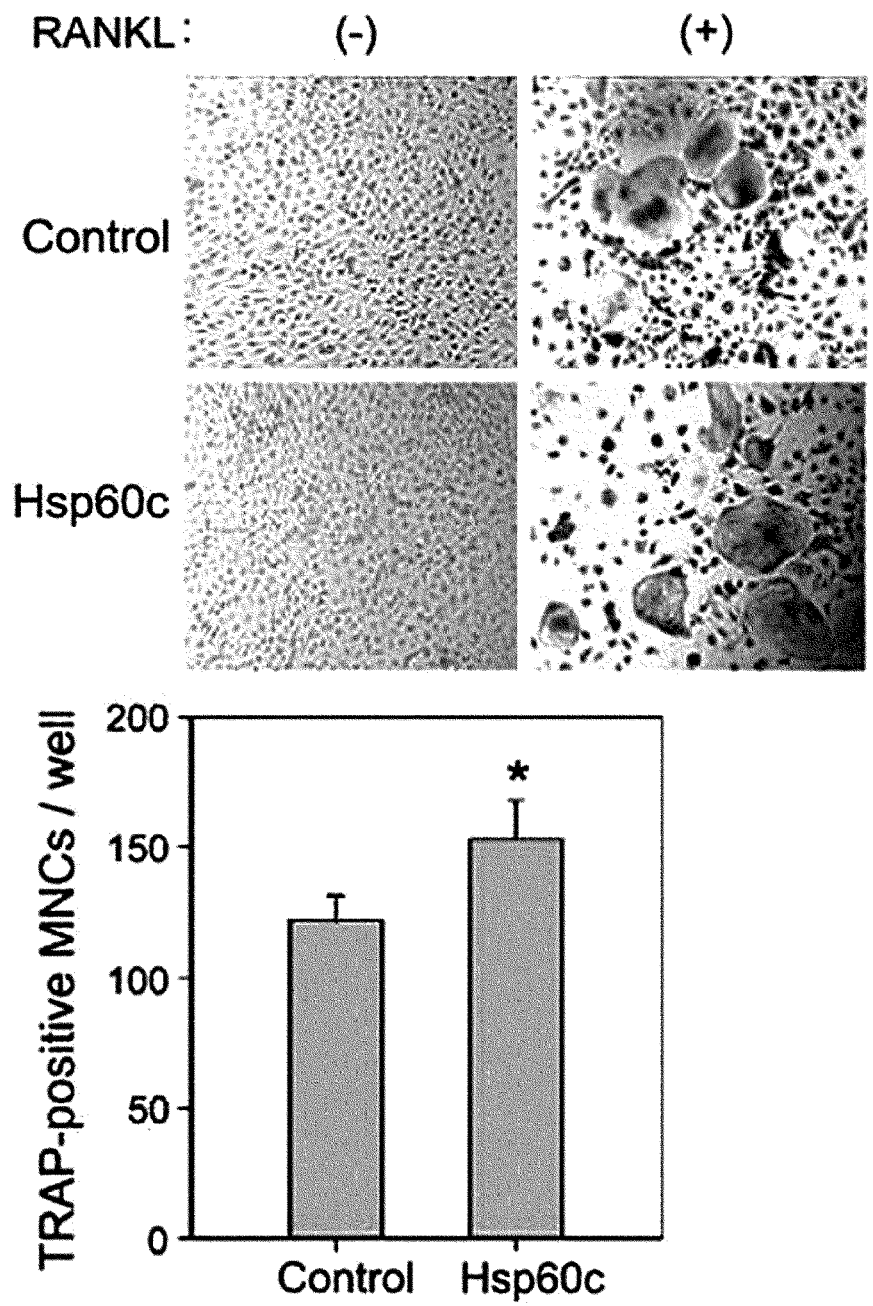

Clearly, Hsp60 AS-ODN has negative effects on intracellular activation of IKK/NF-κB pathway. Thus, the present inventors tested whether AS-ODN suppresses NF-κB-dependent inflammatory responses in vivo. NF-κB is a central survival transcription factor that is involved in osteoclast differentiation in response to RANKL or TNF-α in the presence of macrophage-colony stimulating factor (M-CSF) (Boyle W J et al., Nature, 423(6937): 337-342 (2003); Kobayashi K et al., J Exp Med., 191(2): 275-286 (2000)). Recently, it was reported that IKK-mediated NF-kB pathway is essential for RANK-induced osteoclastogenesis (Chaisson M L et al., J Biol. Chem., 279(52): 54841-8 (2004); Dai S, et al., Biol. Chem., 279(36): 37219-22 (2004); Ruocco M G et al., J Exp Med., 201(10): 1677-87 (2005)). Therefore, the present inventors tested the effects of Hsp60 AS-ODN on osteoclast differentiation. The bone marrow-derived macrophage/monocytic (BMM) cells treated with or without ODNs were stimulated with RANKL or TNF-α in the presence of macrophage-colony stimulating factor. Hsp60 AS-ODN remarkably suppressed the RANKL or TNF-α-induced TRAP-positive multinucleated osteoclast formation, compared to those treated without ODN or with S-ODNs (FIGS. 58-59), indicating that Hsp60 AS-ODN reduces osteoclast survival. The present inventors also performed the same studies in BMM cells transfected with retrovirus encoding cytosol-targeted Hsp60 (Hsp60c), Hsp60c expression increased SOD2 expression in RANKL-treated cells, compared to control virus-transfected cells (FIG. 60). Furthermore, Hsp60c expression clearly increased the RANKL-induced TRAP-positive osteoclast formation (FIG. 61). These results suggest that cytosolic Hsp60 induces SOD2 expression via IKK/NF-κB signaling, and thus involved in survival of osteoclasts.

Hsp60 AS-ODN Reduces Neointimal Thickness in Balloon Injured Vessels.

Balloon injury of blood vessels causes endothelial cell denudation and smooth muscle cell activation by pro-inflammatory factors released from recruited monocytes and platelet. Thus, NF-κB activation plays an important role in proliferation and survival of SMCs in balloon-injured blood vessels (Ohtani K et al., Circulation, 114(25): 2773-9(2006); Breuss J M et al., Circulation, 105(5): 633-8(2002); Autieri M V et al., Biochem Biophys Res Commun., 213(3): 827-36(1995)). In order to confirm this, the present inventors tested whether Hsp60 AS-ODN suppresses an increase in neointimal thickness by proliferative SMCs. First, transfer of ODNs to the injured carotid artery was tested by using FITC-conjugated ODN. ODNs were successfully transferred to the blood vessel wall in the presence of a transfection reagent, Oligofectamine™ (FIG. 62). When balloon catheter-injured lumen of the rat carotid artery is treated with mock or ODNs, Hsp60 AS-ODN treatment markedly suppresses an increase in neointimal thickness whereas S-ODN treatment showed no effect, compared to the mock-treated group (FIG. 63). Conclusively, TUNEL staining results showed that AS-ODN treatment, remarkably increased apoptotic cell death in the neointima (FIG. 64), indicating that the suppressed neointimal thickness is attributed to apoptotic cell death of SMCs.

Having described specific embodiments of the present invention, it will be apparent to those skilled in the art that the above embodiment is not limitative, but illustrative in all aspects, and the scope of this invention is to be determined by appended claims and their equivalents.

Effect of the Invention

The present invention relates to a pharmaceutical composition for the treatment of diseases associated with abnormal cell proliferation, comprising a cytosolic Hsp60 inhibitor as an active ingredient, and a screening method and kit using the same. According to the present invention, cytosolic Hsp60 interacts with IKK complex to be directly involved in the regulation of IKK activation, and subsequent activation of NF-κB pathway activates cell survival response. Therefore, abnormal cell proliferation-associated diseases such as cancer, inflammatory diseases or hyperproliferative vascular disorders can be effectively prevented or treated by inhibition of cytosolic Hsp60 gene expression or inhibition of binding between cytosolic Hsp60 protein and IKK protein, and a novel therapeutic agent for abnormal cell proliferation-associated diseases can also be screened.

What is claimed is:

1. A method for treating hyperproliferative vascular disorder, comprising administering to a subject in need thereof an inhibitor that inhibits cytosolic Hsp60 protein activity or reduces cytosolic Hsp60 protein level,
    wherein the hyperproliferative vascular disorder is arteriosclerosis, restenosis, stenosis, hemodialysis vascular access stenosis or osteoporosis.

2. The method according to claim 1, wherein the inhibitor is selected from the group consisting of antisense oligonucleotides, siRNAs, and aptamers that reduce cytosolic Hsp60 protein level.

3. The method according to claim 2, wherein the inhibitor is selected from the group consisting of antisense oligodeoxynucleotides of SEQ ID NOs. 3 to 7.

4. The method according to claim 1, wherein the inhibitor is selected from the group consisting of antibodies and single-chain variable fragments that, are specific to cytosolic Hsp60.

5. The method according to claim 4, wherein the inhibitor is an Hsp60-specific polyclonal antibody.

6. The method according to claim 1, wherein the inhibitor inhibits the interaction between cytosolic Hsp60 protein and IκB kinase (IKK).

7. The method according to claim 6, wherein the IKK is IKKα or IKKβ.

8. The method according to claim 6, wherein the IKK activates NF-κB pathway.

9. The method according to claim 8, wherein the activation of NF-κB pathway increases cell survival rate against apoptosis-inducing stress.

10. The method according to claim 1, wherein the cytosolic Hsp60 protein induces expression of MnSOD (nanganese-superoxide dismutase) or Bfl-1/A1.

11. The method according to claim 1, wherein the cytosolic Hsp60 protein reduces the mitochondrial-derived ROS (reactive oxygen species) level.

12. The method according to claim 1, wherein the cytosolic Hsp60 protein promotes serine phosphorylation of IKKα/β T-loop.

13. The method according to claim 1, wherein the inhibitor is identified by a screening method comprising:
    (a) treating an Hsp60 gene-containing cell with a test material;
    (b) analyzing level of the cytosolic Hsp60 protein; and
    (c) determining that the test material is the inhibitor when it reduces the level of the cytosolic Hsp60 protein.

14. The method according to claim 13, wherein the analysis is performed by in situ hybridization, radioimmunoprecipitation assay, immunoprecipitation, or ELISA (enzyme-linked immunosorbent assay).

15. The method according to claim 1, wherein the inhibitor is identified by a screening method comprising:
    (a) treating with a test material a cell or a cell extract that contains cytosolic Hsp60 protein and IKK (IκB kinase) protein;
    (b) analyzing whether the test material inhibits binding of cytosolic Hsp60 protein and IKK protein; and
    (c) determining that the test material is the inhibitor it inhibits binding of cytosolic Hsp60 protein and IKK protein.

* * * * *

SEQUENCE LISTING

```
<160> NUMBER OF SEQ ID NOS: 11

<210> SEQ ID NO 1
<211> LENGTH: 2339
<212> TYPE: DNA
<213> ORGANISM: Homo sapiens

<400> SEQUENCE: 1
acgcggtgcc gcggggcggg agtagaggcg gagggagggg acacgggctc attgcggtgt      60
gcgccctgca ctctgtccct cactcgccgc cgacgacctg tctcgccgag cgcacgcctt     120
gccgccgccc cgcagaaatg cttcggttac ccacagtctt tcgccagatg agaccggtgt     180
ccagggtact ggctcctcat ctcactcggg cttatgccaa agatgtaaaa tttggtgcag     240
atgcccgagc cttaatgctt caaggtgtag accttttagc cgatgctgtg gccgttacaa     300
tggggccaaa gggaagaaca gtgattattg agcagagttg gggaagtccc aaagtaacaa     360
aagatggtgt gactgttgca aagtcaattg acttaaaaga taaatacaaa aacattggag     420
ctaaacttgt tcaagatgtt gccaataaca caaatgaaga agctggggat ggcactacca     480
ctgctactgt actggcacgc tctatagcca aggaaggctt cgagaagatt agcaaaggtg     540
ctaatccagt ggaaatcagg agaggtgtga tgttagctgt tgatgctgta attgctgaac     600
ttaaaaagca gtctaaacct gtgaccaccc ctgaagaaat tgcacaggtt gctacgattt     660
ctgcaaacgg agacaaagaa attggcaata tcatctctga tgcaatgaaa aaagttggaa     720
gaaagggtgt catcacagta aaggatggaa aaacactgaa tgatgaatta gaaattattg     780
aaggcatgaa gtttgatcga ggctatattt ctccatactt tattaataca tcaaaaggtc     840
agaaatgtga attccaggat gcctatgttc tgttgagtga aagaaaatt tctagtatcc     900 agtccattgt acctgctctt gaaattgcca atgctcaccg taagcctttg gtcataatcg     960
ctgaagatgt tgatggagaa gctctaagta cactcgtctt gaataggcta aaggttggtc    1020
ttcaggttgt ggcagtcaag gctccagggt tggtgacaa tagaaagaac cagcttaaag    1080
atatggctat tgctactggt ggtgcagtgt ttggagaaga gggattgacc ctgaatcttg    1140
aagacgttca gcctcatgac ttaggaaaag ttggagaggt cattgtgacc aaagacgatg    1200
```

```
ccatgctctt aaaaggaaaa ggtgacaagg ctcaaattga aaaacgtatt caagaaatca    1260
ttgagcagtt agatgtcaca actagtgaat atgaaaagga aaaactgaat gaacggcttg    1320
caaaactttc agatggagtg gctgtgctga aggttggtgg acaagtgat gttgaagtga     1380 atgaaaagaa agacagagtt acagatgccc ttaatgctac aagagctgct gttgaagaag    1440
gcattgtttt gggaggggt tgtgccctcc ttcgatgcat tccagccttg gactcattga     1500
ctccagctaa tgaagatcaa aaattggta tagaaattat taaaagaaca ctcaaaattc     1560
cagcaatgac cattgctaag aatgcaggtg ttgaaggatc tttgatagtt gagaaaatta    1620
tgcaaagttc ctcagaagtt ggttatgatg ctatggctgg agattttgtg aatatggtgg    1680
aaaaaggaat cattgaccca acaaaggttg tgagaactgc tttattggat gctgctggtg    1740
tggcctctct gttaactaca gcagaagttg tagtcacaga aattcctaaa gaagagaagg    1800
accctggaat gggtgcaatg ggtggaatgg gaggtggtat gggaggtggc atgttctaac    1860
tcctagacta gtgctttacc tttattaatg aactgtgaca ggaagcccaa ggcagtgttc    1920
ctcaccaata acttcagaga agtcagttgg agaaaatgaa gaaaaaggct ggctgaaaat    1980
cactataacc atcagttact ggtttcagtt gacaaaatat ataatggttt actgctgtca    2040
ttgtccatgc ctacagataa tttatttttgt atttttgaat aaaaaacatt tgtacattcc   2100
tgatactggg tacaagagcc atgtaccagt gtactgcttt caacttaaat cactgaggca    2160
tttttactac tattctgtta aaatcaggat tttagtgctt gccaccacca gatgagaagt    2220
taagcagcct ttctgtggag agtgagaata attgtgtaca aagtagagaa gtatccaatt    2280
atgtgacaac ctttgtgtaa taaaaatttg tttaaagtta aaaaaaaaaa aaaaaaaa      2339

<210> SEQ ID NO 2
<211> LENGTH: 2319
<212> TYPE: DNA
<213> ORGANISM: Homo sapiens

<400> SEQUENCE: 2
gccccgacgc gcaccgcgat tcgccccaag ggccctgcgc aggacgctga cgcgaagact      60
cggaggcgga agaaaaaagg agctgtttct aggcttttct aggcgcccag ccgagaaatg     120
cttcggttac ccacagtctt tcgccagatg agaccggtgt ccagggtact ggctcctcat     180
ctcactcggg cttatgccaa agatgtaaaa tttggtgcag atgcccgagc cttaatgctt     240
caaggtgtag accttttagc cgatgctgtg gccgttacaa tggggccaaa gggaagaaca     300
gtgattattg agcagagttg gggaagtccc aaagtaacaa agatggtgt gactgttgca      360 aagtcaattg acttaaaaga taaatacaaa acattggag ctaaacttgt tcaagatgtt      420
gccaataaca caaatgaaga agctggggat ggcactacca ctgctactgt actggcacgc     480
tctatagcca aggaaggctt cgagaagatt agcaaaggtg ctaatccagt ggaaatcagg     540
agaggtgtga tgttagctgt tgatgctgta attgctgaac ttaaaaagca gtctaaacct     600
gtgaccaccc ctgaagaaat tgcacaggtt gctacgattt ctgcaaacgg agacaaagaa     660
attggcaata tcatctctga tgcaatgaaa aagttggaa gaaagggtgt catcacagta     720
aaggatggaa aaacactgaa tgatgaatta gaaattattg aaggcatgaa gtttgatcga    780
ggctatattt ctccatactt tattaataca tcaaaaggtc agaaatgtga attccaggat     840
gcctatgttc tgttgagtga aaagaaaatt tctagtatcc agtccattgt acctgctctt     900
gaaattgcca atgctcaccg taagcctttg gtcataatcg ctgaagatgt tgatggagaa     960
```

```
gctctaagta cactcgtctt gaataggcta aaggttggtc ttcaggttgt ggcagtcaag    1020
gctccagggt ttggtgacaa tagaaagaac cagcttaaag atatggctat tgctactggt    1080
ggtgcagtgt ttggagaaga gggattgacc ctgaatcttg aagacgttca gcctcatgac    1140
ttaggaaaag ttggagaggt cattgtgacc aaagacgatg ccatgctctt aaaaggaaaa    1200
ggtgacaagg ctcaaattga aaacgtatt caagaaatca ttgagcagtt agatgtcaca    1260
actagtgaat atgaaaagga aaactgaat gaacggcttg caaaactttc agatggagtg    1320
gctgtgctga aggttggtgg gacaagtgat gttgaagtga atgaaaagaa agacagagtt    1380
acagatgccc ttaatgctac aagagctgct gttgaagaag gcattgtttt gggagggggt    1440
tgtgccctcc ttcgatgcat tccagccttg gactcattga ctccagctaa tgaagatcaa    1500
aaaattggta tagaaattat taaaagaaca ctcaaaattc cagcaatgac cattgctaag    1560
aatgcaggtg ttgaaggatc tttgatagtt gagaaaatta tgcaaagttc ctcagaagtt    1620
ggttatgatg ctatggctgg agattttgtg aatatggtgg aaaaaggaat cattgaccca    1680
acaaaggttg tgagaactgc tttattggat gctgctggtg tggcctctct gttaactaca    1740
gcagaagttg tagtcacaga aattcctaaa aagagaaagg accctggaat gggtgcaatg    1800
ggtggaatgg gaggtggtat gggaggtggc atgttctaac tcctagacta gtgctttacc    1860
tttattaatg aactgtgaca ggaagcccaa ggcagtgttc ctcaccaata acttcagaga    1920
agtcagttgg agaaaatgaa gaaaaaggct ggctgaaaat cactataacc atcagttact    1980
ggtttcagtt gacaaaatat ataatggttt actgctgtca ttgtccatgc ctacagataa    2040
tttattttgt attttgaat aaaaaacatt tgtacattcc tgatactggg tacaagagcc    2100
atgtaccagt gtactgcttt caacttaaat cactgaggca ttttactac tattctgtta    2160 aaatcaggat tttagtgctt gccaccacca gatgagaagt taagcagcct ttctgtggag    2220
agtgagaata attgtgtaca aagtagagaa gtatccaatt atgtgacaac ctttgtgtaa    2280
taaaaatttg tttaaagtta aaaaaaaaaa aaaaaaaa                             2319
```

<210> SEQ ID NO 3
<211> LENGTH: 15
<212> TYPE: DNA
<213> ORGANISM: Artificial Sequence
<220> FEATURE:
<223> OTHER INFORMATION: antisense AS-1 ODN

<400> SEQUENCE: 3
agcatttctg cgggg                                                      15

<210> SEQ ID NO 4
<211> LENGTH: 15
<212> TYPE: DNA
<213> ORGANISM: Artificial Sequence
<220> FEATURE:
<223> OTHER INFORMATION: antisense AS-2 ODN

<400> SEQUENCE: 4
gggcatctgc accaa                                                      15

<210> SEQ ID NO 5
<211> LENGTH: 15
<212> TYPE: DNA
<213> ORGANISM: Artificial Sequence
<220> FEATURE:
<223> OTHER INFORMATION: antisense AS-3 ODN

<400> SEQUENCE: 5

-continued

```
tagtgccatc cccag                                                    15

<210> SEQ ID NO 6
<211> LENGTH: 15
<212> TYPE: DNA
<213> ORGANISM: Artificial Sequence
<220> FEATURE:
<223> OTHER INFORMATION: antisense AS-4 ODN

<400> SEQUENCE: 6
agccttgact gccac                                                    15

<210> SEQ ID NO 7
<211> LENGTH: 15
<212> TYPE: DNA
<213> ORGANISM: Artificial Sequence
<220> FEATURE:
<223> OTHER INFORMATION: antisense AS-5 ODN

<400> SEQUENCE: 7
cttgtcccac caacc                                                    15

<210> SEQ ID NO 8
<211> LENGTH: 22
<212> TYPE: DNA
<213> ORGANISM: Artificial Sequence
<220> FEATURE:
<223> OTHER INFORMATION: forward primer

<400> SEQUENCE: 8
atggcttcta gctatcctta tg                                            22

<210> SEQ ID NO 9
<211> LENGTH: 23
<212> TYPE: DNA
<213> ORGANISM: Artificial Sequence
<220> FEATURE:
<223> OTHER INFORMATION: reverse primer

<400> SEQUENCE: 9
gtagcaacct gtgcaatttc ttc                                           23

<210> SEQ ID NO 10
<211> LENGTH: 20
<212> TYPE: DNA
<213> ORGANISM: Artificial Sequence
<220> FEATURE:
<223> OTHER INFORMATION: forward primer

<400> SEQUENCE: 10
ctgctaacca tgttcatgcc                                               20

<210> SEQ ID NO 11
<211> LENGTH: 26
<212> TYPE: DNA
<213> ORGANISM: Artificial Sequence
<220> FEATURE:
<223> OTHER INFORMATION: reverse primer

<400> SEQUENCE: 11
acaagtttag ctccaatgtt tttgta                                        26
```